United States Patent
Lee et al.

(10) Patent No.: US 11,246,610 B2
(45) Date of Patent: Feb. 15, 2022

(54) ALIGNMENT INSTRUMENTS AND METHODS FOR USE IN TOTAL ANKLE REPLACEMENT

(71) Applicant: Paragon 28, Inc., Englewood, CO (US)

(72) Inventors: Daniel J. Lee, Denver, CO (US);
Joseph Dogué, Aurora, CO (US);
Randy Allard, Golden, CO (US);
Francis D. Barmes, Parker, CO (US);
Mark Ray Dalton, Austin, TX (US);
Albert Dacosta, Lone Tree, CO (US);
Spanky Raymond, Uniontown, OH (US)

(73) Assignee: Paragon 28, Inc., Englewood, CO (US)

( * ) Notice: Subject to any disclaimer, the term of this patent is extended or adjusted under 35 U.S.C. 154(b) by 0 days.

(21) Appl. No.: 17/345,406

(22) Filed: Jun. 11, 2021

(65) Prior Publication Data
US 2021/0298771 A1 Sep. 30, 2021

Related U.S. Application Data

(63) Continuation of application No. PCT/US2019/066149, filed on Dec. 13, 2019.
(Continued)

(51) Int. Cl.
*A61B 17/17* (2006.01)
*A61B 17/68* (2006.01)
(Continued)

(52) U.S. Cl.
CPC .......... *A61B 17/1775* (2016.11); *A61B 17/68* (2013.01); *A61B 90/13* (2016.02);
(Continued)

(58) Field of Classification Search
CPC ..... A61B 17/17; A61B 17/1775; A61B 17/68; A61F 2/4202; A61F 2/4606
See application file for complete search history.

(56) References Cited

U.S. PATENT DOCUMENTS

2008/0015599 A1 1/2008 D'Alessio et al.
2010/0331848 A1 12/2010 Smith et al.
(Continued)

FOREIGN PATENT DOCUMENTS

WO 2010122034 A1 10/2010
WO 2020123899 A1 6/2020

OTHER PUBLICATIONS

International Preliminary Report on Patentability for International Application No. PCT/US2019/066149, dated Jun. 8, 2021, 9 pages, International Bureau of WIPO.
(Continued)

*Primary Examiner* — Si Ming Ku
(74) *Attorney, Agent, or Firm* — Heslin Rothenberg Farley & Mesiti PC

(57) ABSTRACT

Alignment instruments may include joint-line referencing systems having an alignment arm having a body with first and second portions defining first and second sides. The first portion has at least one first pin tube through-hole extending from the first to the second side. The second portion has a first opening on the first side. A pin tube guide member is receivable in the first through-hole. The pin tube guide member has a passageway therethrough. An angelwing alignment member includes a portion receivable in the first opening of the alignment arm. An alignment foot is secured to the second portion, and the alignment foot has a handle and a shim. The shim is positionable in a joint between a first bone and a second bone, the alignment arm is alignable
(Continued)

relative to a first bone, and the pin tube guide is operable for securing a pin into the first bone.

21 Claims, 50 Drawing Sheets

Related U.S. Application Data

(60) Provisional application No. 62/899,655, filed on Sep. 12, 2019, provisional application No. 62/779,436, filed on Dec. 13, 2018.

(51) Int. Cl.
*A61F 2/46* (2006.01)
*A61B 90/13* (2016.01)
*A61F 2/42* (2006.01)

(52) U.S. Cl.
CPC .......... *A61F 2/4202* (2013.01); *A61F 2/4606* (2013.01); *A61B 2017/681* (2013.01)

(56) References Cited

U.S. PATENT DOCUMENTS

| | | | |
|---|---|---|---|
| 2012/0277745 A1* | 11/2012 | Lizee | G01B 5/24 |
| | | | 606/59 |
| 2013/0060253 A1 | 3/2013 | Couture et al. | |
| 2014/0025127 A1 | 1/2014 | Richter et al. | |
| 2015/0157339 A1 | 6/2015 | Mcginley et al. | |
| 2018/0221074 A1 | 8/2018 | Dacosta et al. | |

OTHER PUBLICATIONS

International Search Report and Written Opinion for international patent application No. PCT/US2019/066149 (published as WO 2020/123899), 12 pages, dated Apr. 14, 2020.

* cited by examiner

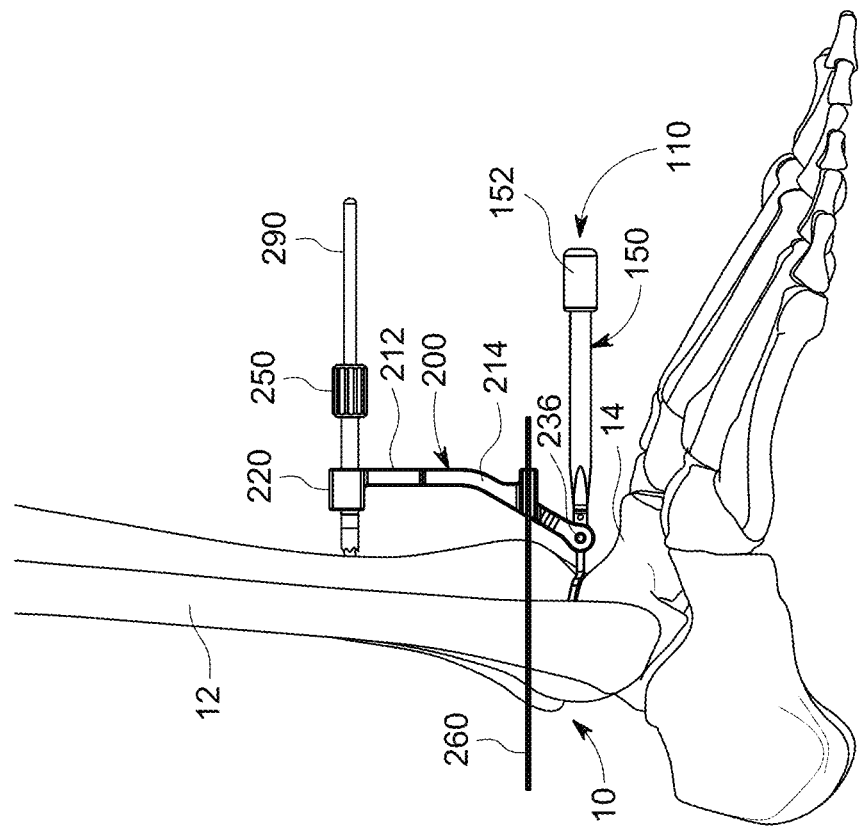
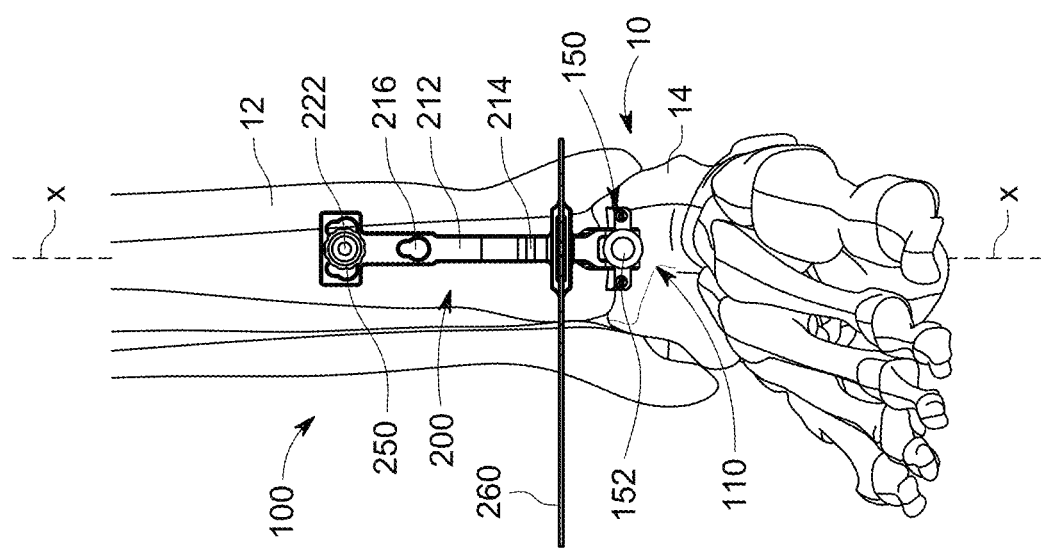
FIG. 12
FIG. 13

```
6000
```

┌─────────────────────────────────────────────┐
│ PLACING A SHIM INTO A JOINT BETWEEN A FIRST │─ 6100
│ BONE AND A SECOND BONE OF A PATIENT         │
└─────────────────────────────────────────────┘
                        │
┌─────────────────────────────────────────────┐
│ MOVING A HANDLE OPERABLY ATTACHED TO        │
│ THE SHIM TO POSITION AND/OR ORIENT AN       │─ 6200
│ ALIGNMENT ARM RELATIVE TO THE FIRST BONE    │
└─────────────────────────────────────────────┘
                        │
┌─────────────────────────────────────────────┐
│ INSERTING A FIRST PIN THROUGH A HOLE OF     │─ 6300
│ THE ALIGNMENT ARM AND INTO THE FIRST BONE   │
└─────────────────────────────────────────────┘
                        │
┌─────────────────────────────────────────────┐
│ REMOVING THE SHIM FROM THE JOINT AND THE    │─ 6400
│ ALIGNMENT ARM FROM THE FIRST PIN            │
└─────────────────────────────────────────────┘
                        │
┌─────────────────────────────────────────────┐
│ INSTALLING AN ALIGNMENT GUIDE ON THE        │─ 6500
│ INSTALLED PIN                               │
└─────────────────────────────────────────────┘
                        │
┌─────────────────────────────────────────────┐
│ USING A CUTTING GUIDE OPERABLY ATTACHED TO  │
│ THE ALIGNMENT GUIDE TO RESECT A PORTION OF  │─ 6600
│ THE FIRST BONE AND/OR THE SECOND BONE       │
└─────────────────────────────────────────────┘

```
┌─────────────────────────────────────────────────┐
│ PLACING A SHIM INTO A JOINT BETWEEN A FIRST     │── 7100
│ BONE AND A SECOND BONE OF A PATIENT             │
└─────────────────────────────────────────────────┘
                        │
┌─────────────────────────────────────────────────┐
│ MOVING A HANDLE OPERABLY ATTACHED TO            │
│ THE SHIM TO POSITION AND/OR ORIENT AN           │── 7200
│ ALIGNMENT ARM RELATIVE TO THE FIRST BONE        │
└─────────────────────────────────────────────────┘
                        │
┌─────────────────────────────────────────────────┐
│ INSERTING A FIRST PIN THROUGH A FIRST HOLE OF   │── 7300
│ THE ALIGNMENT ARM AND INTO THE FIRST BONE       │
└─────────────────────────────────────────────────┘
                        │
┌─────────────────────────────────────────────────┐
│ INSERTING A SECOND PIN THROUGH A SECOND HOLE    │── 7400
│ OF THE ALIGNMENT ARM AND INTO THE FIRST BONE    │
└─────────────────────────────────────────────────┘
                        │
┌─────────────────────────────────────────────────┐
│ REMOVING THE SHIM FROM THE JOINT AND THE        │── 7500
│ ALIGNMENT ARM FROM THE FIRST AND THE SECOND PIN │
└─────────────────────────────────────────────────┘
                        │
┌─────────────────────────────────────────────────┐
│ INSTALLING AN ALIGNMENT GUIDE ON THE            │── 7600
│ INSTALLED PIN                                   │
└─────────────────────────────────────────────────┘
                        │
┌─────────────────────────────────────────────────┐
│ USING A CUTTING GUIDE OPERABLY ATTACHED TO      │
│ THE ALIGNMENT GUIDE TO RESECT A PORTION OF      │── 7700
│ THE FIRST BONE AND/OR THE SECOND BONE           │
└─────────────────────────────────────────────────┘
```

FIG. 69

ALIGNMENT INSTRUMENTS AND METHODS FOR USE IN TOTAL ANKLE REPLACEMENT

CROSS REFERENCE TO RELATED APPLICATIONS

This application is a continuation of International Patent Application No. PCT/US2019/066149, filed on Dec. 13, 2019, entitled "Alignment Instruments And Methods For Use In Total Ankle Replacement", which international patent application claims priority benefit under 35 U.S.C. § 119(e) of U.S. Provisional Patent Application No. 62/899,655, filed Sep. 12, 2019, entitled "Alignment Instruments And Methods For Use In Total Ankle Replacement", and which international patent application claims priority benefit under 35 U.S.C. § 119(e) of U.S. Provisional Patent Application No. 62/779,436, filed Dec. 13, 2018, entitled "Joint Replacement Systems And Methods Of Use And Assembly", which applications are hereby incorporated herein by reference in their entireties.

TECHNICAL FIELD

The present disclosure relates generally to general, podiatric, and orthopaedic surgery related to joint deformities. More specifically, but not exclusively, the present disclosure relates to instruments, systems, and methods for maintaining, correcting and/or resurfacing joint surfaces.

BACKGROUND

Typically, implant alignment or guide systems attach to a patient, such as to one or more bones of an extremity of the patient. For example, in an ankle joint replacement system or surgery, an alignment guide is typically attached to the patient's foot and along the length of the tibia bone (e.g., via pins, k-wire or other removable mechanical fasteners).

SUMMARY

Aspects of the present disclosure provide implant alignment instruments, guides, methods, and systems for correcting bone deformities in the foot and ankle. Shortcomings of the prior art are overcome and additional advantages are provided through the provision in one embodiment of a joint-line referencing system, which includes, for example, an alignment arm having a body with a first portion and a second portion. The first portion and the second portions define a first side and a second side. The first portion has at least one first pin tube through-hole extending from the first side to the second side. The second portion has a first opening on the first side. A first pin tube guide member is receivable in the at least one first pin tube through-hole. The first pin tube guide member has a passageway therethrough. An angelwing alignment member includes a portion receivable in the at least one first opening of the alignment arm. An alignment foot is secured to the second portion, and the alignment foot has a handle extending away from the first side and a shim extending away from the second side. The shim is positionable in a joint between a first bone and a second bone, the alignment arm is alignable relative to a first bone, and the pin tube guide is operable for securing a pin into the first bone.

In another embodiment, a surgical method includes, for example, providing the above joint-line referencing system placing the shim of the alignment foot into a joint between a tibia and a talus of a patient, inserting the pin tube guide member in the at least one pin tube hole of the alignment arm, moving the handle of the alignment foot to orient the alignment arm, inserting a first pin in the passageway of the pin tube guide member and into the tibia of the patient, and removing the joint-line referencing system from the joint and the first pin.

In another embodiment, a surgical method includes, for example, providing the above joint-line referencing system, placing the shim of the alignment foot into a joint between a tibia and a talus of a patient, inserting the pin tube guide member in the at least one first pin tube through-hole of the alignment arm, inserting a second pin tube guide member in a second pin tube hole of the alignment arm, moving the handle of the alignment foot to orient the alignment arm, inserting a first pin in the first passageway of the first pin tube guide member and into the tibia of the patient, inserting a second pin in the second passageway of the second pin tube guide member and into the tibia of the patient, and removing the joint-line referencing system from the joint and the first and second pins.

In another embodiment, a surgical method includes, for example, placing a shim into a joint between a first bone and a second bone of a patient, moving a handle operably attached to the shim to position and/or orient an alignment arm relative to the first bone, inserting a first pin through a hole of the alignment arm and into the first bone, and removing the shim from the joint and the alignment arm from the first pin.

In another embodiment, a joint line pointer includes, for example, a body and an elongated handle. The body includes a first side, a second side, and an upper portion having a coupling member for coupling to an alignment system. The elongated handle includes a first end attached to a first side of said body. A lower portion of the body includes a first laterally-extending portion having a distal end extending between said first side and said second side, and a second laterally-extending portion having a distal end extending between said first side and said second side. The first and second laterally-extending portions are alignable with a joint line between a first bone and a second bone.

These and other objects, features and advantages of the present disclosure will become apparent from the following detailed description of the various embodiments of the present disclosure taken in conjunction with the accompanying drawings.

BRIEF DESCRIPTION OF THE DRAWINGS

The accompanying drawings, which are incorporated in and constitute a part of the specification, illustrate embodiments of the present disclosure and together with the detailed description herein, serve to explain the principles of the present disclosure. The drawings are only for purposes of illustrating preferred embodiments and are not to be construed as limiting the present disclosure. It is emphasized that, in accordance with the standard practice in the industry, various features are not drawn to scale. In fact, the dimensions of the various features may be arbitrarily increased or reduced for clarity of discussion. The foregoing and other objects, features and advantages of the disclosure are apparent from the following detailed description taken in conjunction with the accompanying drawings in which:

FIG. 12 is a front elevational view of the joint-line referencing system of FIG. 1 positioned relative to a patient's lower extremity, according to an embodiment of the present disclosure;

FIG. 13 is a side elevational view of the joint-line referencing system of FIG. 12 and a pin attached to the patient's lower extremity, according to an embodiment of the present disclosure;

FIG. 68 is a flowchart of a surgical method, according to an embodiment of the present disclosure; and FIG. 69 is a flowchart of a surgical method, according to an embodiment of the present disclosure.

DETAILED DESCRIPTION

Figure 1:
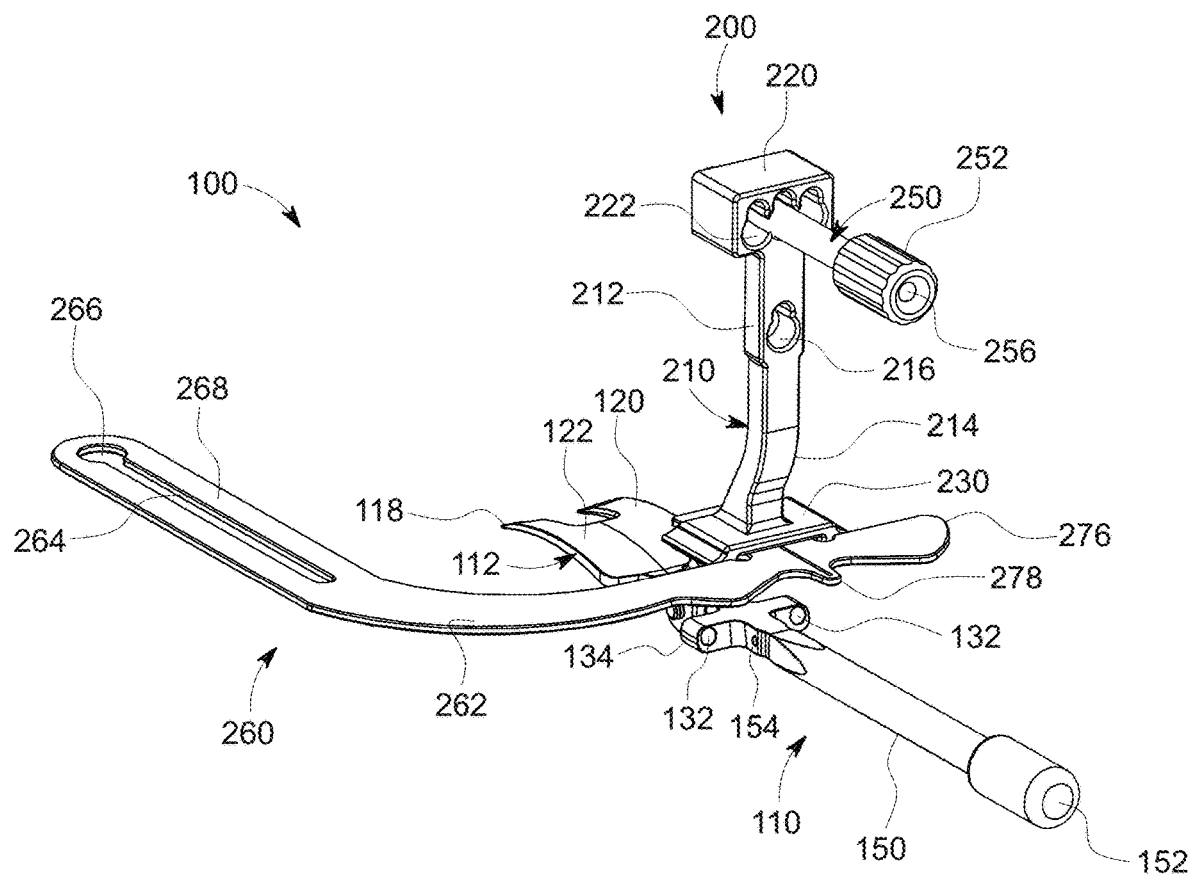
FIG. 1 is a perspective view of a joint-line referencing system, according to an embodiment of the present disclosure.
Figure 2:
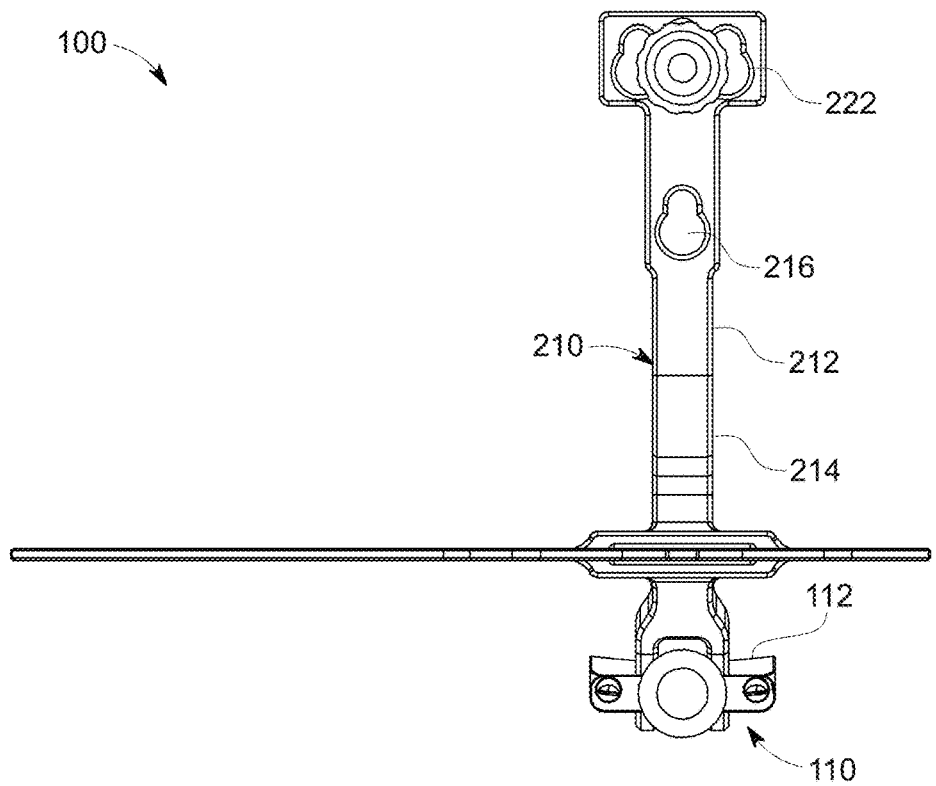
FIG. 2 is a front elevational view of the joint-line referencing system of FIG. 1, according to an embodiment of the present disclosure.
Figure 3:
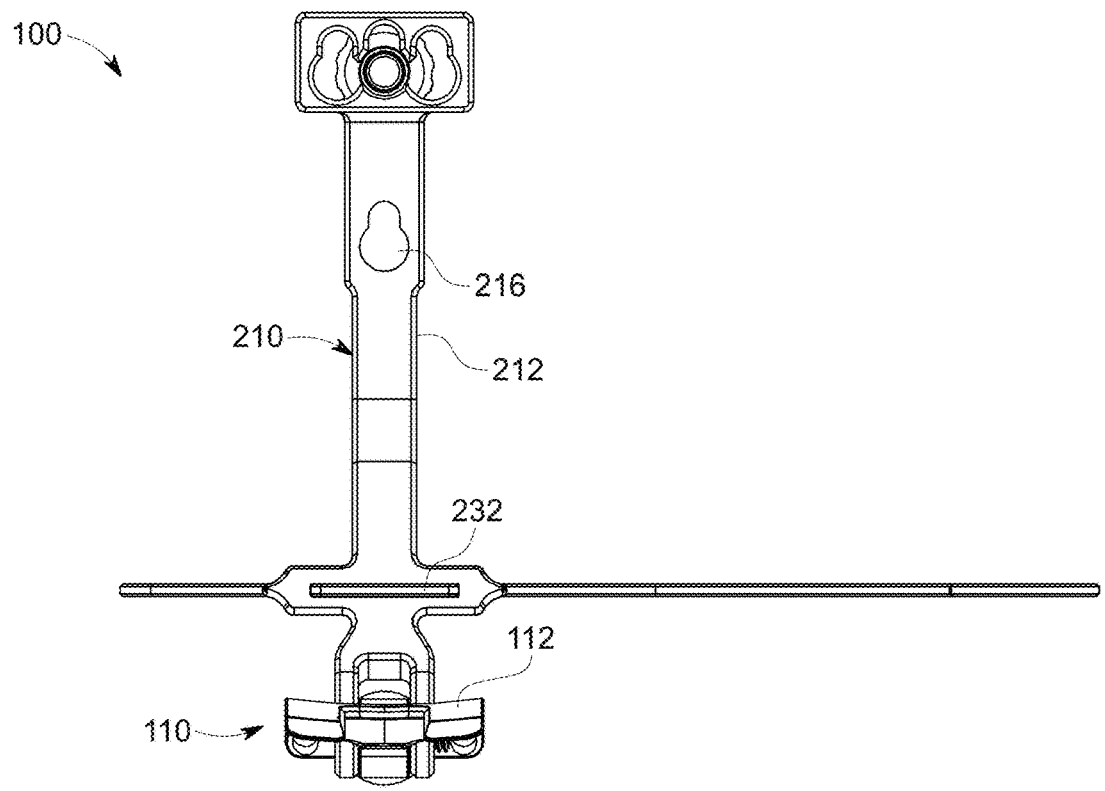
FIG. 3 is a rear elevational view of the joint-line referencing system of FIG. 1, according to an embodiment of the present disclosure.
Figure 4:
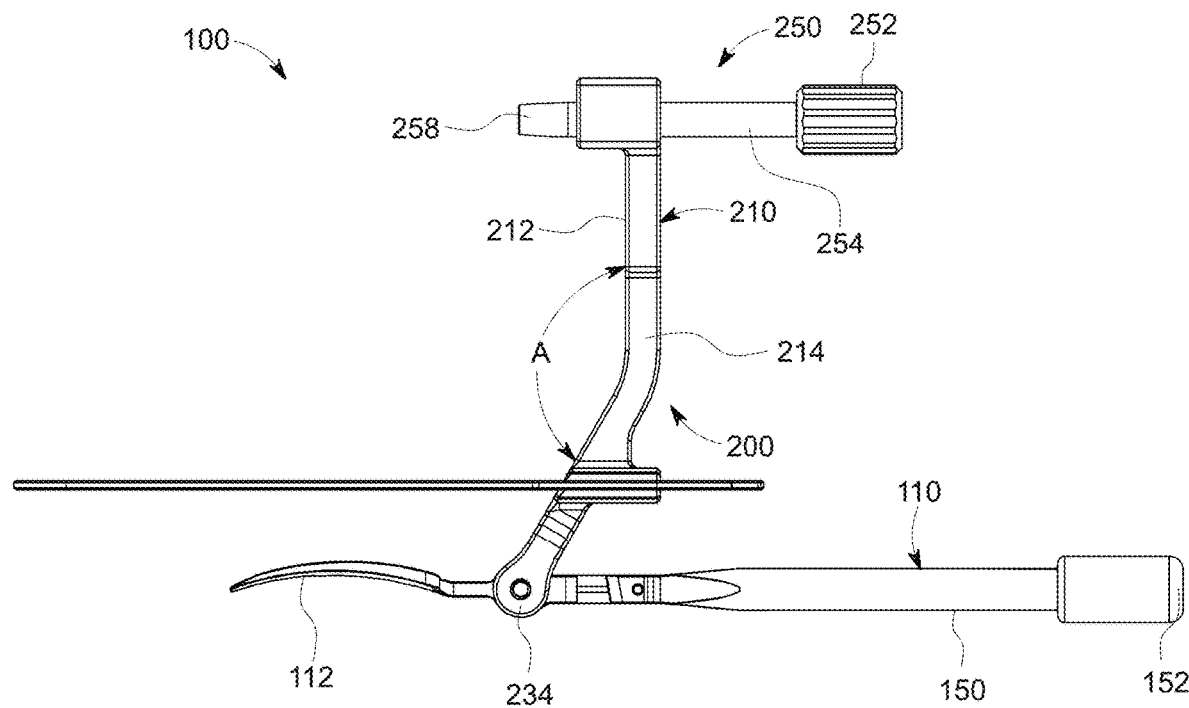
FIG. 4 is a first side elevational view of the joint-line referencing system of FIG. 1, according to an embodiment of the present disclosure.
Figure 5:
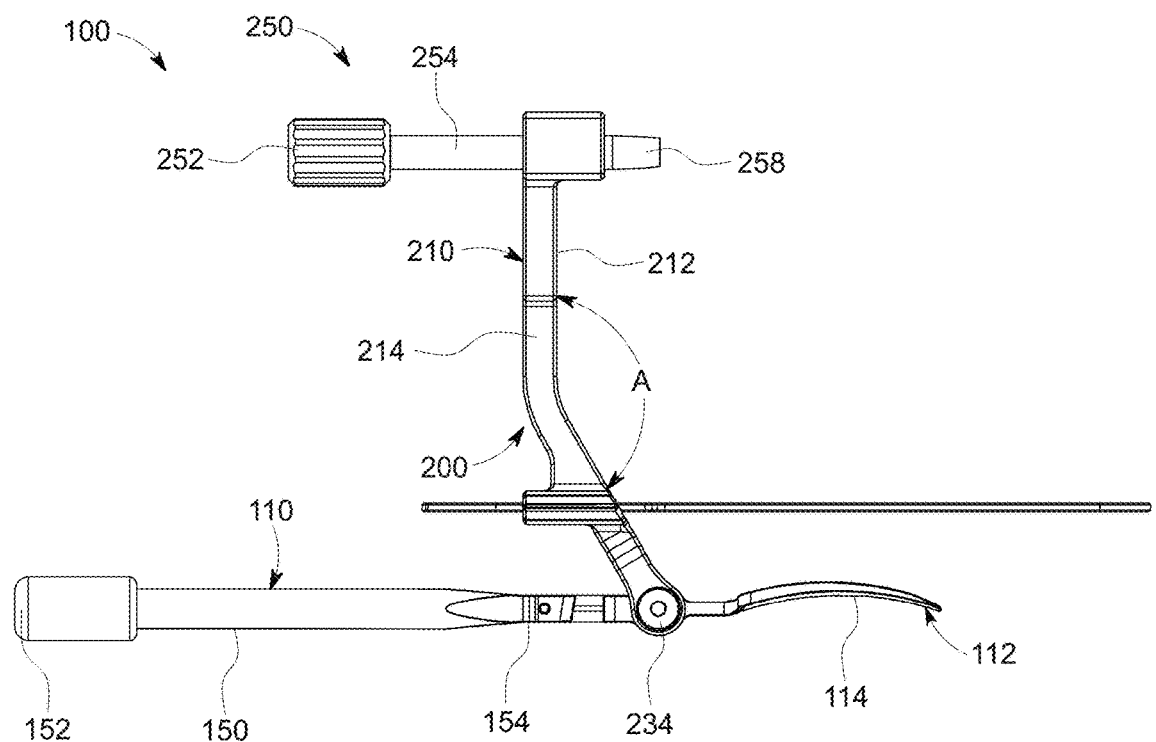
FIG. 5 is a second side elevational view of the joint-line referencing system of FIG. 1, according to an embodiment of the present disclosure.
Figure 7:
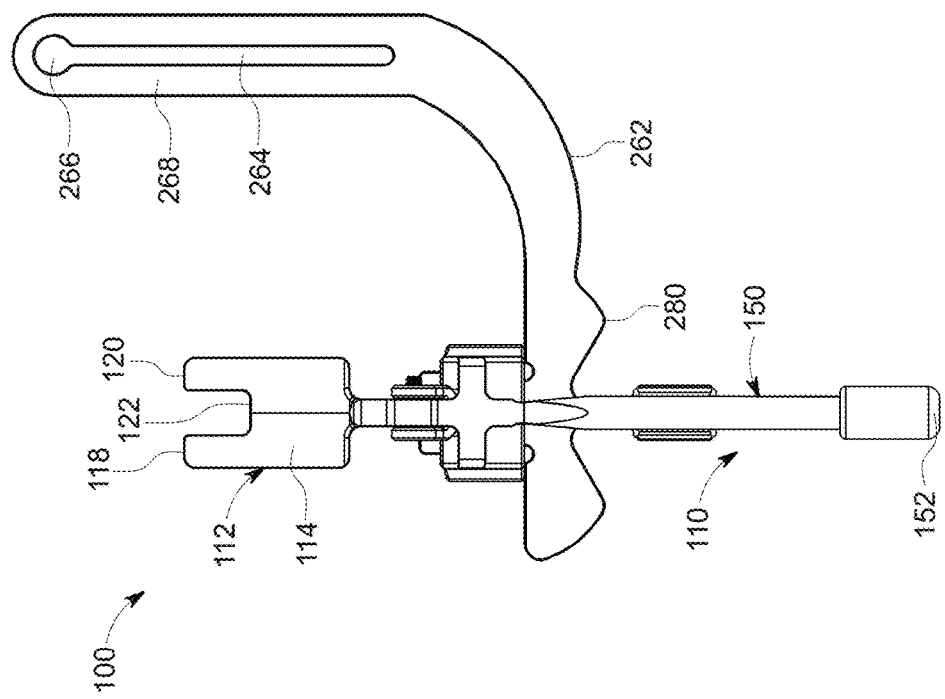
FIG. 7 is a bottom view of the joint-line referencing system of FIG. 1, according to an embodiment of the present disclosure.
Figure 6:
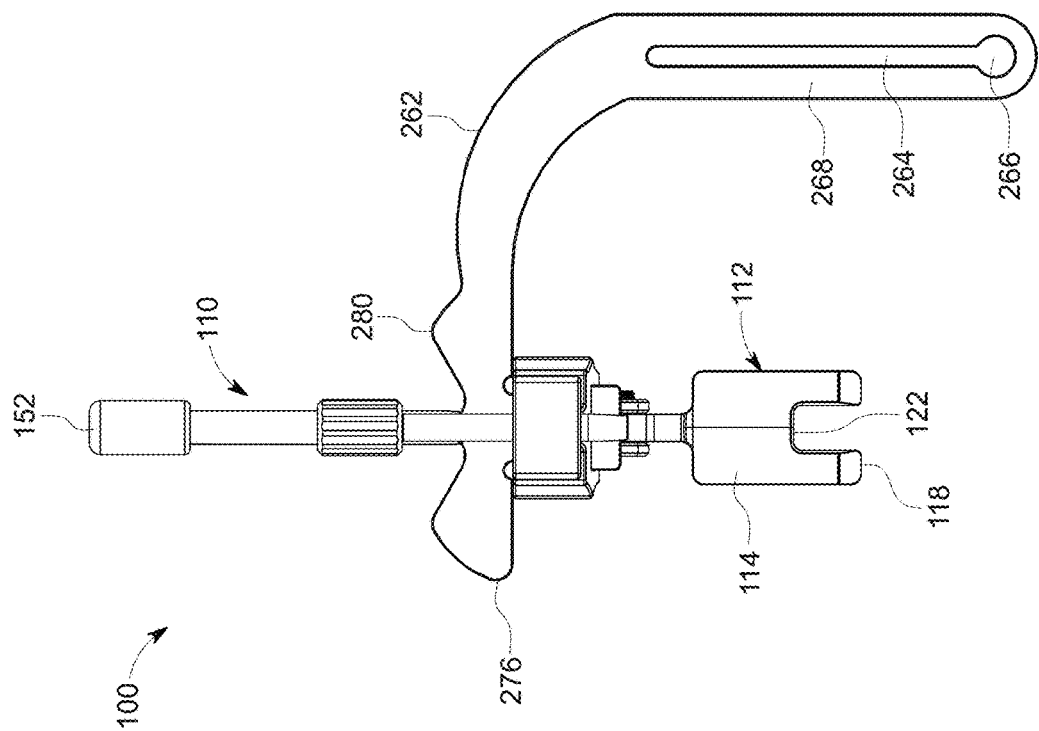
FIG. 6 is a top view of the joint-line referencing system of FIG. 1, according to an embodiment of the present disclosure.

Generally stated, disclosed herein are apparatus and methods for ankle replacement surgery and correction of bone deformities in the foot and ankle.

The present disclosure is directed to instruments, guides, systems and related methods for, for example, total ankle replacement prostheses. The instruments, guides, systems and related methods may facilitate preparation of a tibia and/or talus of a patient for implantation of a total ankle prosthesis therein. The instruments, guides, systems and related methods may also facilitate selection of a particular size of a tibial trialing component, tibial implant component, a talus trialing component, a talus implant component, and/or a tibial insert of the total ankle prosthesis that suits the patient. The instruments, guides, systems and methods facilitate proper alignment of the implant with the mechanical axis of an extremity of a patient. In some embodiments, the instruments, guides, systems and methods may facilitate bone resection and implantation of an implant into one or more bones so that the implant is properly aligned with the mechanical axis (or another axis or anatomical axis or reference point) of the extremity of a patient. The instruments, guides, systems and methods of the present disclosure may be utilized with any anatomical structure(s) of a patient to facilitate bone resection and alignment of an implant with an axis (e.g., mechanical axis, weight-bearing axis, anatomical axis, etc.) of one or more anatomical structures of interest.

In this detailed description and the following claims, the words proximal, distal, anterior or plantar, posterior or dorsal, medial, lateral, superior and inferior are defined by their standard usage for indicating a particular part or portion of a bone, joint (or any other anatomical structure) or implant according to the relative disposition of the natural bone, joint (or any other anatomical structure) or directional terms of reference. For example, "proximal" means the portion of a device or instrument nearest the torso, while "distal" indicates the portion of the device or instrument farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regard to the foot and/or ankle, the term "dorsal" refers to the top of the foot and the term "plantar" refers the bottom of the foot.

Similarly, positions or directions may be used herein with reference to anatomical structures or surfaces. For example, as the current instruments, guides, systems and related methods (and components thereof) are described herein with reference to use with the bones of the ankle, the bones of the foot, ankle and lower leg may be used to describe the surfaces, positions, directions or orientations of the instruments, guides, systems and related methods (and components thereof). Further, the instruments, guides, systems and related methods, and the aspects, components, features and the like thereof, disclosed herein may be described with respect to one side of the body (e.g., the left or right ankle) for brevity purposes. However, as the human body is relatively symmetrical or mirrored about a line of symmetry (midline), it is hereby expressly contemplated that the instruments, guides, systems and related methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the instruments, guides, systems and related methods, and the aspects, components, features and the like thereof, described herein with respect to the right ankle of a patient may be mirrored so that they likewise function with the left ankle of the patient. Further, the instruments, guides, systems and related methods, and the aspects, components, features and the like thereof, disclosed herein are described with respect to the ankle for brevity purposes, but it should be understood that the instruments, guides, systems and related methods (and components thereof) may be used with other joints of a human body (or other mammalian body).

The present disclosure may provide implant guides, devices, systems, and methods for total ankle replacements and correction of bone deformities in the foot and ankle. For example, in some embodiments, the joint-line referencing systems described herein may optimize positioning designed to fit the talar and tibial curvature in both anterior-posterior and medial-lateral directions. In particular, the joint-line referencing systems may allow for the streamlining of surgical techniques, improvement in the accuracy of surgery set-up procedures, and reduction of the likelihood of misplacement of bone screws.

With reference to FIG. 1-11, therein illustrated is a joint-line referencing system 100, according to an embodiment of the present disclosure. For example, in some embodiments, the joint-line referencing system 100 is operable with a tibia alignment guide (TAG) tower 300 (FIG. 16), as described in greater detail below. In this illustrated embodiment, the joint-line referencing system 100 may include, for example, an alignment arm 200, a pin tube guide member 250, an angelwing alignment member 260, and an alignment foot 110 having a handle 150 and a curved shim 112.

Figure 20:
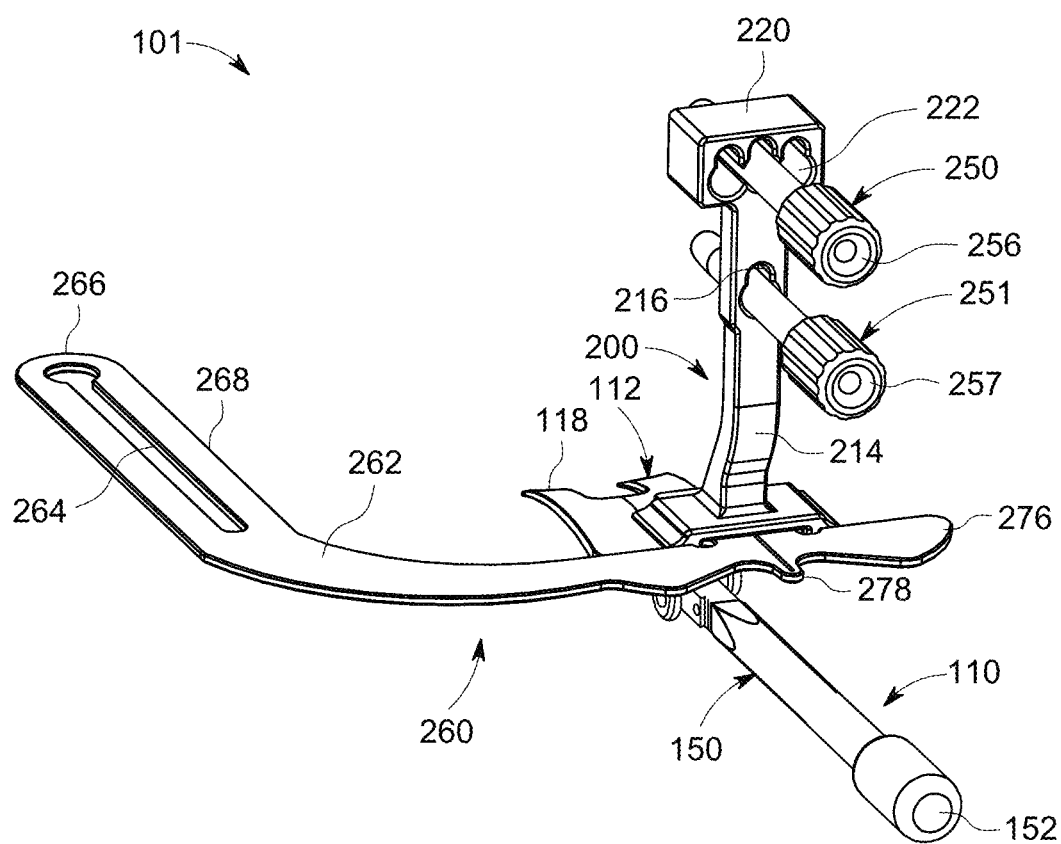
FIG. 20 is a top perspective view of a joint-line referencing system, according to an embodiment of the present disclosure.
Figure 21:
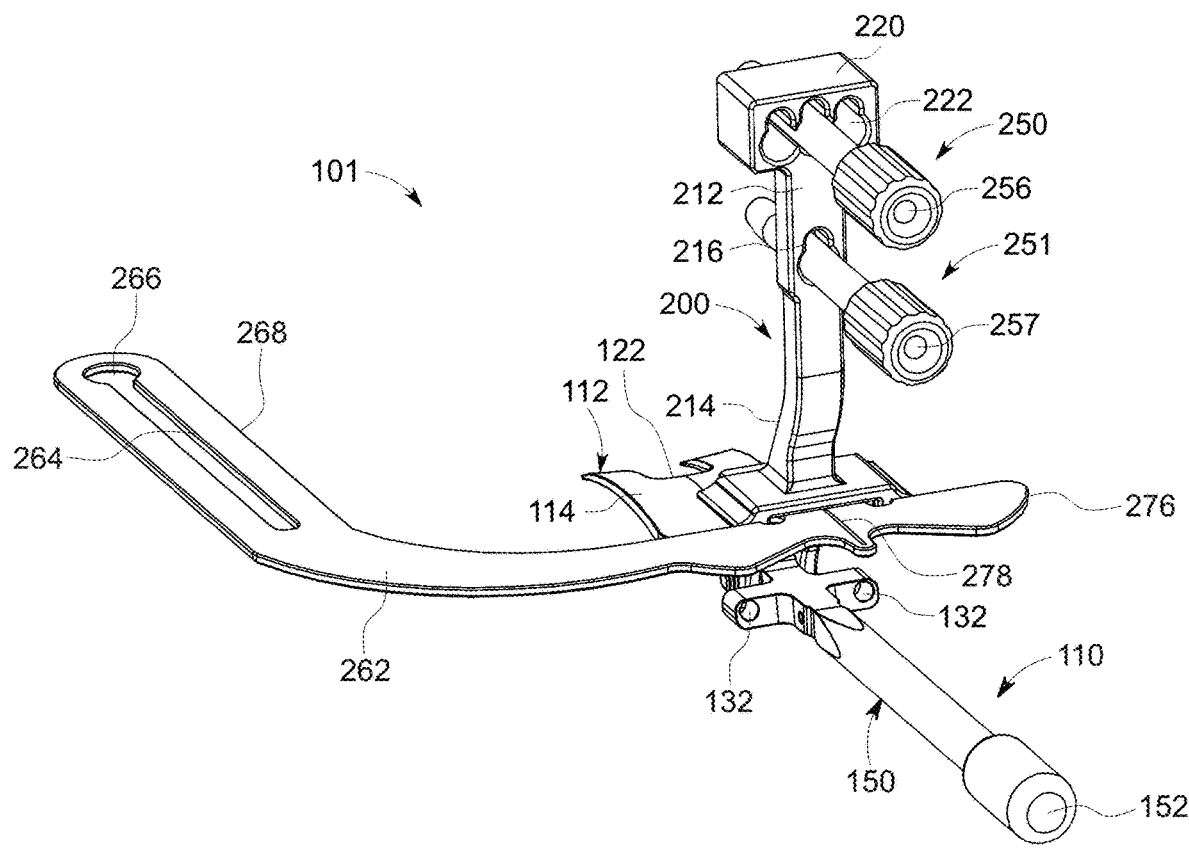
FIG. 21 is a top perspective view of the joint-line referencing system of FIG. 20, according to an embodiment of the present disclosure.
Figure 22:
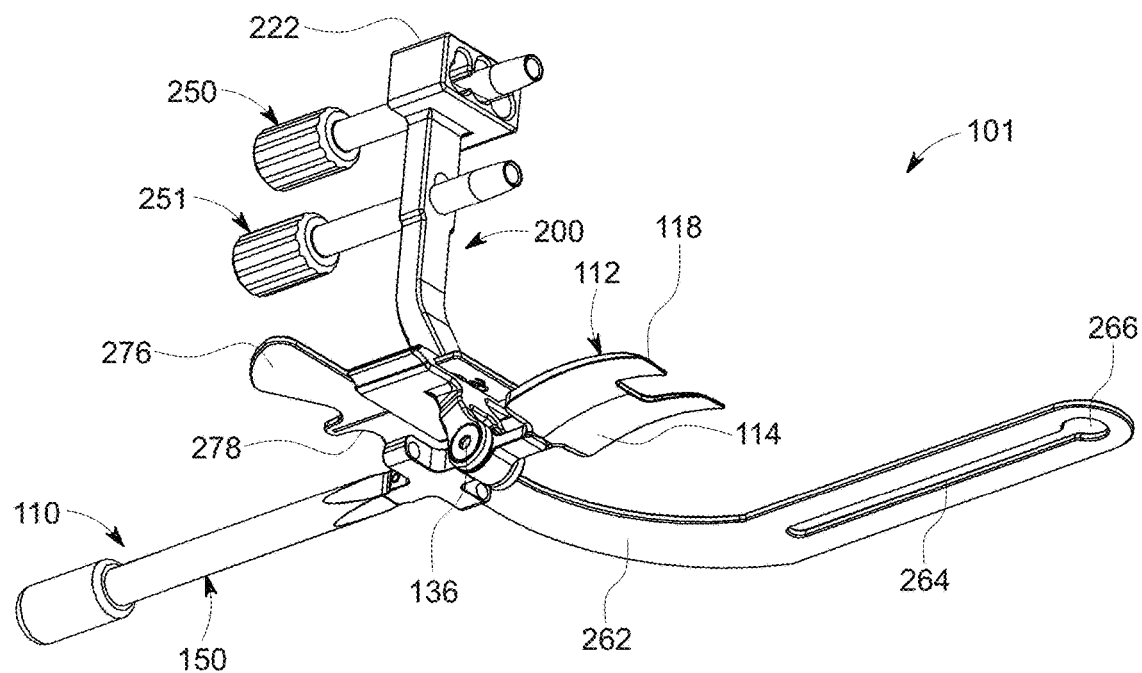
FIG. 22 is a bottom perspective view of the joint-line referencing system of FIG. 20, according to an embodiment of the present disclosure.
Figure 23:
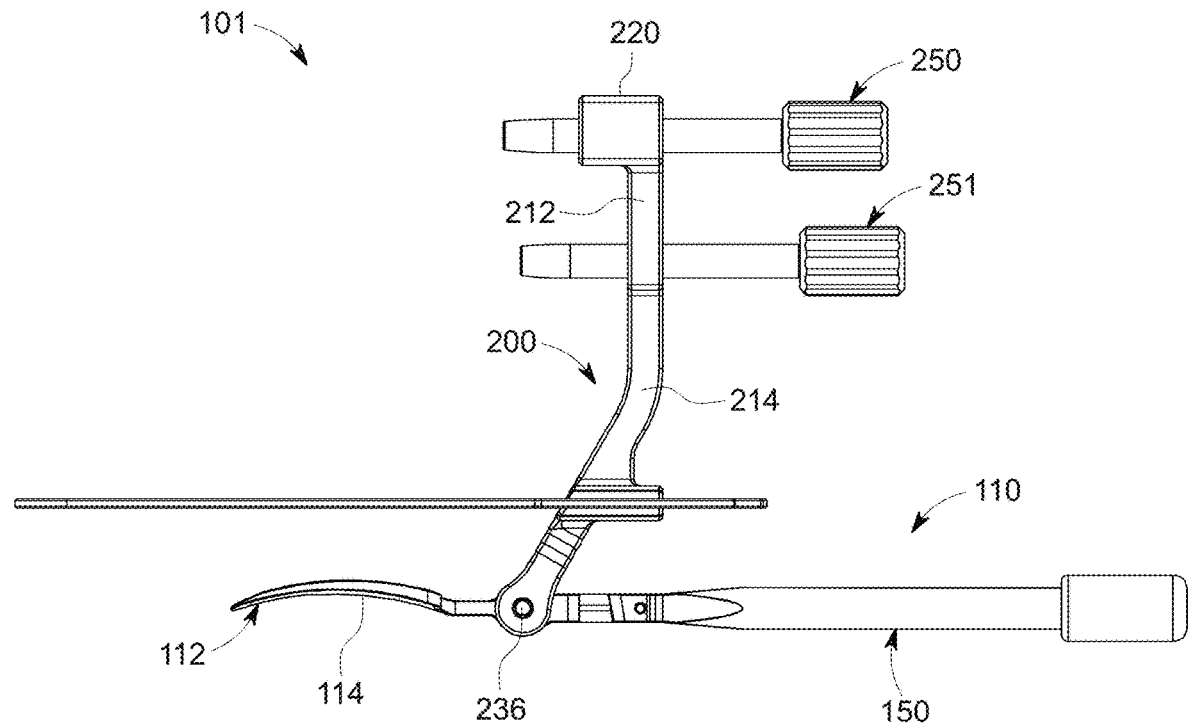
FIG. 23 is a side elevational view of the joint-line referencing system of FIG. 20, according to an embodiment of the present disclosure.
Figure 24:
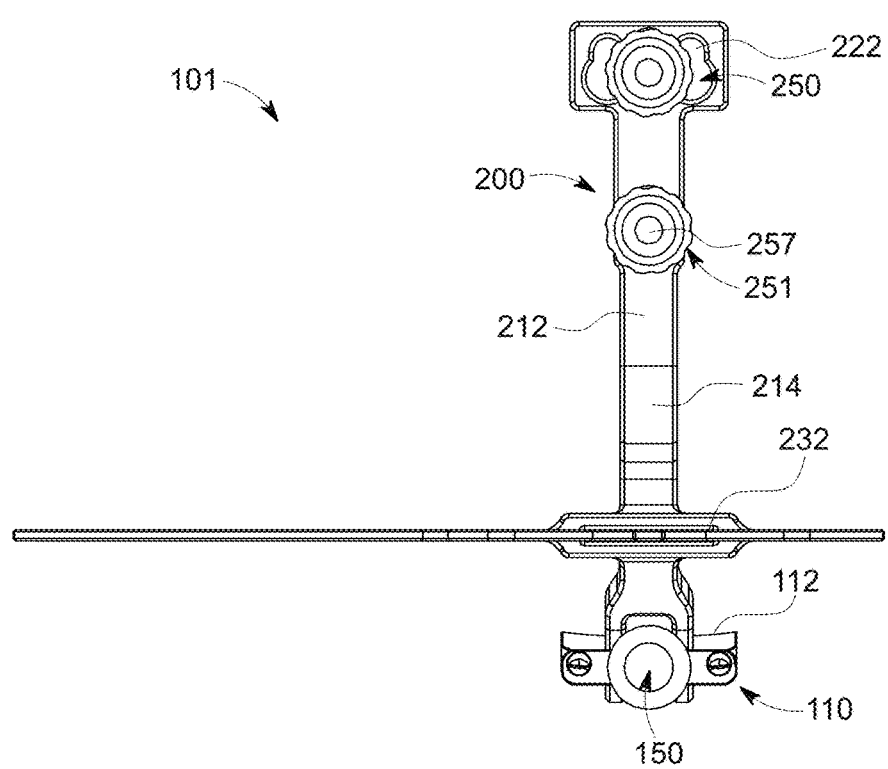
FIG. 24 is a front elevational view of the joint-line referencing system of FIG. 20, according to an embodiment of the present disclosure.

In this exemplary embodiment, the alignment arm 200 may include a body 210 having a first portion 212 and a second portion 214. The first portion 212 of the alignment arm 200 may include a pin tube holder 220 defining at least one pin tube through-hole 222 for receiving the pin tube guide member 250. A pin tube through-hole 216 is operable for receiving a second pin tube guide member (FIG. 20) for use with a fast-track alignment system 600 (FIG. 27) as described in greater detail below. The at least one pin tube through-hole 222 may be separate individual side-by-side holes or a plurality of overlapping pin tube through-holes that allow for anatomic variations. The at least one pin tube through-hole 222 may be, for example, three holes as shown in the depicted embodiment to allow for anatomic variations. The at least one pin tube through-hole 222 (and the pin tube through-hole 216) may be oblong or elongated to allow easier removal of the shim 112 from the joint while leaving one or more pins or guidewires in place, for example, by reducing binding, as described below.

Figure 8:
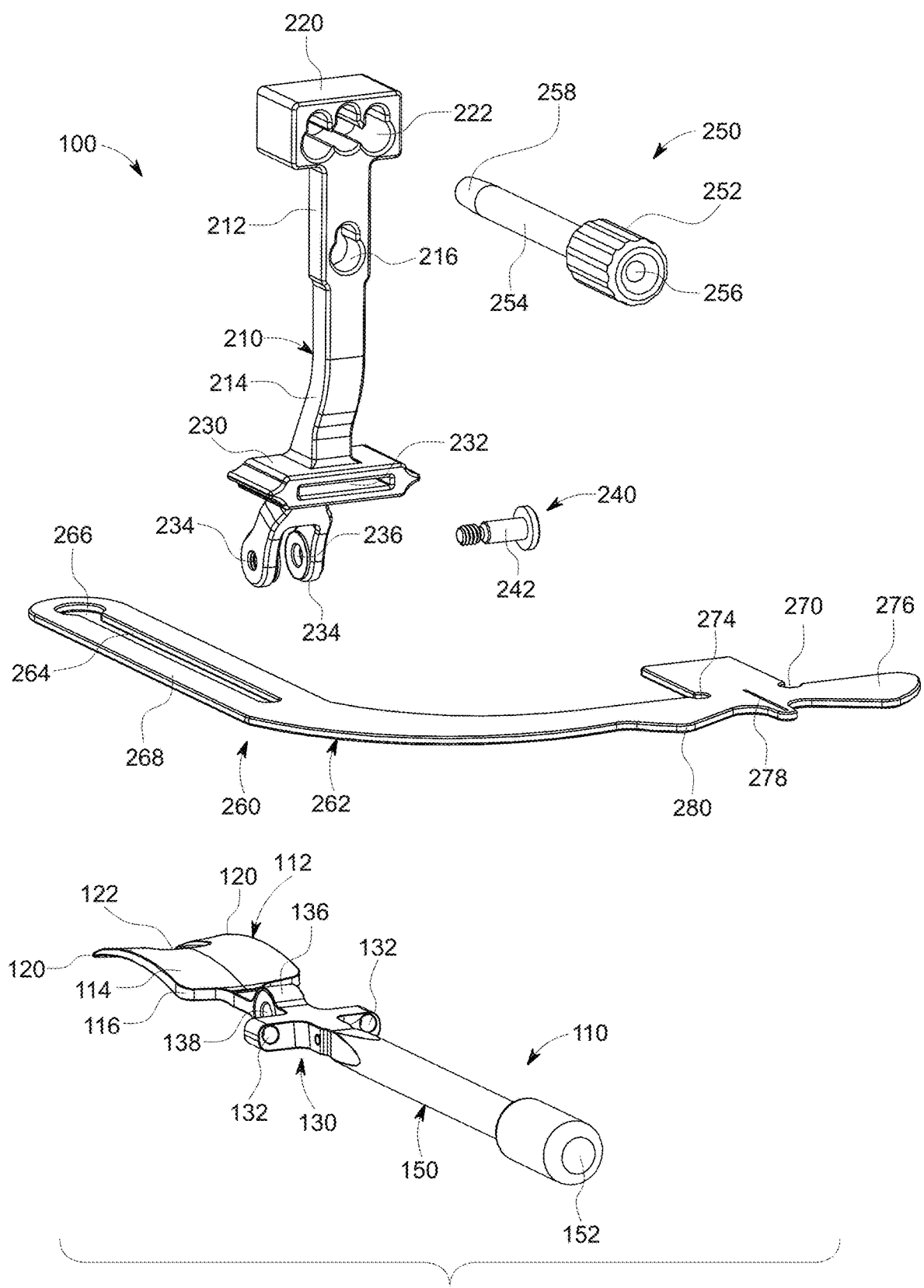
FIG. 8 is an exploded, top perspective view of the joint-line referencing system of FIG. 1, according to an embodiment of the present disclosure.
Figure 9:
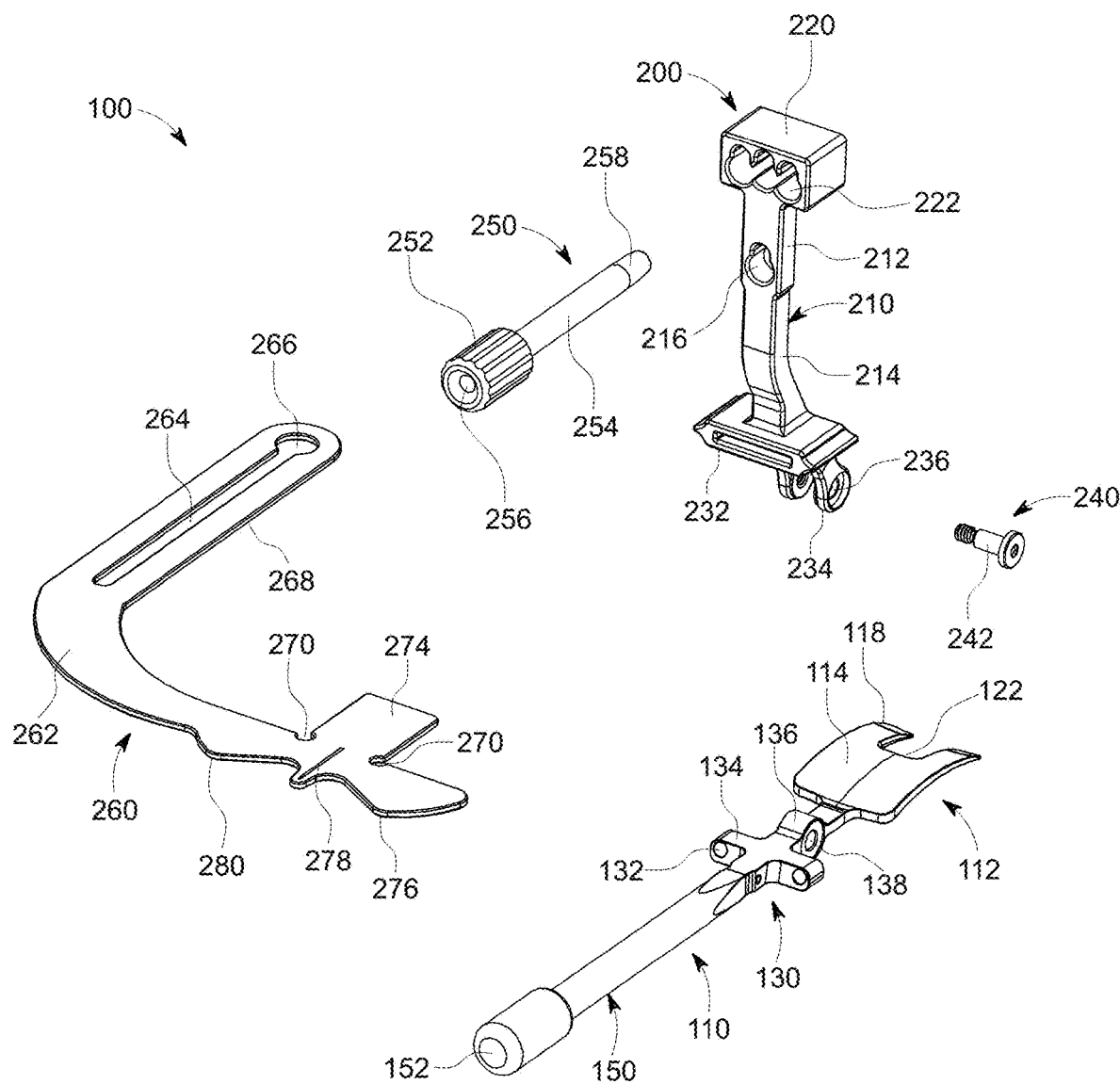
FIG. 9 is an exploded, top perspective view of the joint-line referencing system of FIG. 1, according to an embodiment of the present disclosure.
Figure 10:
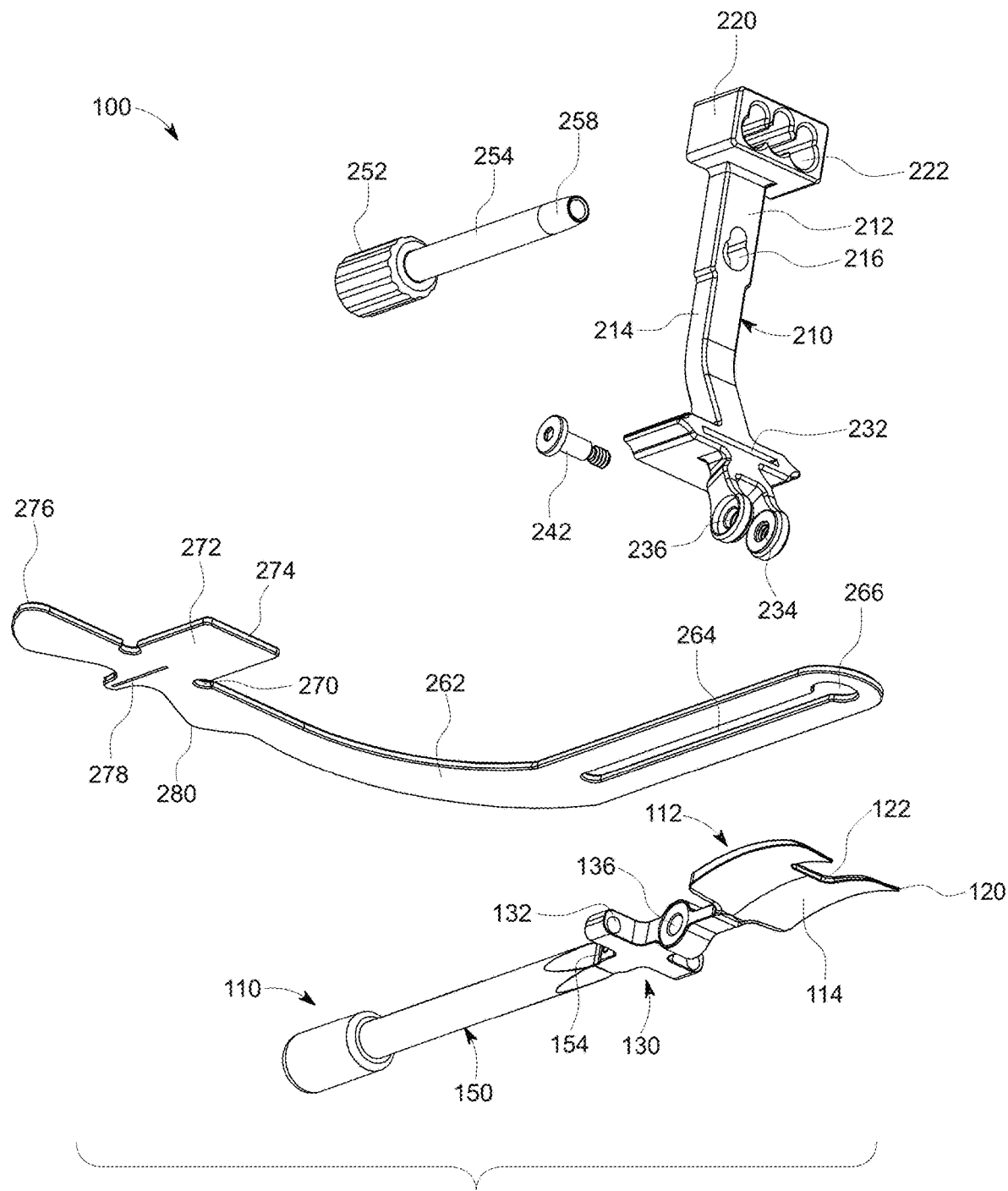
FIG. 10 is an exploded, bottom perspective view of the joint-line referencing system of FIG. 1, according to an embodiment of the present disclosure.
Figure 11:
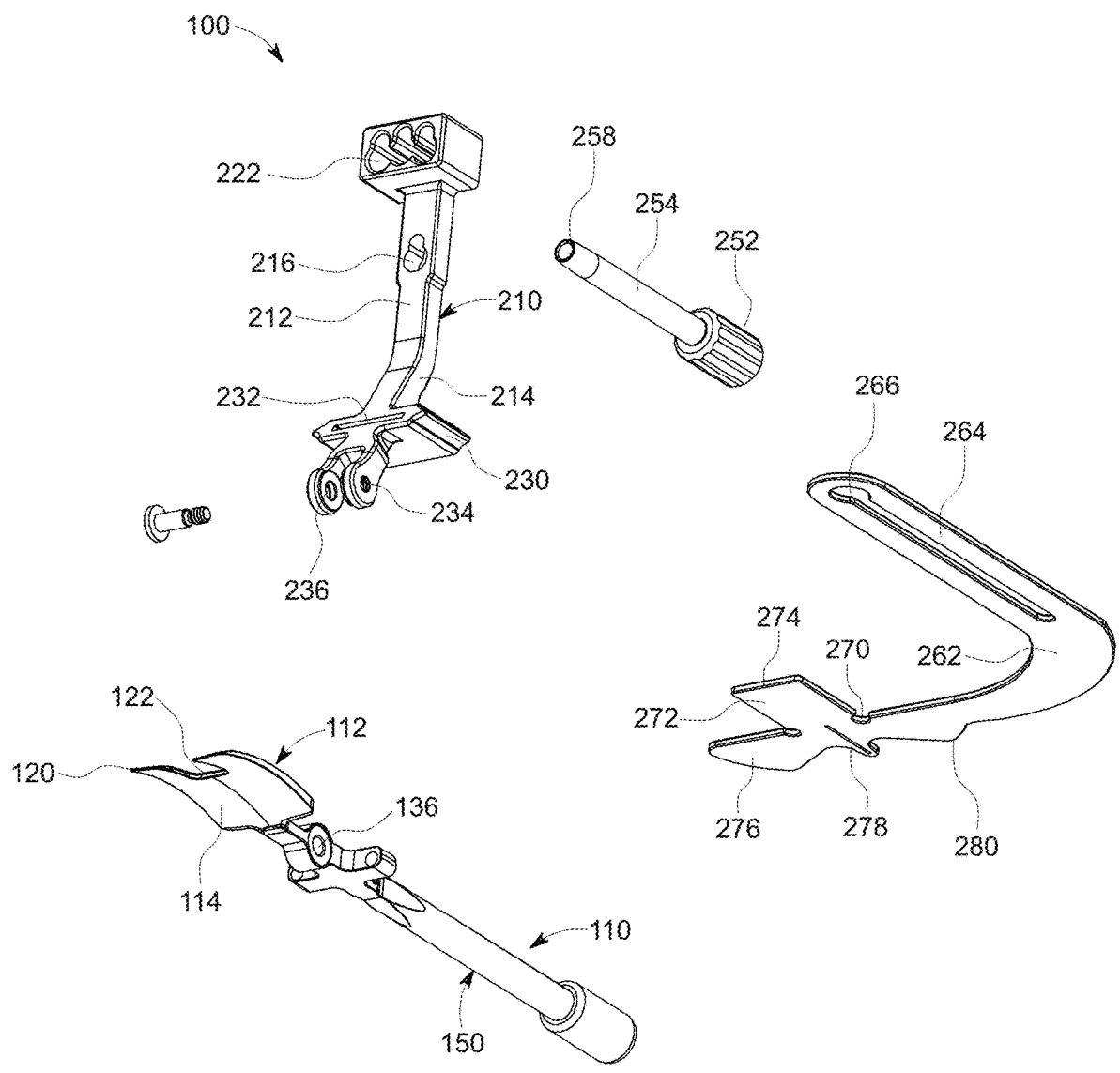
FIG. 11 is an exploded, bottom perspective view of the joint-line referencing system of FIG. 1, according to an embodiment of the present disclosure.

With reference to FIG. 8, the second portion 214 of the alignment arm 200 may include a base portion 230 having a slot 232 for receiving an auxiliary alignment instrument such as a tab 274 of the angelwing alignment member 260, or a laser alignment device (not shown), or other suitable alignment device. A distal end of the base portion 230 may further include a hinge portion with a first hinge arm or first female hinge member 234 and a spaced-apart second hinge arm or second female hinge member 234, which members have aligned hinge pin openings 236.

The pin tube guide member 250 may contain a knob 252 coupled to a first end of a shaft 254. The shaft 254 is sized for extending through one of the plurality of pin tube through-holes 222 and 216. The pin tube guide member 250 includes a passageway 256 extending through the knob 252 and the shaft 254. The second end of the shaft 254 may be, for example, tapered. The pin tube guide member 250 may be, for example, sized and shaped or configured to receive a 3.0 millimeter (mm) or other size bone-pin.

Figure 16:
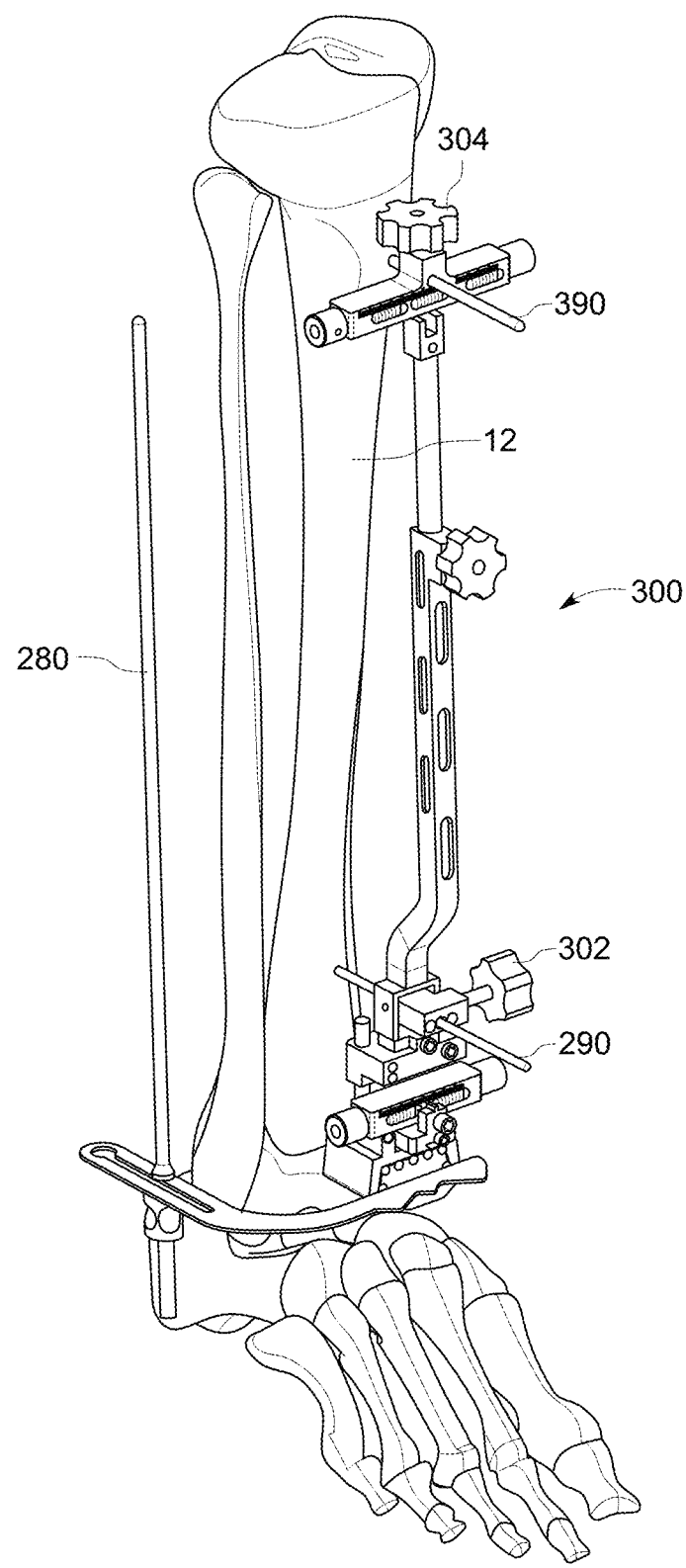
FIG. 16 is a perspective view of the patient's lower extremity and the pin of FIG. 15, and a tibia alignment guide (TAG) tower, according to an embodiment of the present disclosure.

The angelwing alignment member 260 may have a body 262. For example, the body 262 may be a planar member having an L-shaped configuration defining a first end portion 276 and a second end portion 268. The tab 274 extends from first end portion 276. The tab 274 may be, for example, sized and shaped to be received in or engage the slot 232 of the alignment arm 200. The body 262 may include cutouts 270 to assist in insertion of tab 274 into the slot 232 of the base portion 230 of the alignment arm 200. The second end portion 268 may include an elongated slot 264 with an enlarged opening for receiving and coupling to an elongate auxiliary alignment member or a rod 280 (FIG. 16).

The angelwing alignment member 260 allows a surgeon to assess the tibial slope. For example, the rod 280 may be movably coupled to the angelwing alignment member 260, such as within the slot 264 of the angelwing alignment member 260, which slot may extend anteriorly-posteriorly. The rod 280 may be oriented perpendicular (in at least one direction) or normal to the angelwing alignment member 260, and thereby perpendicular (in at least one direction) or normal to the joint line referenced by the slot 232 in base portion 230 and the angelwing alignment member 260. The rod 280 may thereby allow a user to determine/evaluate the alignment (e.g., sagittal alignment) and/or orientation (e.g., sagittal slope and/or coronal slope) of the joint line of the anatomical configuration/structures of the patient (e.g., an ankle joint) and/or of a particular implant replacing such configuration/structures (e.g., a total ankle replacement implant) implanted on/in a resected bone that is resected (at least partially).

With reference still to FIG. 8, the alignment foot 110 may include the handle 150 attached to the curved shim 112. The curved shim may include curved alignment feet 120 having spaced apart ends 118 (FIG. 1). The curved alignment feet 120 are designed to fit the talar and tibial curvature in anterior-posterior and medial-lateral directions. A portion 136 disposed between the handle 150 and the curved shim 112 may include hinge pin opening 138.

With reference again to FIGS. 4 and 5, the handle 150 is pivotally attached to alignment arm 200 with the portion 136 (FIG. 8) being positioned between hinge members 234 via a fastener pin 240 (FIG. 8) or other suitable pivoting member. The pivotable connection allows a surgeon to adjust the tibia slope. The first portion 212 of alignment arm 200 is disposed at an angle A relative to the second portion 214. The angled relationship provides an offset/clearance to allow for "negative" tibia slope. In other embodiments, the alignment arm 200 may be, for example, straight or may include a bend, curve or angulation between the first portion and the second portion. The handle 150 allows a surgeon to orient the joint-line referencing system 100 in transverse plane or internal-external rotation.

FIGS. 12-19 illustrate an alignment procedure, which includes a joint-line referencing (JLR) and the tibia alignment guide (TAG) technique for use in a TAR surgery, according to an embodiment of the present disclosure.

As shown in FIGS. 12 and 13, a surgical method includes placing the shim 112 (FIG. 1) of the alignment foot 110 into the joint 10 between the tibia 12 and the talus 14 of the patient. Specifically, the shim 112 is placed between the tibia plafond and the superior talar dome. The handle 150 may be used, for example, to position and/or orient the alignment foot 110, and thus, the coupled alignment arm 200, in a transverse plane (i.e., internal-external rotation).

Figure 14:
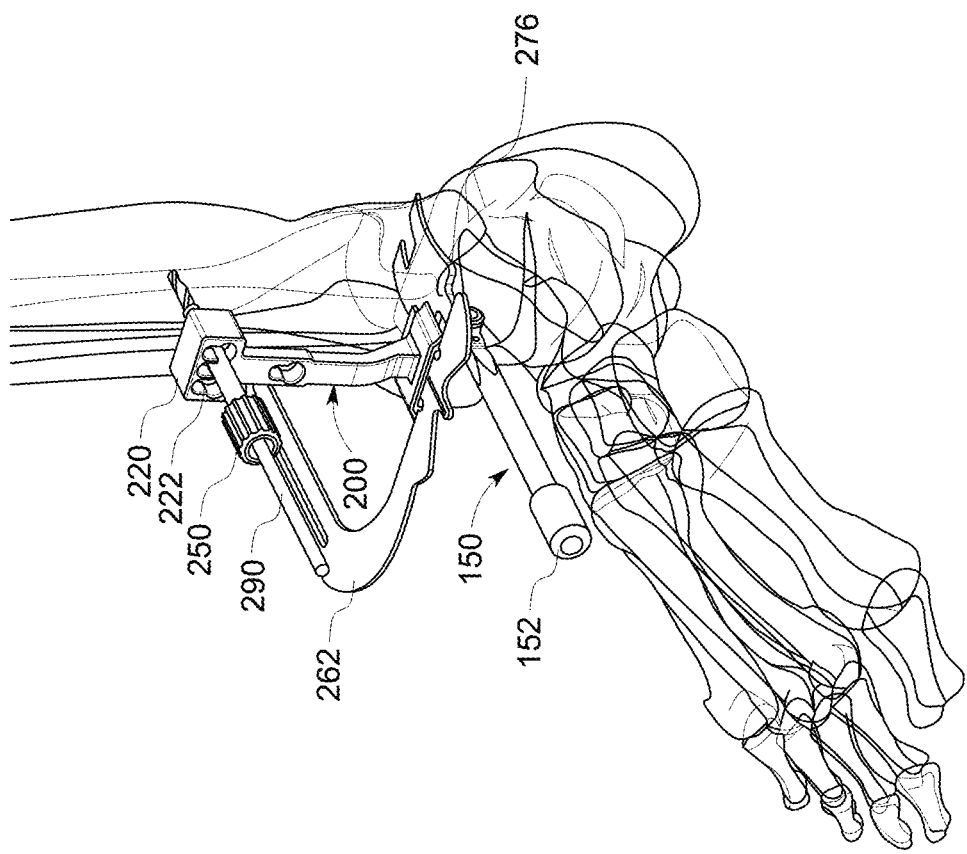
FIG. 14 is a perspective view of the joint-line referencing system of FIG. 12 and a pin attached to a patient's lower extremity, according to an embodiment of the present disclosure.

Next, the angelwing alignment member 260 is inserted into the slot 232 (FIG. 8) of the base portion 230 (FIG. 8) of the alignment arm 200 may be used by a surgeon to assess the tibial slope. As shown in FIG. 12, the joint-line referencing system 100 may be utilized and positioned and/or orientated with respect to any axis X-X of the anatomical structure of interest. After the desired position and/or orientation of the joint-line referencing system 100 is achieved, a pin 290 inserted in pin hole 256 (FIG. 8) of guide member 250 and drilled into the tibia 12, as shown in FIG. 14. The inserted pin 290 secures the selected tibial slope and internal-external rotation.

Figure 15:
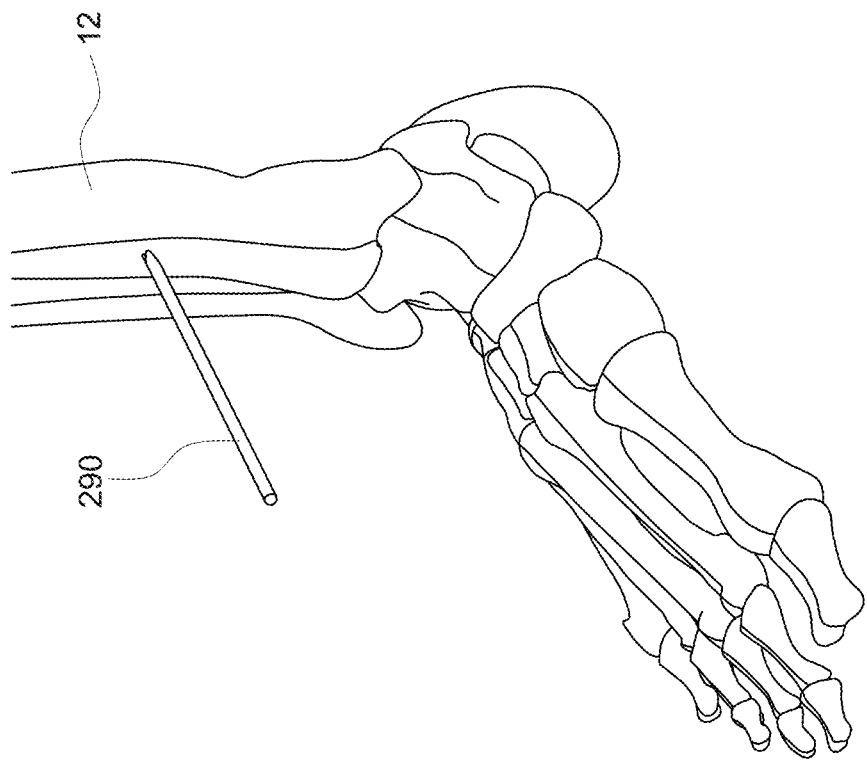
FIG. 15 is a perspective view of the patient's lower extremity with the pin attached to the patient's lower extremity after removal of the joint-line referencing system of FIG. 12, according to an embodiment of the present disclosure.

With reference to FIG. 15, the joint line referencing system 100 (FIG. 14) may be removed, whereby the pin 290 remains inserted into the tibia 12. For example, the pin tube guide member 250 (FIG. 14) may be removed, and simultaneously the alignment arm 200 (FIG. 14) may be simultaneously removed from the pin 290 and the shim 112 (FIG. 1) removed from the joint. The irregular shaped pin tube through-holes 222 allow for movement and removal of the joint-line reference system 100. The pin 290 serves as the starting point for the next portion of the surgical procedure, i.e., the TAG technique.

As shown in FIG. 16, a second pin 390 may then be drilled into the proximal tibial tubercle to support the TAG tower 300 on the pins 290 and 390, and with the TAG tower 300 aligned on the patient's tibia 12.

Figure 17:
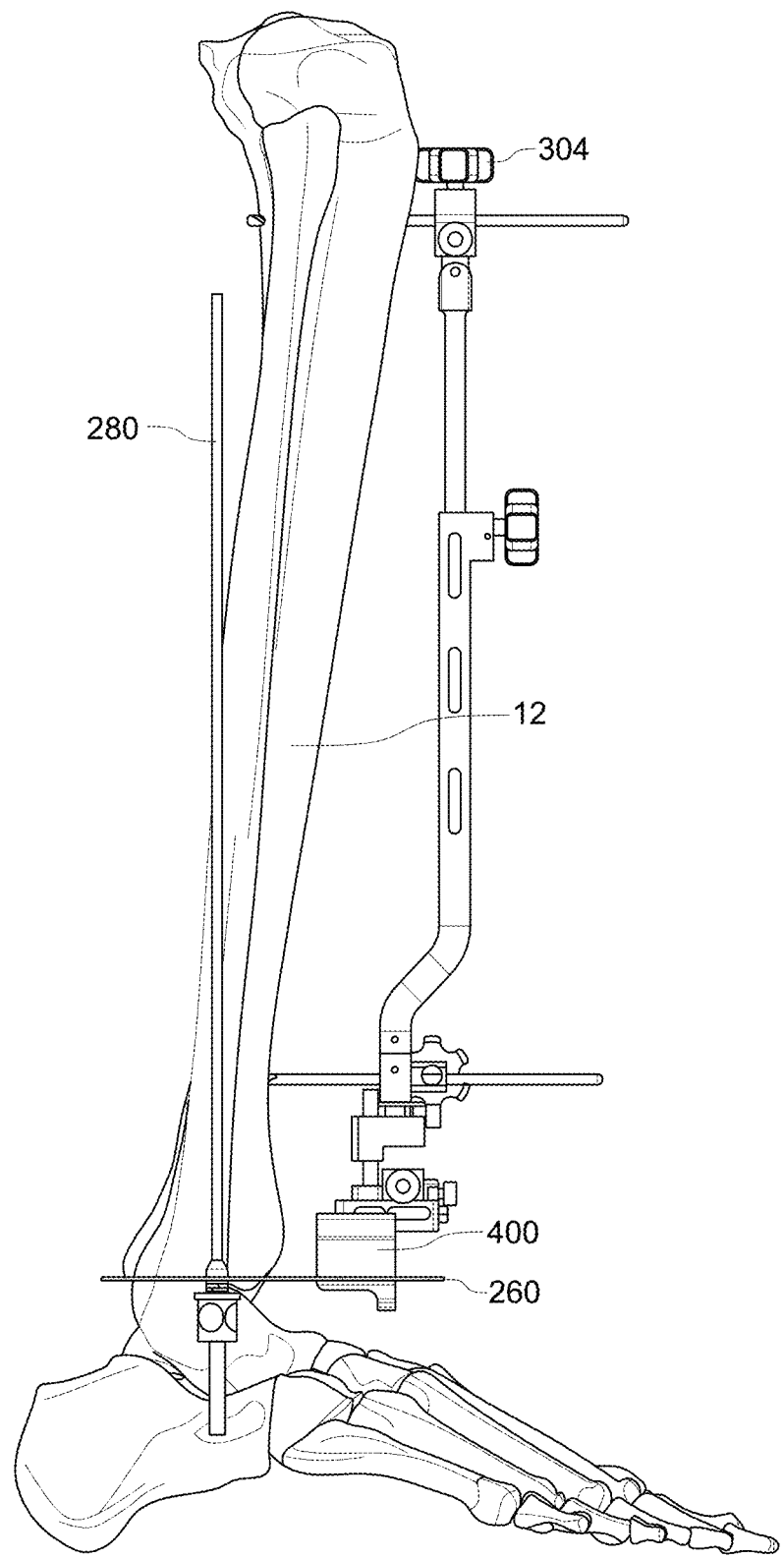
FIG. 17 is a side elevational view of the lower extremity, the pin, and the TAG tower of FIG. 16, according to an embodiment of the present disclosure.
Figure 19:
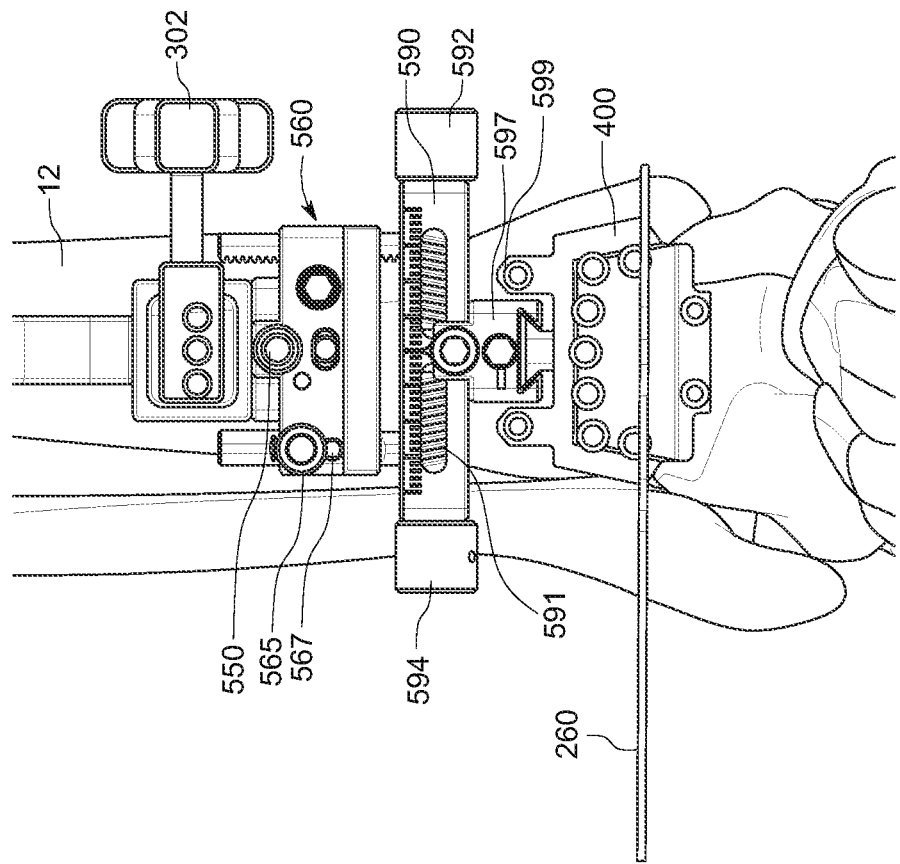
FIG. 19 is an enlarged, front elevational view of the distal portion of the patient's lower extremity and the TAG tower of FIG. 16, according to an embodiment of the present disclosure.
Figure 18:
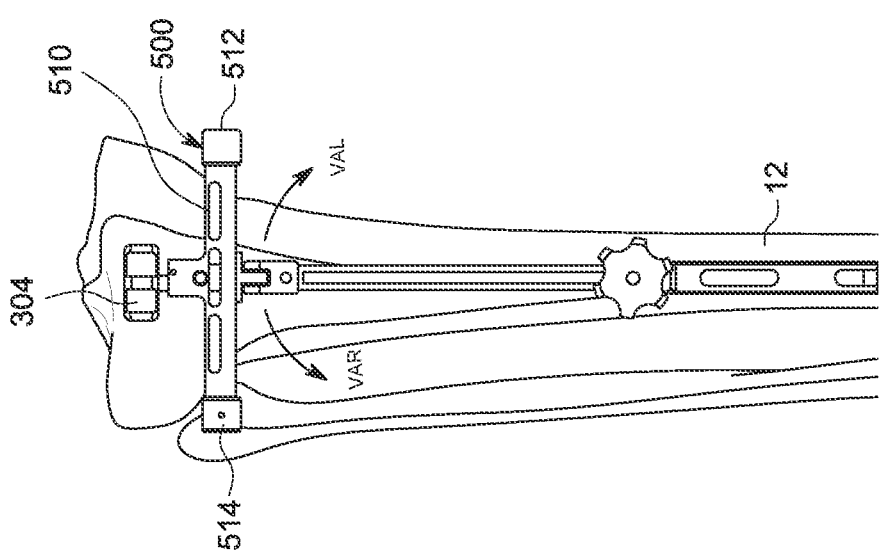
FIG. 18 is an enlarged, front elevational view of the proximal portion of the patient's lower extremity and the TAG tower of FIG. 16, according to an embodiment of the present disclosure.

Next, as shown in FIGS. 17-19, a surgeon may align the tibial slope. The surgeon may use an alignment method of their choice, for example, (1) use gap or "finger-breadths" at the proximal and distal ends, (2) use the angelwing alignment member 260 to align with the distal tibia and ankle joint, or (3) use the lateral rod 280 (FIG. 17) aligned to the tibial axis. In an embodiment, to begin the alignment of the tibial slope, a tibial sizing template 400 may be coupled to the distal end of the TAG tower 300 using a locking-cam screw. Thereafter, a first knob 302 and a second knob 304 are tightened to lock the TAG tower 300 to the pins 290 and 390, and thus, to the patient's tibia 12.

Next, as shown in FIG. 18, a varus-valgus alignment may be performed. For example, the varus-valgus alignment may be performed using a varus-valgus alignment housing or double-lead screw housing 500. The housing 500 may include a double-lead screw 510. The double-lead screw housing 500 allows the user to adjust varus-valgus alignment by allowing for rotation about the screw 510. For example, the rotation is achieved by turning the knobs 512 and 514 positioned at the medial and lateral sides of the screw 510.

Optionally, as shown in FIG. 19, an internal-external rotation locking screw 550 may be loosened to allow for internal-external rotation adjustment of the TAG tower 300. The TAG tower 300 may include, for example, indicators to allow the user to easily determine whether the tower 300 is internally or externally rotated or if the TAG tower 300 is positioned at neutral.

The TAG tower 500 may also include a rack-and-pinion gear box 560. The rack- and pinion gear box 560 allows for adjustment of a distal-proximate position of a sizing template 400. Once the desired distal-proximal position is achieved, a ball-plunger 565 and locking screw 567 may, for example, provide friction and lock the position of the rack-and pinion gear box 560.

The distal end of the TAG tower 300 may also include a second or distal varus-valgus alignment housing or double-lead screw housing 590. The second housing 590 allows for medial-lateral position adjustments. The second housing 590 may include, for example, a double-lead screw 591 positioned along the longitudinal axis of the second housing 590. The second housing 590 may also include two knobs 592 and 594 for translating the coupling member 597 in the medial-lateral direction. After the desired medial-lateral alignment is achieved, a locking screw or locking cam screw 599 may be used to fix the medial-lateral position of the attached sizing template 400. The adjustment steps may use radiographic markers on the sizing template to properly size, align and position the instruments. Suitable alignment systems and sizing templates are described in international patent application PCT/US2019/029978, filed May 1, 2019, and entitled "Laser-Based Implant Alignment And Resection Guide Systems And Related Methods," the entire contents being incorporated in herein by reference.

FIGS. 20-24 illustrate a joint-line referencing system 101, according to an embodiment of the present disclosure. For example, in some embodiments, the joint-line referencing system 101 may be operable with a fast-track alignment system 600 (FIG. 27) as described in greater detail below. In this illustrated embodiment, the joint-line referencing system 101 may be essentially the same as the joint-line referencing system 100 (FIGS. 1-11) having, for example, the alignment arm 200, the first pin tube guide member 250, the angelwing alignment member 260, the alignment foot 110 having the handle 150 and the curved shim 112 as described above, but with the exception of a second pin tube guide member 251.

FIG. 25-30 illustrate an alignment procedure, which includes a joint-line referencing and a fast-track alignment technique for use in a TAR surgery, according to an embodiment of the present disclosure. The method of using the joint-line referencing system for this technique is similar to the joint-line referencing system to TAG technique, except that an additional or second 3.0 mm pin is drilled into the distal tibia of the patient. As will be appreciated, the second pin takes the place of the proximal pin used in the TAG technique.

Figure 25:
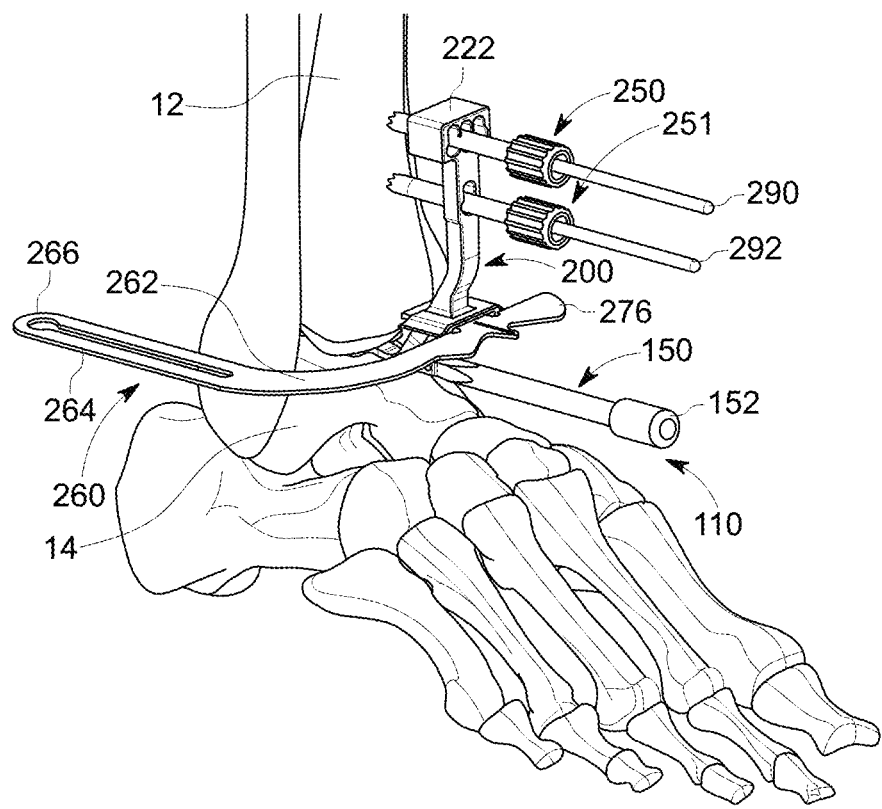
FIG. 25 is a perspective view of the joint-line referencing system of FIG. 20 and pins attached to a patient's lower extremity, according to an embodiment of the present disclosure.

As shown in FIG. 25, the surgical method includes placing the shim 112 (FIG. 21) of the alignment foot 150 into the joint between the tibia 12 and the talus 14 of the patient. Specifically, the shim is placed between the tibia plafond and the superior talar dome. The handle 150 may be used, for example, to position and/or orient the alignment foot 110, and thus, the coupled alignment arm 200, in the transverse plane (i.e., internal-external rotation).

Next, the angelwing alignment member 260 is inserted into the slot 232 (FIG. 8) of the base portion 230 (FIG. 8) and used by a surgeon to assess the tibial slope. The joint-line referencing system may be utilized and positioned and/or orientated with respect to any axis of the anatomical structure of interest. After the desired orientation of the joint-line referencing system 101 is achieved, a first pin 290 is inserted in pin hole 256 (FIG. 20) of the first pint tube guide member 250 and drilled into the tibia 12, and then a second pin 292 is inserted in a pin hole 257 (FIG. 21) of the second pin tube guide member 251 and drilled into the tibia 12 as shown in FIG. 25. The inserted pins 290 sand 292 secure the selected tibial slope and internal-external rotation. As noted above, the irregular shaped pin tube through-holes 222 (FIG. 21) in the pin tube holder 220 (FIG. 21) and the pin tube through-holes 216 (FIG. 21) accommodate leaving the pins 290 and 292 in the patient's tibia upon removing the joint-line referencing system 101.

Figure 26:
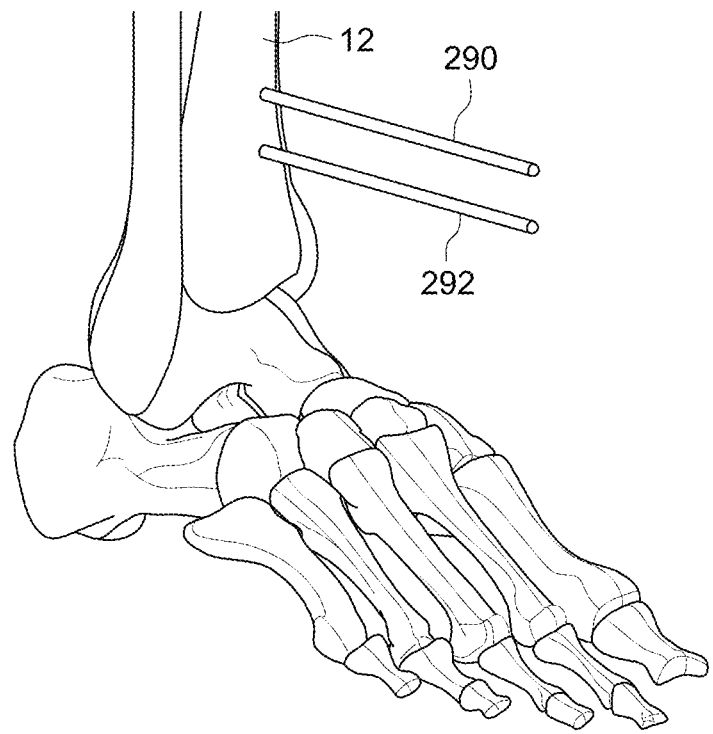
FIG. 26 is a perspective view of the patient's lower extremity with the pins attached to the patient's lower extremity after removal of the joint-line referencing system of FIG. 20, according to an embodiment of the present disclosure.
Figure 27:
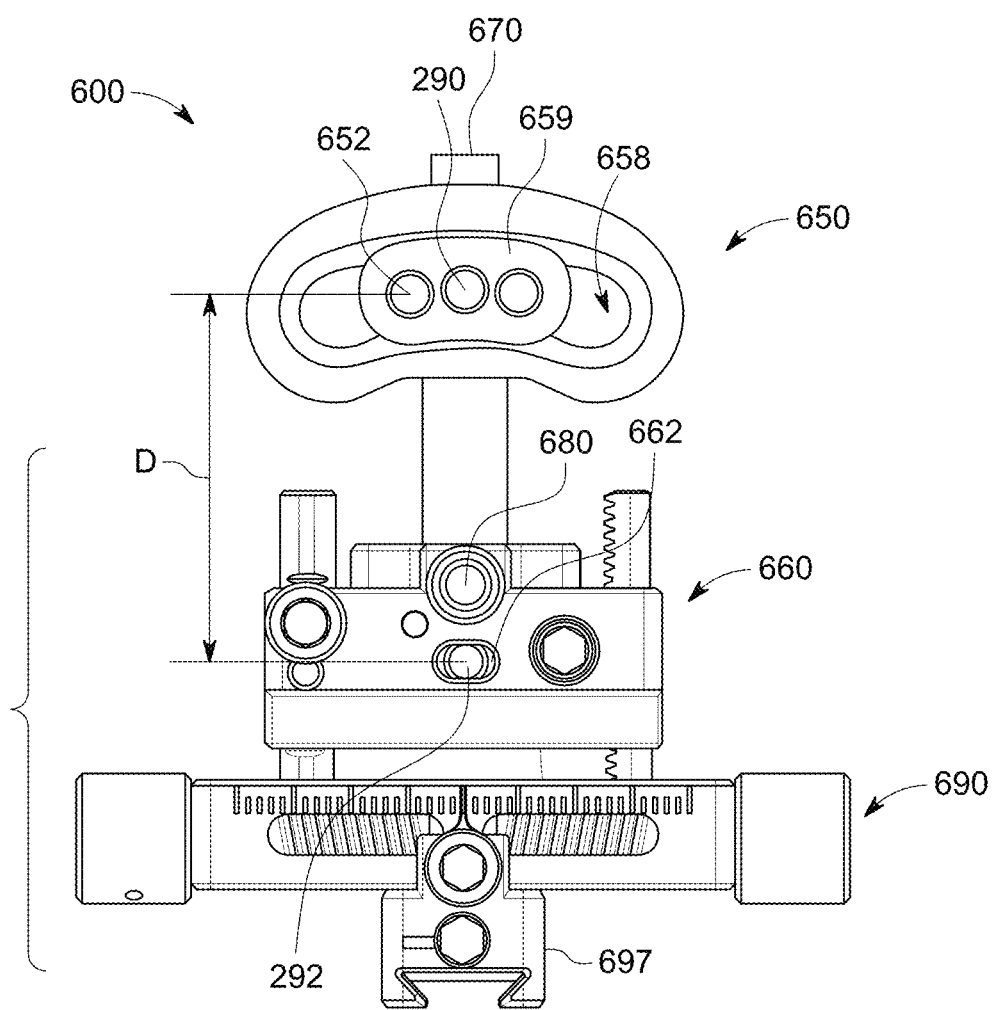
FIG. 27 is a front view of a fast-track alignment system, according to an embodiment of the present disclosure.

With reference to FIG. 26, the joint line referencing system 101 may be removed, whereby the pins 290 and 292 remain inserted into the tibia 12 of the patient. For example, the pin tube guide members 250 (FIG. 25) may be removed, and simultaneously the alignment arm 200 may be removed from the pins 290, 292 and the shim 112 (FIG. 21) removed from the joint. These two pins are the starting point for the supporting the fast-track alignment system 600 (FIG. 27). For example, the pins 290 and 292 serve as the starting point for the next portion of the surgical procedure, i.e., the fast-track technique.

FIG. 27 illustrates the fast-track alignment system 600 according to an embodiment of the present disclosure. In this illustrated embodiment, the fast-track alignment system 600 may include a rack-and-pinion gear box 660, a distal varus-valgus alignment housing or double-lead screw housing 690, and a coupling member 697. The rack-and-pinion gear box 660, the distal varus-valgus alignment housing or double-lead screw housing 690, and the coupling member 697 may be the same or essentially the same as the rack-and-pinion gear box, the distal varus-valgus alignment housing or double-lead screw housing, and the coupling member as described above in connection with the TAG tower 300 (FIG. 16). For example, in some embodiments, this portion of the fast-track alignment system may be reused from the TAG tower 300 (FIG. 16).

Figure 28:
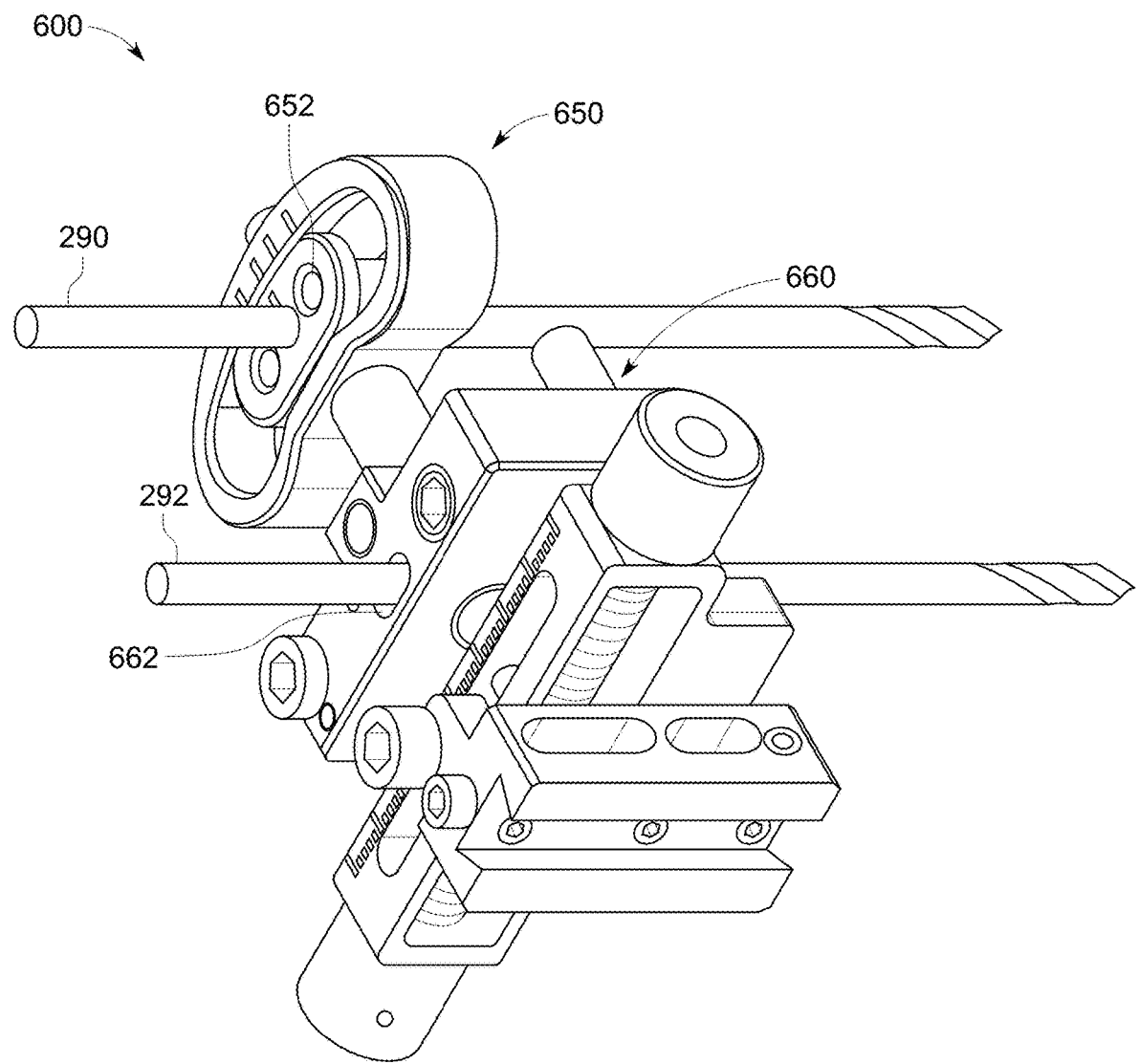
FIG. 28 is a bottom perspective view of the fast-track alignment system of FIG. 27, according to an embodiment of the present disclosure.

As shown in FIG. 28, the rack-and-pinion gear box 660 may include a pin hole 662 extending therethrough and in which the pin 292 may extend. With reference again to FIGS. 27 and 28, a distal portion 650 of the fast-track alignment system 600 may be modular and operably attachable to the distal portion the rack-and-pinion gear-box 660 using, for example, a quarter-turn mechanism. The distal portion 650 may include a curved channel 658 (FIG. 27) in which is operably retained a sliding member 659 (FIG. 27) having pin-holes 652 within a 3-hole pattern which holes 652 are similarly or identically distanced a distance D from the pin-hole 662 through the rack-and-pinion gear-box 660.

The pin-hole 662 may be a circular or an elongated hole. The distance D may match that of the joint-line reference shim.

Figure 29:
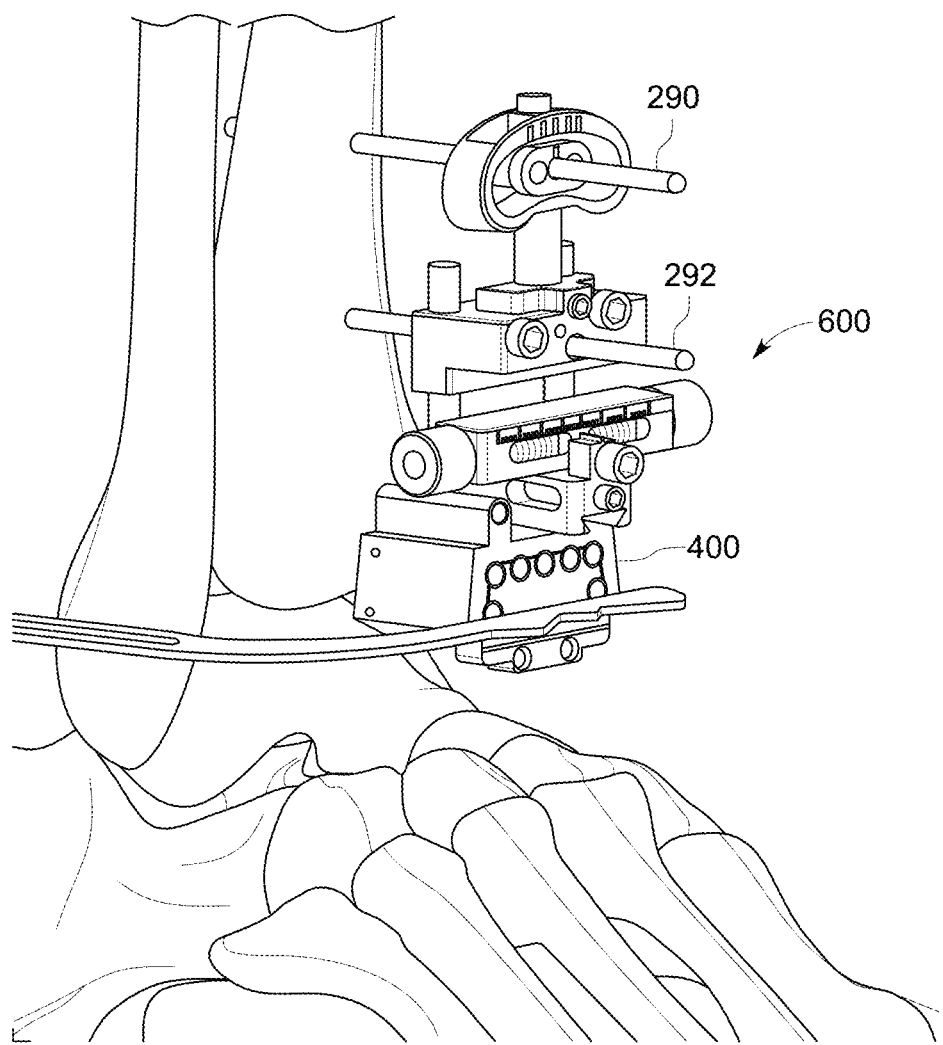
FIG. 29 is a perspective view of the fast-track alignment system of FIG. 27 positioned on a patient's lower extremity with a sizing block coupled to the distal end of the fast-track alignment system and an angelwing alignment member coupled to the sizing block, according to an embodiment of the present disclosure.
Figure 30:
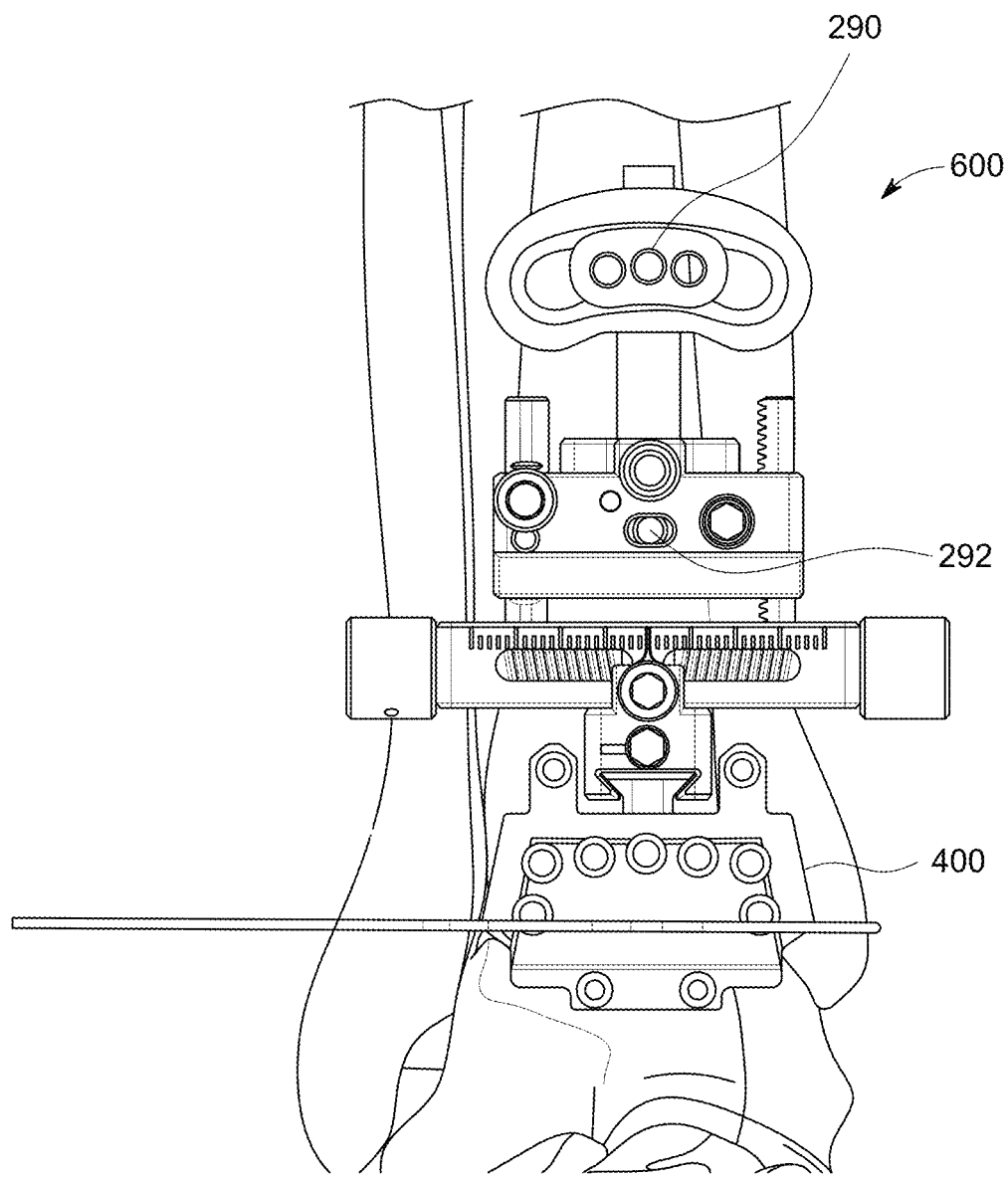
FIG. 30 is an enlarged, front view of the fast-track alignment system of FIG. 29 and the patient's lower extremity, according to an embodiment of the present disclosure.

With reference to FIGS. 29 and 30, the fast-track alignment system 600 is slid over the two 3.0 mm bone pins 290 and 292. The tibial slope is defined/locked by the angle/direction of these pins. When the sizing block 400 is attached to the fast-track reference system 600 the sizing block is properly placed against the bone, a pin-locking knob may be tightened. The varus-valgus alignment is adjusted by loosening the locking screw 670 (FIG. 27). The pin-hole 662 in the rack-and-pinion gear-box 660 aligns over the distal pin 292. This allows the user to adjust internal-external rotation by loosening an internal-external rotation locking screw 680 (FIG. 27). The distal-proximal and medial-lateral adjustments are made similarly to the TAG method described above.

With reference now to FIG. 31-36, therein illustrated is a joint line pointer 1000 for adjusting an alignment guide or alignment system, according to an embodiment of the present disclosure. For example, the joint line pointer 1000 may be employed for generally setting internal and external rotation of the alignment guide such as a fast-track alignment system 900. Additional alignment devices may include the angelwing alignment member 260, and a medial gutter tool 2000.

Figure 31:
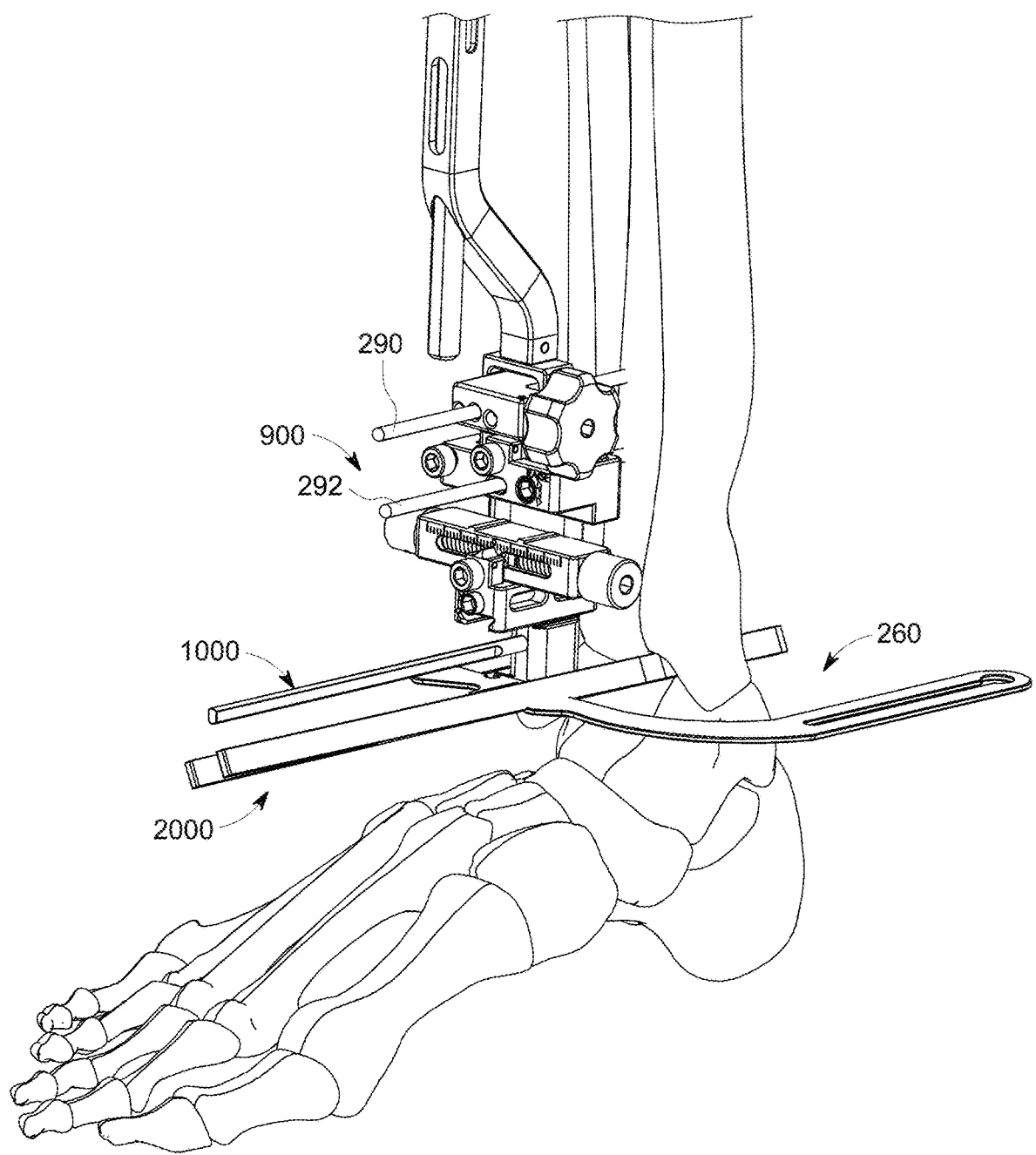
FIG. 31 is a perspective view of a fast-track alignment system and a joint line pointer positioned on a patient's lower extremity, according to an embodiment of the present disclosure.
Figure 32:
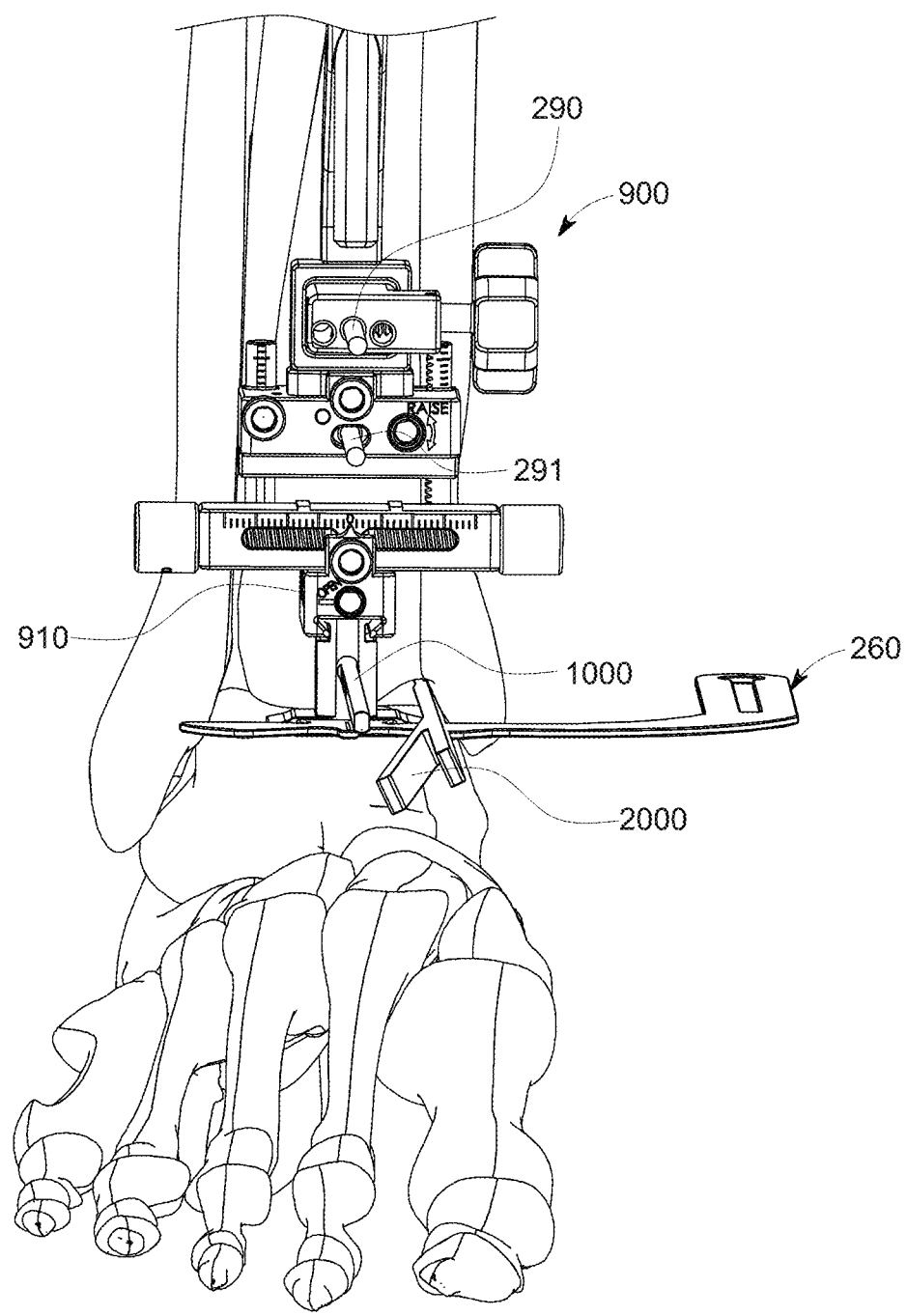
FIG. 32 is a front elevational view of the fast-track alignment system and the joint line pointer of FIG. 31, according to an embodiment of the present disclosure.
Figure 33:
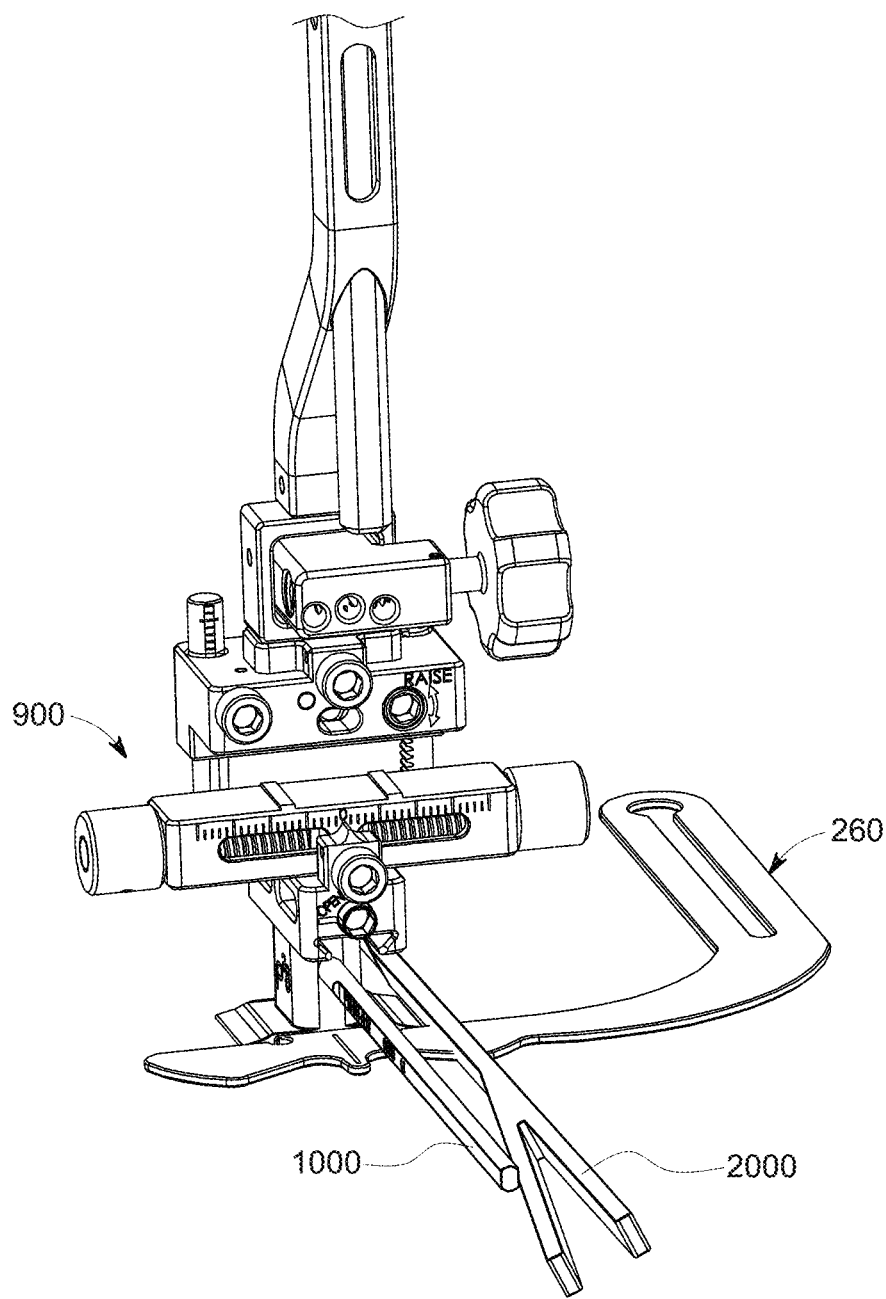
FIG. 33 is a perspective view of the fast-track alignment system and the joint line pointer of FIG. 31, according to an embodiment of the present disclosure.
Figure 34:
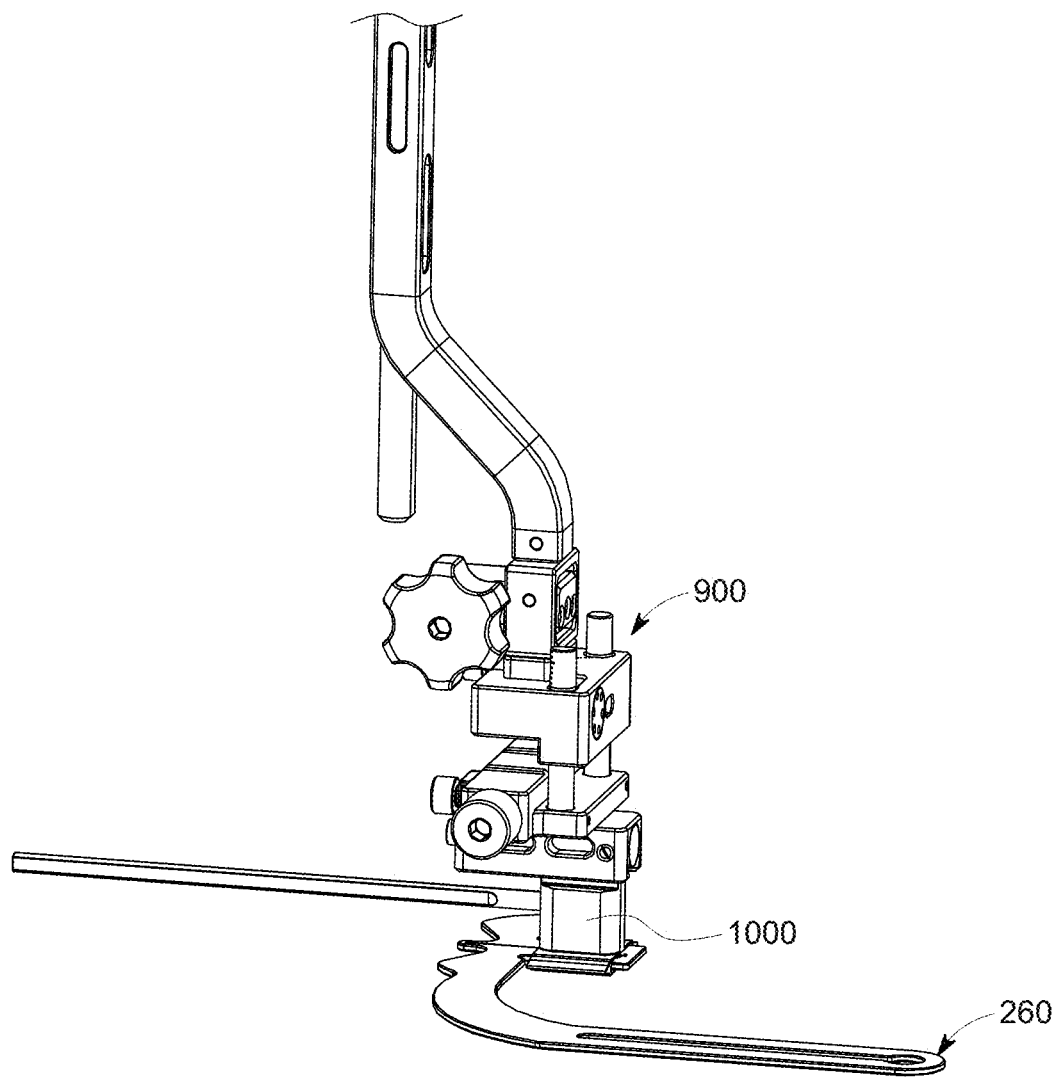
FIG. 34 is a perspective view of the fast-track alignment system and the joint line pointer of FIG. 31, according to an embodiment of the present disclosure.
Figure 35:
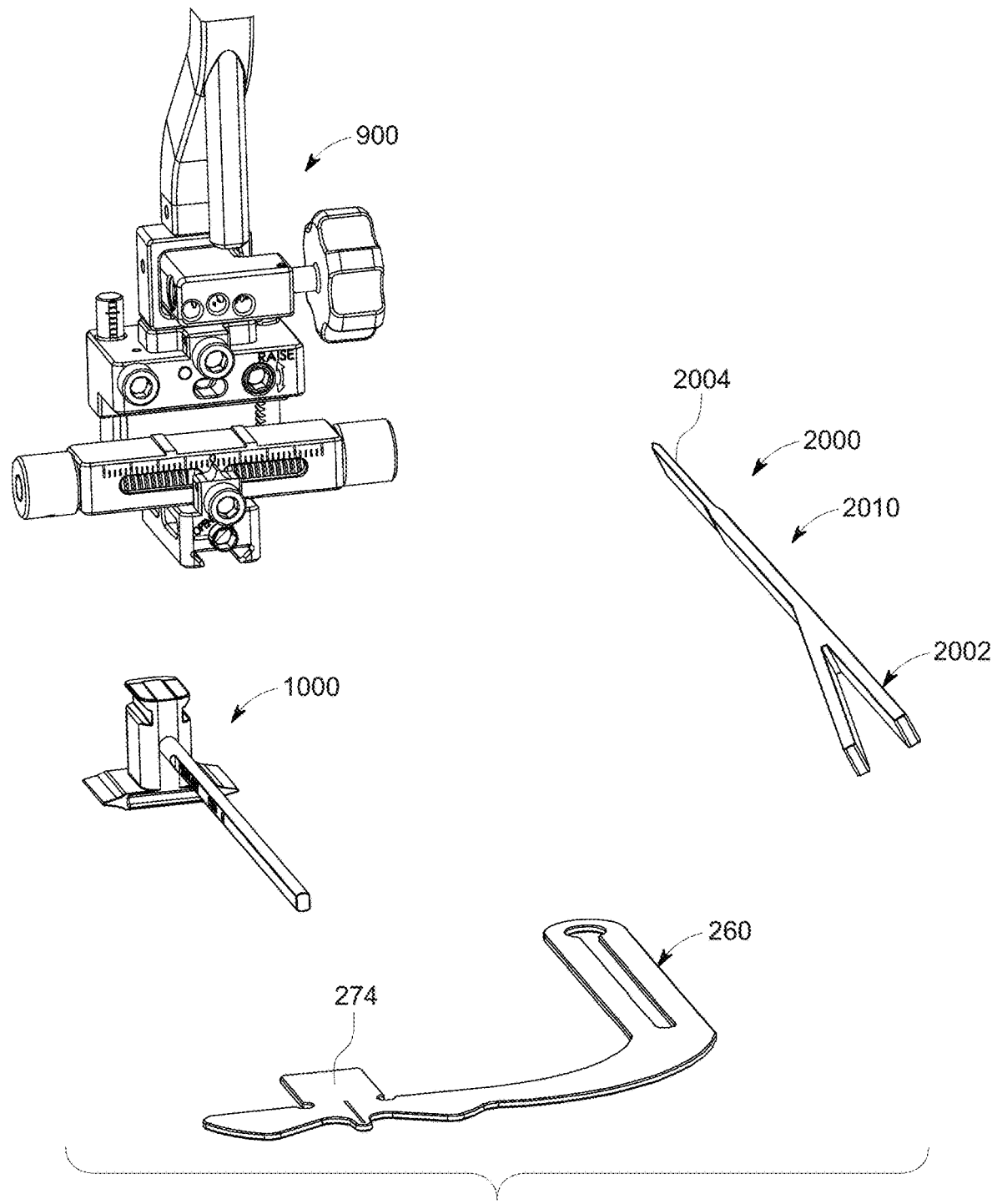
FIG. 35 is an exploded, top perspective view of the fast-track alignment system and the joint line pointer of FIG. 31, according to an embodiment of the present disclosure.
Figure 36:
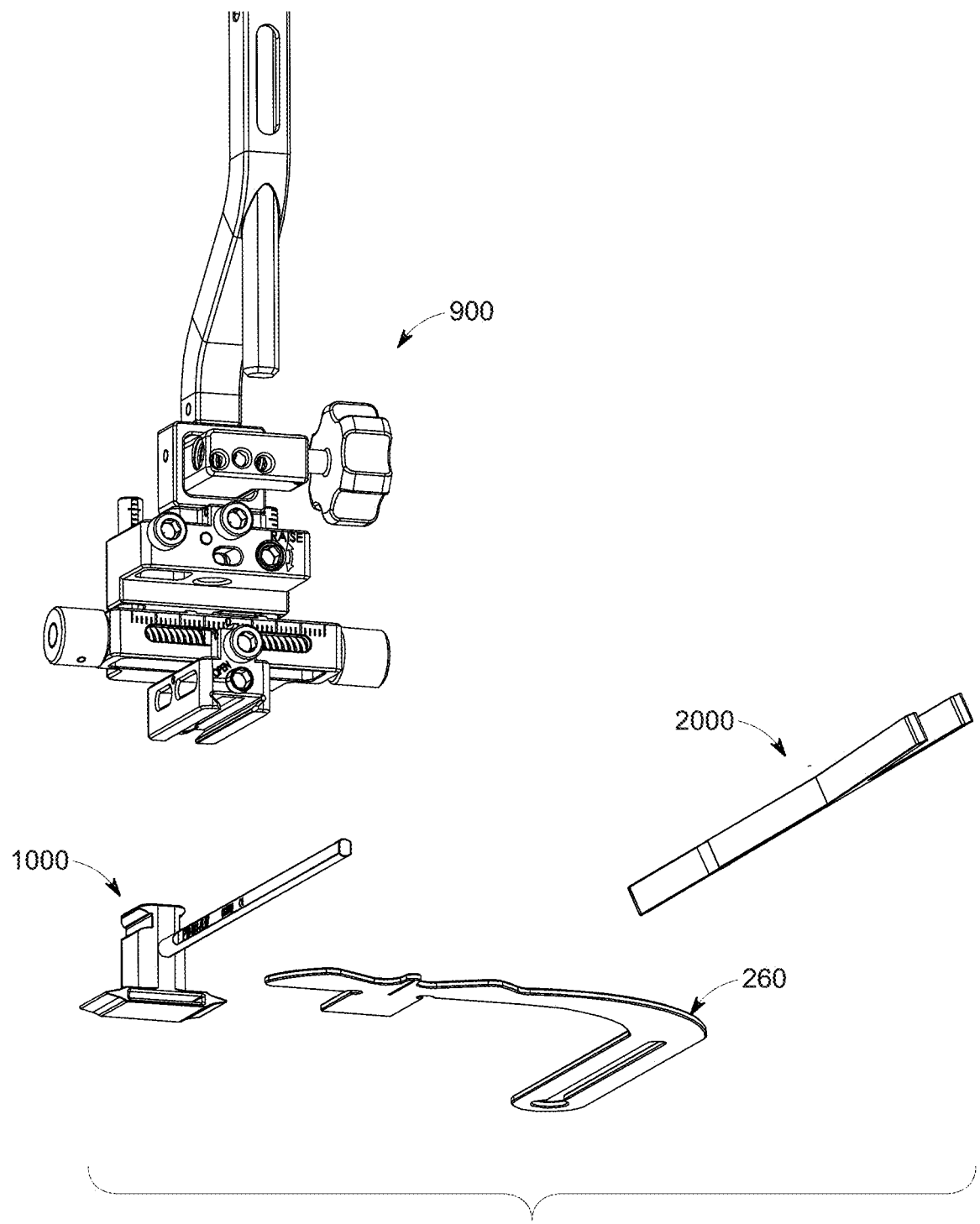
FIG. 36 is an exploded, bottom perspective view of the fast-track alignment system and the joint line pointer of FIG. 31, according to an embodiment of the present disclosure.

As shown in FIGS. 31 and 32, the fast-track alignment system 900 may be positioned on pins 290 and 292 installed using the joint-line referencing system 101 (FIG. 20) described above, or the joint-line referencing system 4000 (FIG. 45) described below. The fast-track alignment system 900 may include a first translation mechanism or medial lateral adjustment member, a second translation mechanism or distal proximal adjustment member, and third translation mechanism or varus-valgus adjustment member, similar to the adjustment member and systems described above with the fast-track alignment system 600 (FIG. 27).

Figure 37:
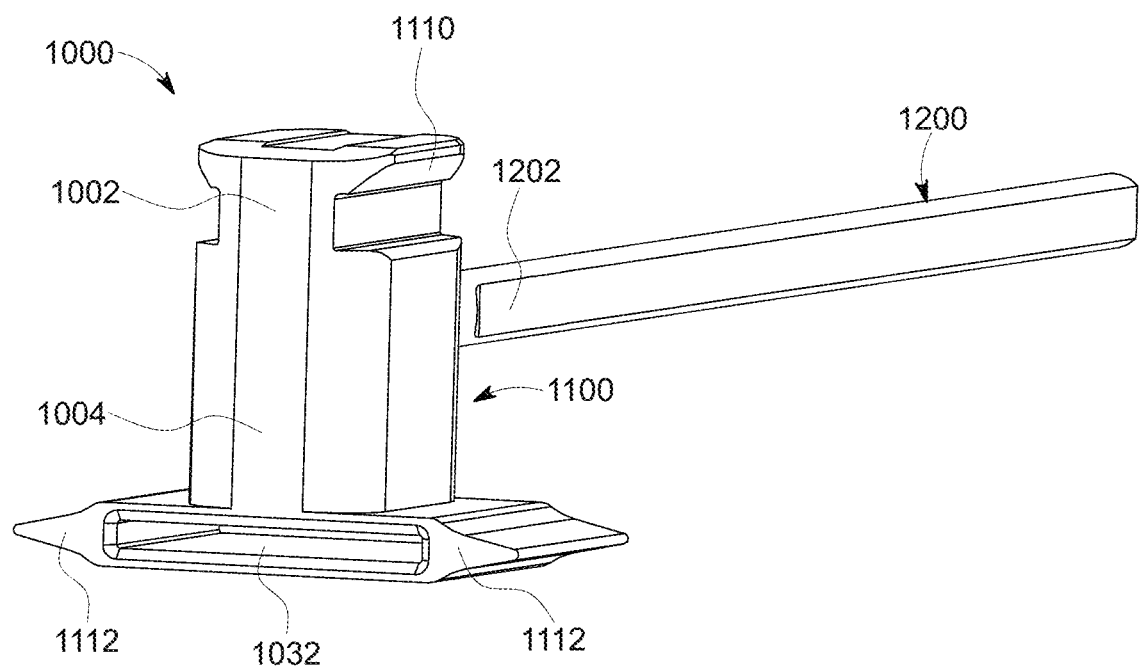
FIG. 37 is a perspective view of the joint line pointer of FIG. 31, according to an embodiment of the present disclosure.
Figure 38:
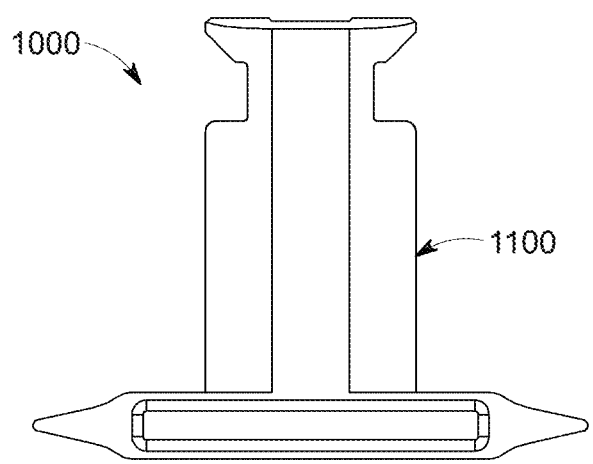
FIG. 38 is a front elevational view of the joint line pointer of FIG. 37, according to an embodiment of the present disclosure.
Figure 39:
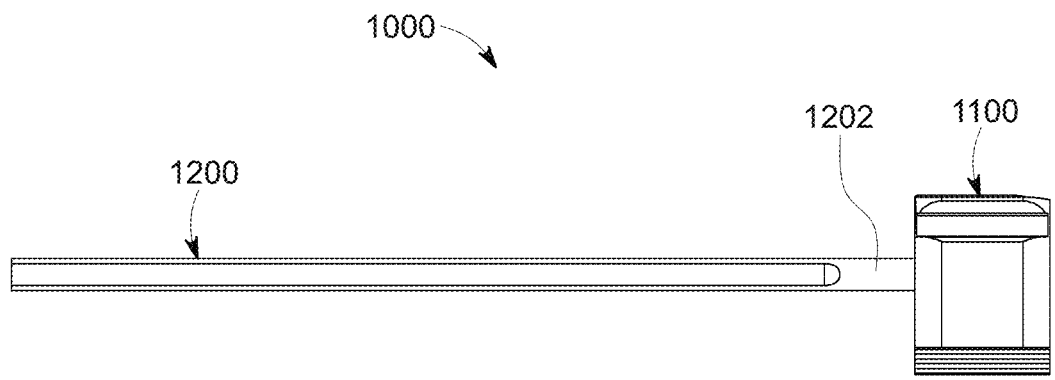
FIG. 39 is a side elevational view of the joint line pointer of FIG. 37, according to an embodiment of the present disclosure.
Figure 40:
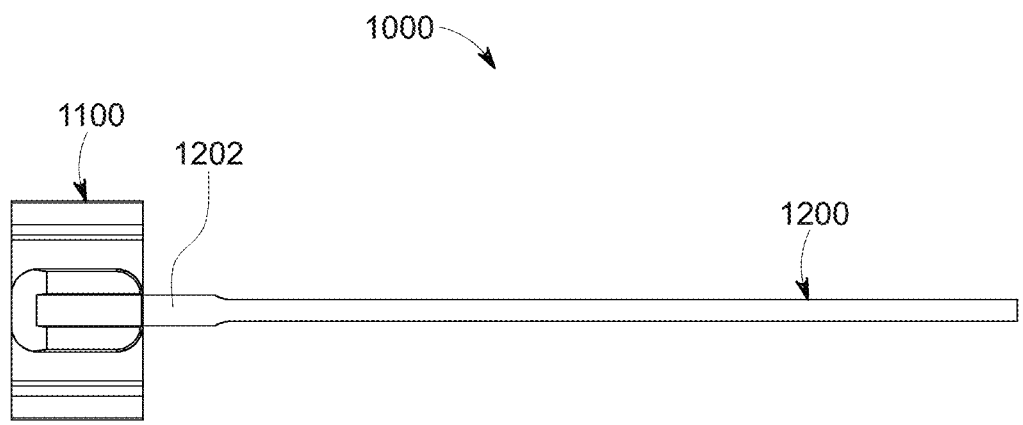
FIG. 40 is a top view of the joint line pointer of FIG. 37, according to an embodiment of the present disclosure.

As shown in FIGS. 37-40, the joint line pointer 1000 may generally include a body 1100 and a handle 1200 having one end 1202 attached to body 1100. With reference to FIG. 37, body 1000 may include an upper portion 1002 and lower portion 1004. The upper portion 1002 may include a coupling member 1110 that is receivable in the coupling member 910 (FIG. 32) of the fast-track alignment system 900 (FIG. 32). The lower portion 1004 includes a slot 1032 for receiving a tab 274 (FIG. 35) of the angelwing alignment member 260 (FIG. 35) and laterally-extending portions 1112 for assessing the joint line.

Figure 41:
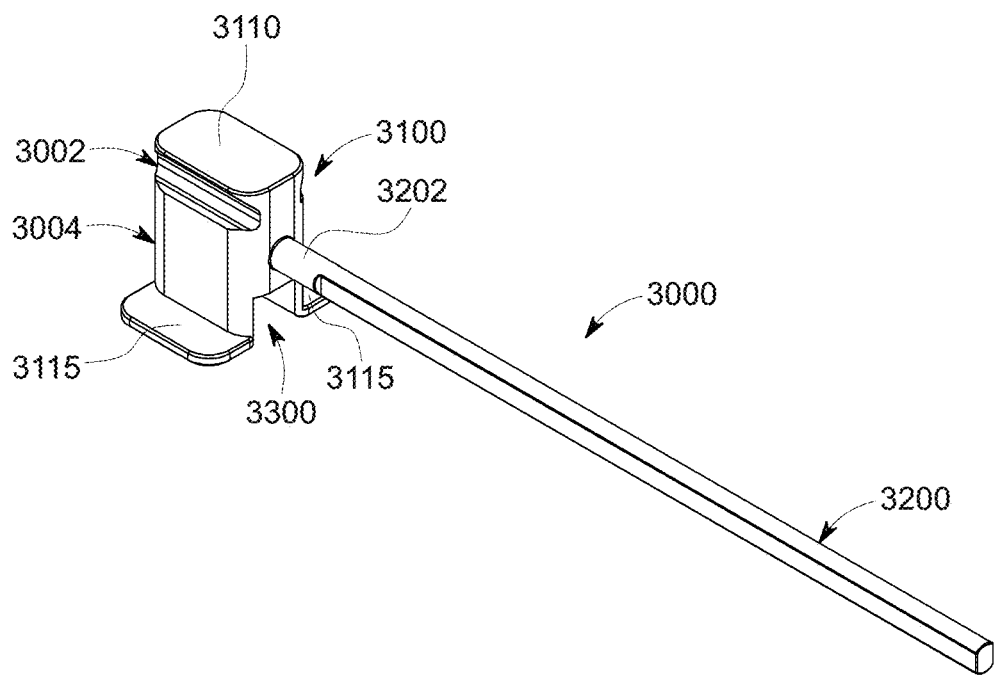
FIG. 41 is a perspective view of a joint line pointer, according to an embodiment of the present disclosure.
Figure 42:
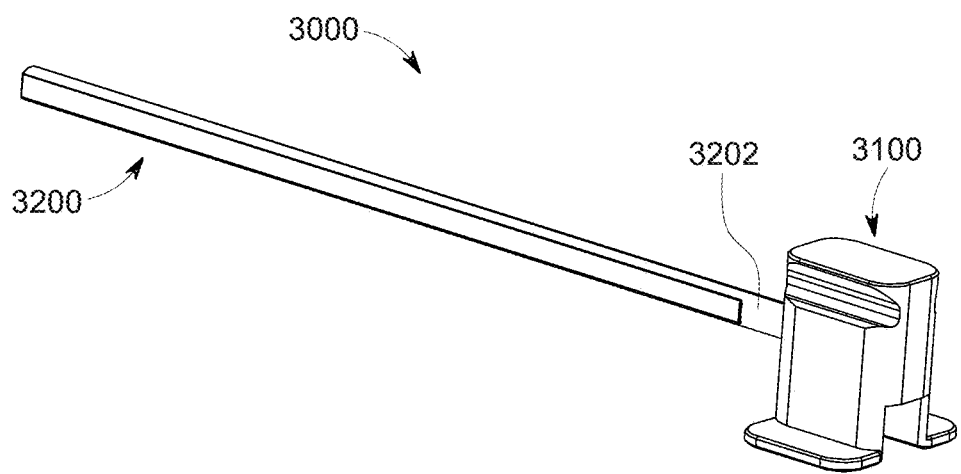
FIG. 42 is a perspective view of the joint line pointer of FIG. 41, according to an embodiment of the present disclosure.
Figure 43:
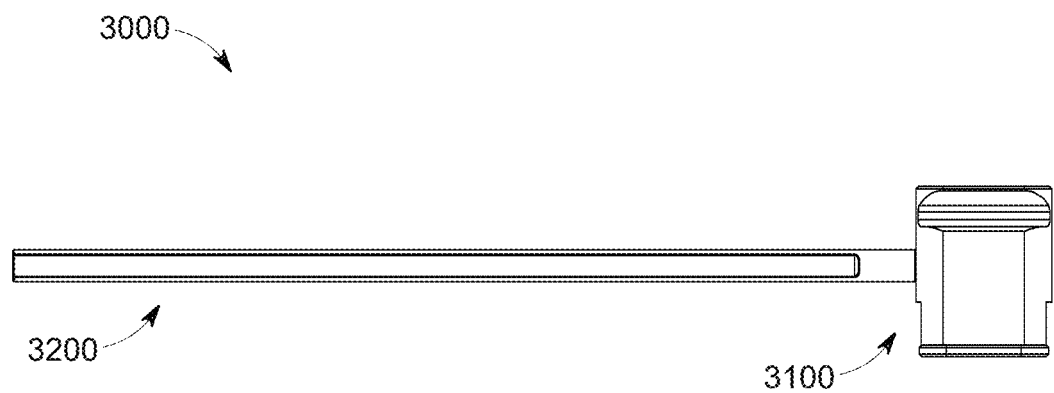
FIG. 43 is a side elevational view of the joint line pointer of FIG. 41, according to an embodiment of the present disclosure.
Figure 44:
FIG. 44 is a top view of the joint line pointer of FIG. 41, according to an embodiment of the present disclosure.

FIGS. 41-44 illustrates another joint line pointer 3000, according to an embodiment of the present disclosure. In this illustrated embodiment, the joint line pointer 3000 may generally include a body 3100 and a handle 3200 having one end 3202 attached to body 3100. As shown in FIG. 41, the body 3000 may include an upper portion 3002 and lower portion 3004. The upper portion 3002 may include a coupling member 3110 that is receivable in the coupling member 910 (FIG. 32) of the fast-track alignment system 900 (FIG. 32). The lower portion 3004 includes a through opening 3300 and laterally-extending feet 3115. The feet extended medially and laterally to indicate the joint line.

With reference again to FIG. 35, the medial gutter tool 2000 may having an elongated body 2010 having a first portion 2002 and a second portion 2004. The first portion 2002 may be Y-shaped, and the second portion 2004 may be a reduced or tapered distal end.

With reference again to FIG. 31, once the fast-track alignment system 900 is positioned on the pins 290 and 292, the joint line pointer such as the joint line pointer 1000 (or the joint line pointer 3000 (FIG. 41)), and the medial gutter tool 2000 may be operably employed by a surgeon to move and align the fast-track alignment system 900 in proper orientation relative to the lower extremity of the patient. The medial gutter tool 2000 may be used along the medial gutter plane or to a determined gutter bisection. Once in proper alignment, position, and orientation, the fast-track alignment system may be operably lockably secured in place on the pins attached to the lower extremity of the patient's tibia. The joint line pointer and gutter tool may be used with the any of the above TAR and fast-track alignment systems.

The above alignment systems, e.g., TAG and fast-track alignment systems, joint line pointers, and gutter tools may be operably usable with suitable resection guides and other tools for performing total ankle replacement. For example, the above alignment systems may be operable with the resection guides described in U.S. provisional patent application No. 62/898,615, filed Sep. 11, 2019, and entitled "Resection Guides, Sweeping Reamers, And Methods For Use In Total Ankle Replacement", the entire contents being incorporated in herein by reference. Other suitable fast-track alignment system may be used with the joint-line reference systems of the present disclosure. For example, suitable fast-track alignment systems are described in U.S. Provisional Application No. 62/899,703 filed Sep. 11, 2019, entitled "Joint Replacement Alignment Guides, Systems And Methods Of Use And Assembly"), which is hereby incorporated by reference in its entirety. Other suitable tibial alignment guide system may be used with the joint-line reference systems of the present disclosure. For example, suitable tibial alignment guide systems are described in U.S. Provisional Application No. 62/899,740, filed Sep. 12, 2019, entitled "Joint Replacement Alignment Guides, Systems And Methods Of Use And Assembly", which is hereby incorporated by reference in its entirety.

Figure 45:
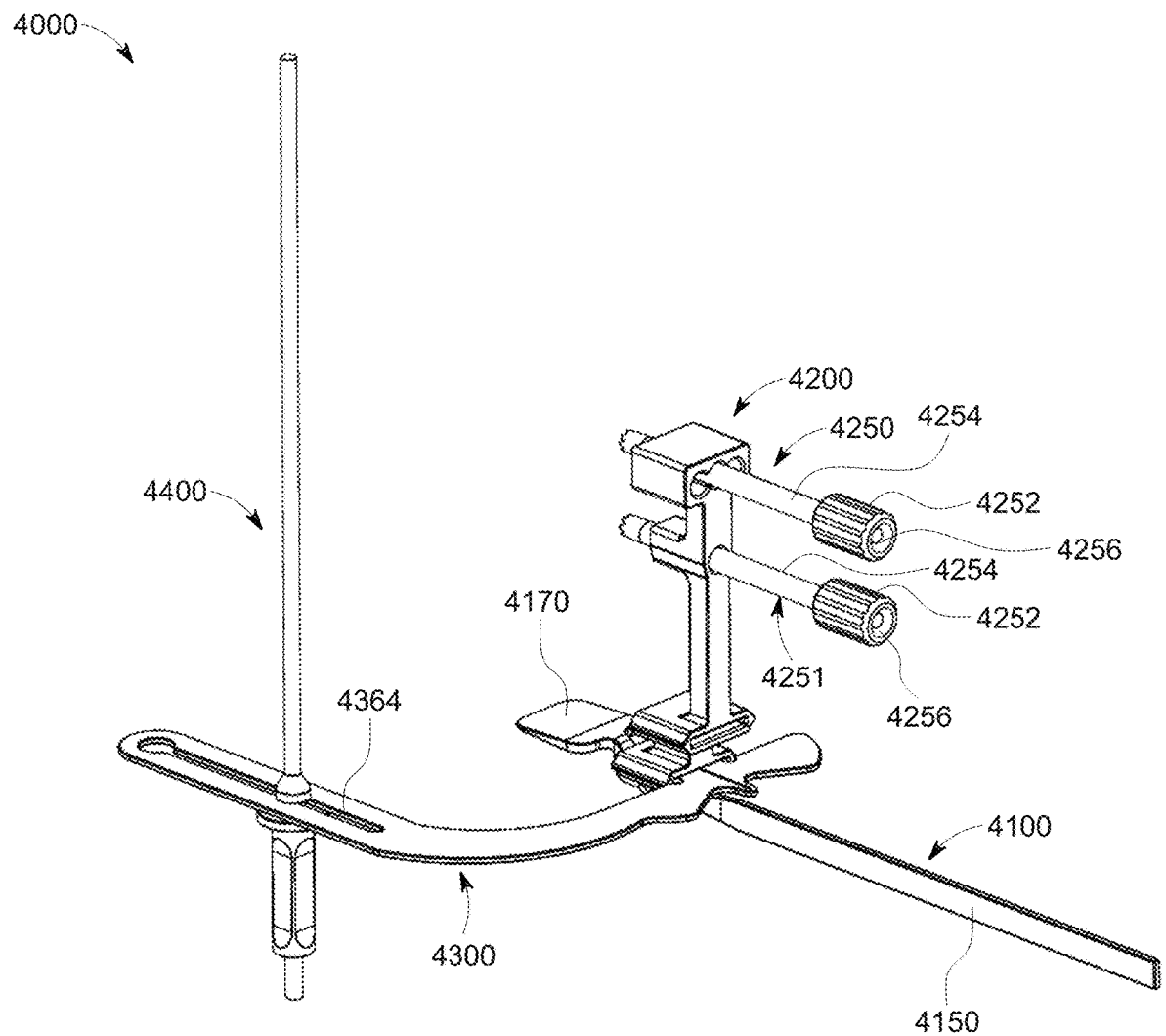
FIG. 45 is a perspective view of a joint-line referencing system, according to an embodiment of the present disclosure.
Figure 46:
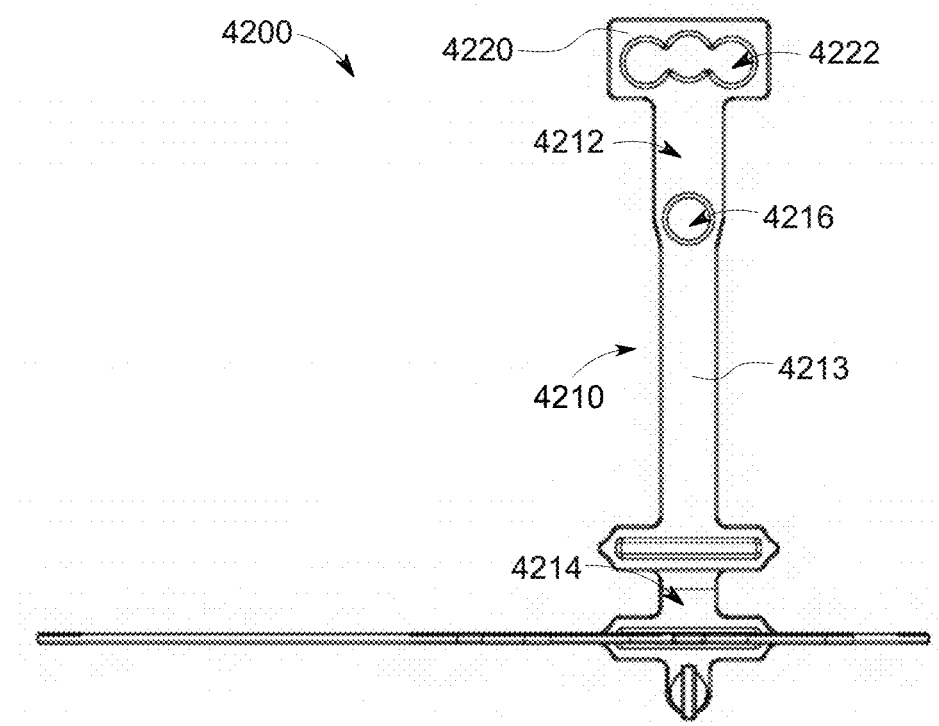
FIG. 46 is a front elevational view of the alignment arm, angelwing alignment member, and alignment foot of the joint-line referencing system of FIG. 45, according to an embodiment of the present disclosure.
Figure 47:
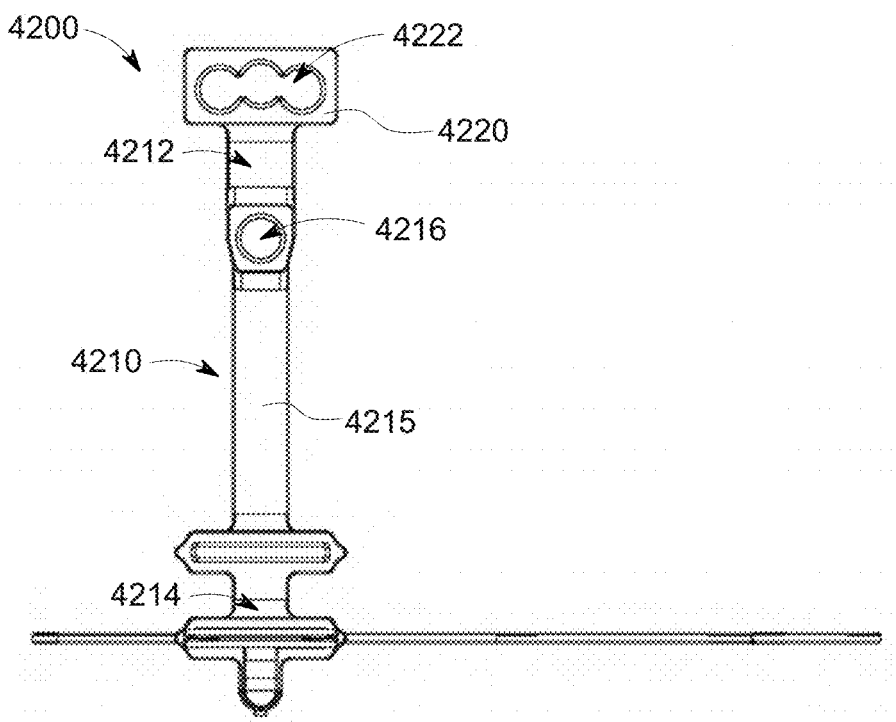
FIG. 47 is a rear elevational view of the alignment arm, angelwing alignment member, and alignment foot of the joint-line referencing system of FIG. 45, according to an embodiment of the present disclosure.
Figure 48:
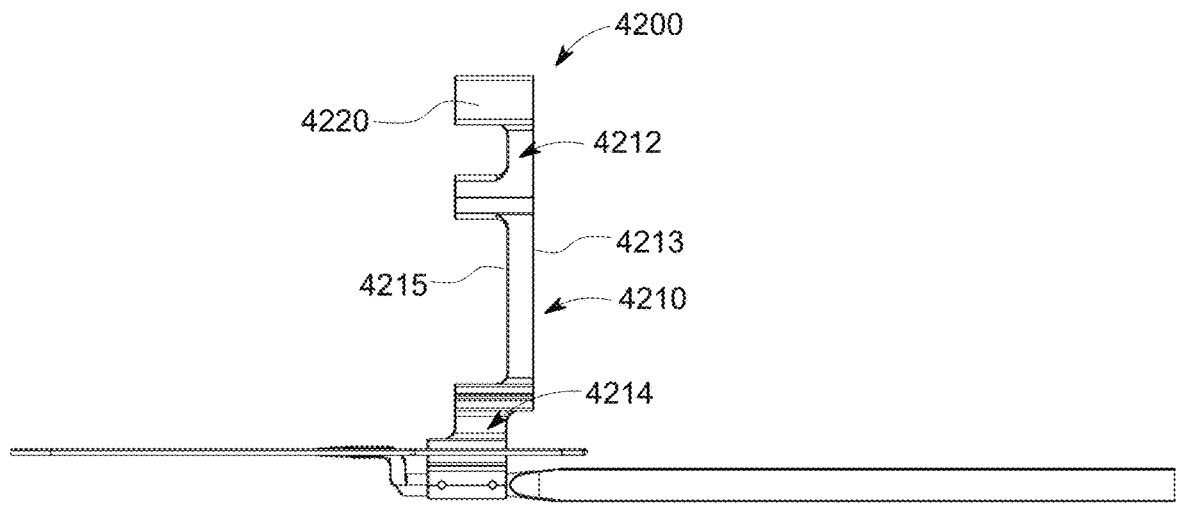
FIG. 48 is a first side elevational view of the alignment arm, angelwing alignment member, and alignment foot of the joint-line referencing system of FIG. 45, according to an embodiment of the present disclosure.
Figure 62:
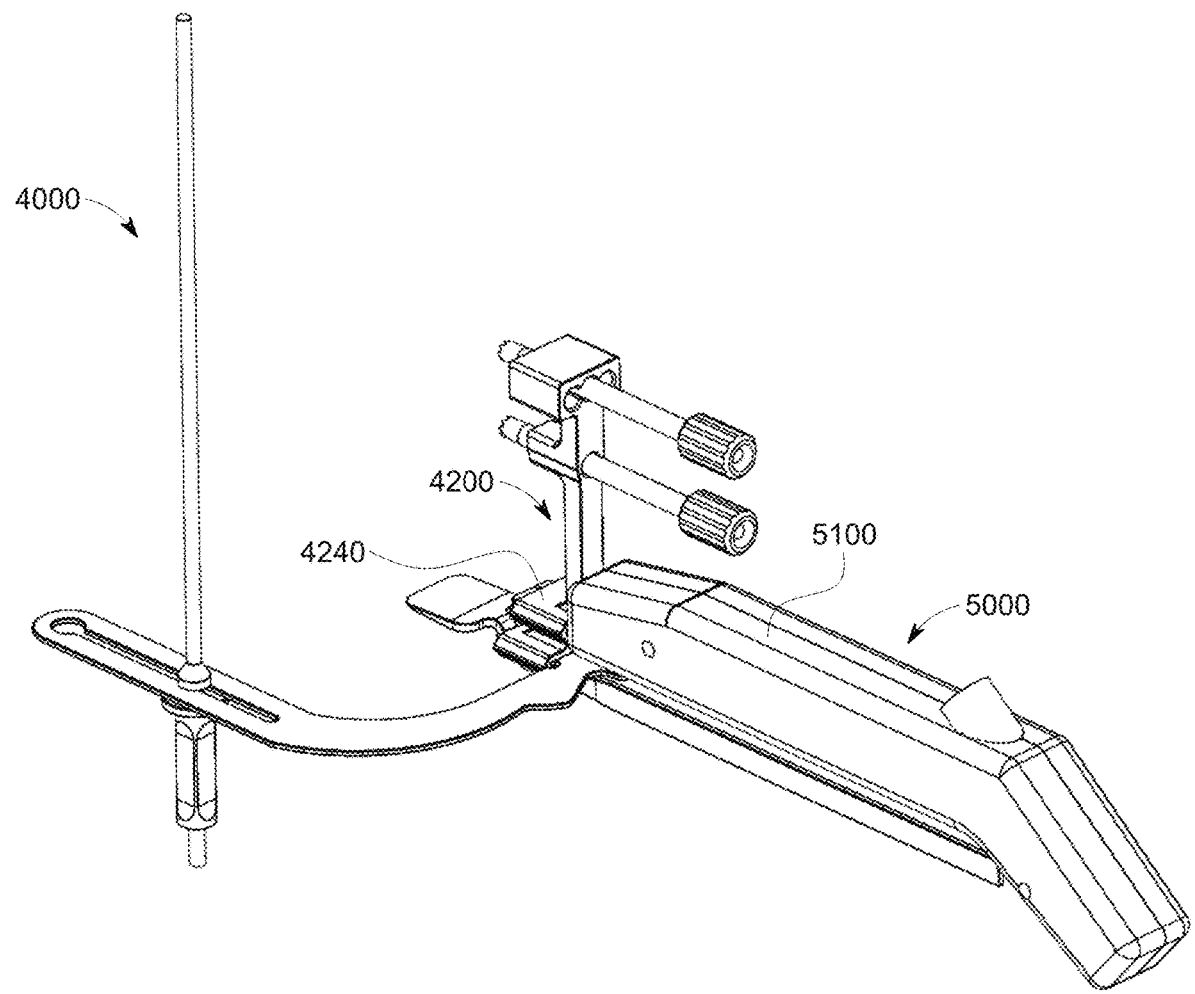
FIG. 62 is a perspective view of the joint-line referencing system of FIG. 45 with a laser alignment system, according to an embodiment of the present disclosure.

FIG. 45 illustrates a joint-line referencing system 4000, according to an embodiment of the present disclosure. For example, in some embodiments, the joint-line referencing system 4000 is operable with the TAG tower 300 (FIG. 16), the fast-track alignment system 600 (FIG. 27), and/or with a laser alignment system 5000 (FIG. 62). In this illustrated embodiment, the joint-line referencing system 4000 may include, for example, an alignment foot 4100 having a handle 4150 and a flat shim 4170, an alignment arm 4200, a first pin tube guide member 4250, a second pin tube guide member 4251, an angelwing alignment member 4300, and an alignment rod 4400.

Figures 54, 55:
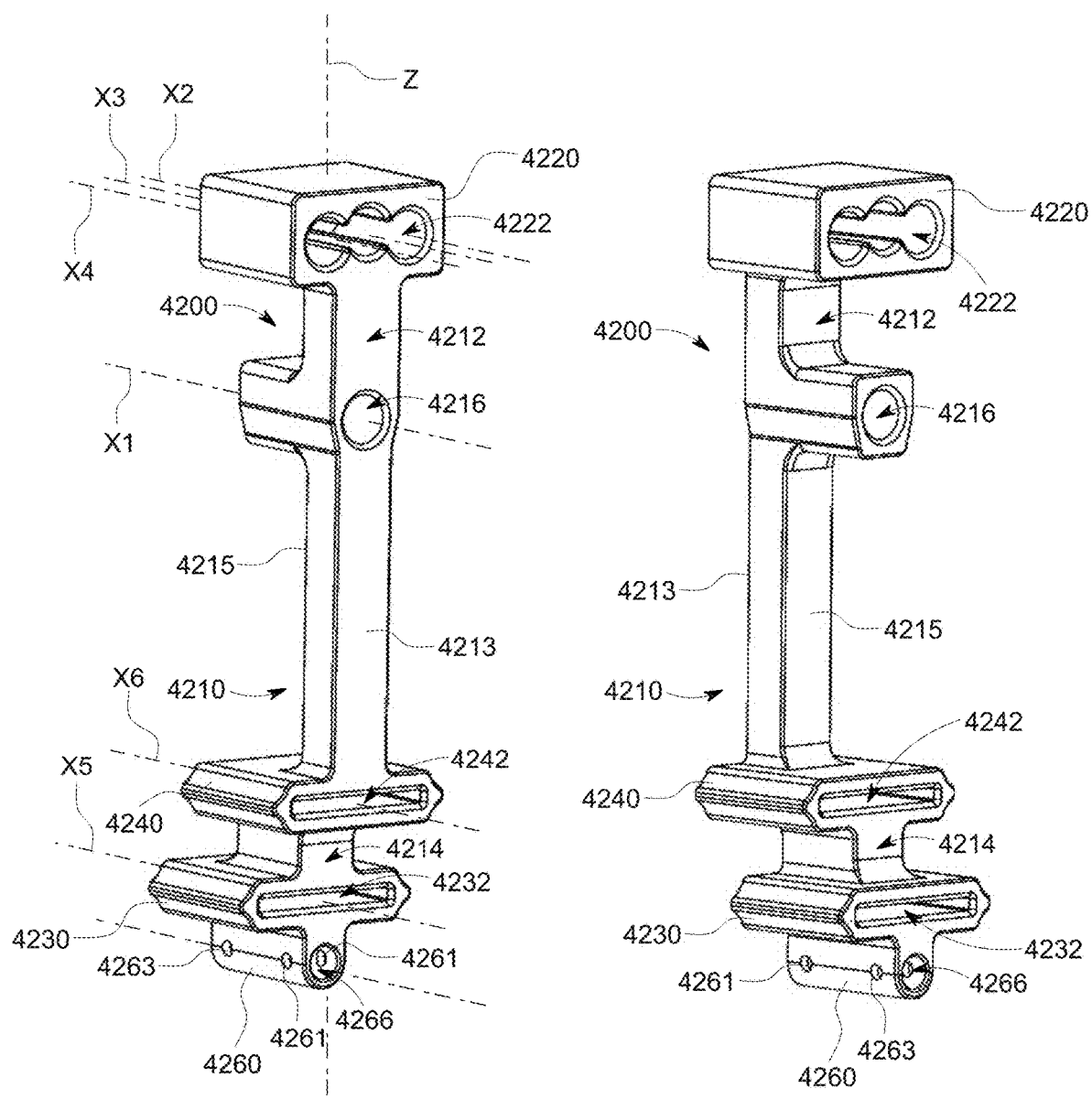
FIG. 54 is an enlarged, front perspective view of the alignment arm of the joint-line referencing system of FIG. 45, according to an embodiment of the present disclosure.
FIG. 55 is an enlarged, rear perspective view of the alignment arm of the joint-line referencing system of FIG. 45, according to an embodiment of the present disclosure.
Figure 56:
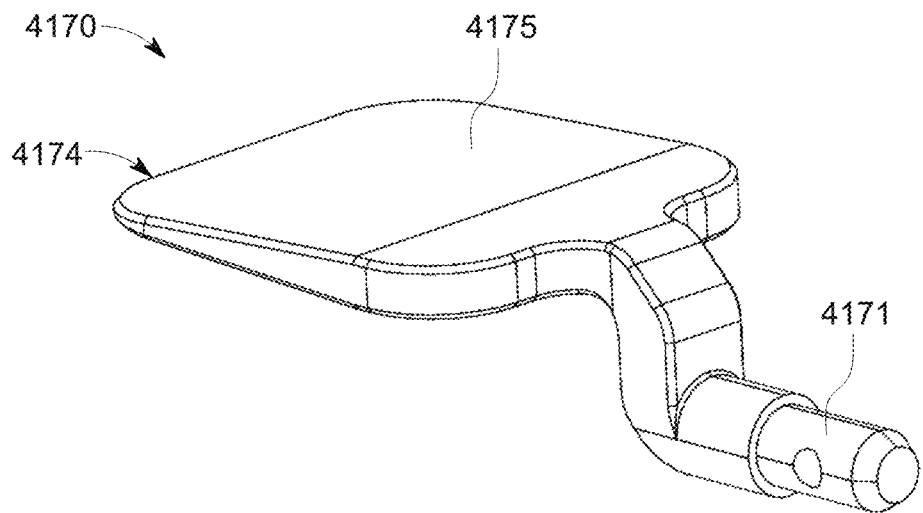
FIG. 56 is an enlarged, top perspective view of the shim of the alignment foot of the joint-line referencing system of FIG. 45, according to an embodiment of the present disclosure.
Figure 57:
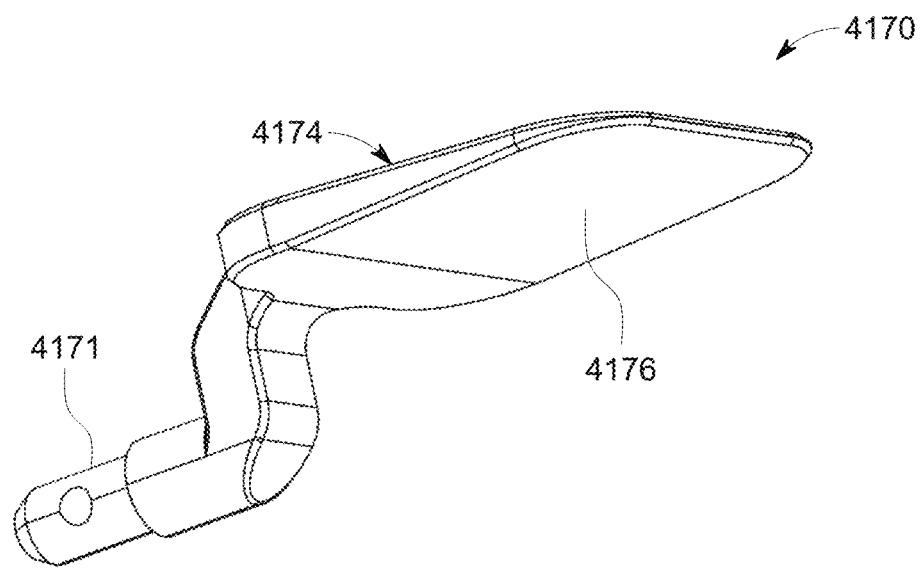
FIG. 57 is a bottom perspective view of the shim of FIG. 56, according to an embodiment of the present disclosure.
Figure 58:
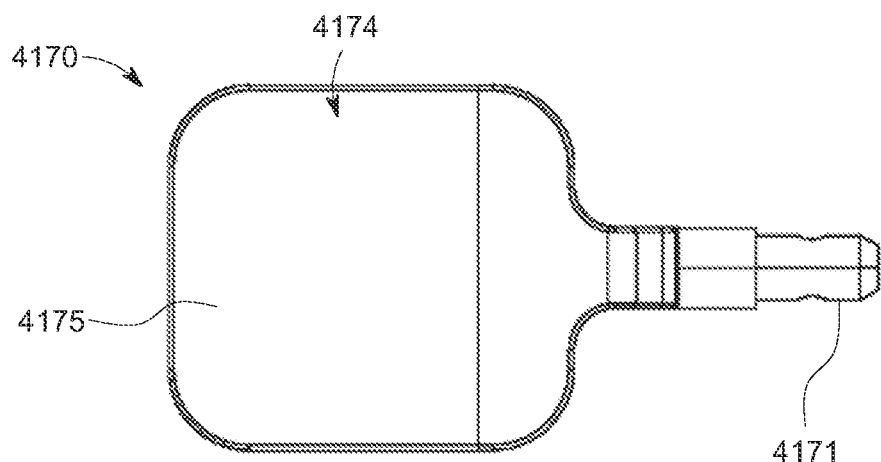
FIG. 58 is a top view of the shim of FIG. 56, according to an embodiment of the present disclosure.

With reference to FIGS. 46-55, the alignment arm 4200 may include a body 4210 having a first portion 4212, a second portion 4214, a first side 4213, and a second side 4215. The first portion 4212 of the alignment arm 4200 may include a pin tube holder 4220 defining at least one pin tube through-hole 4222 extending from the first side 4213 to the second side 4215 for receiving the pin tube guide member 4250 (FIG. 45). A pin tube through-hole 4216 extends from the first side 4213 to the second side 4215 and is operable for receiving the second pin tube guide member 4250 (FIG. 45) for use with, for example, the fast-track alignment system 600 (FIG. 27) and/or the laser alignment system 5000 (FIG. 62). The at least one pin tube through-holes 4222 may be separate individual side-by-side openings or a plurality of overlapping pin tube openings that allow for anatomic variations. The at least one pin tube through-hole 4222 may be, for example, three holes as shown in the depicted embodiment to allow for anatomic variations. The pin tube through-holes 4222 and the pin tube through-hole 4216 may be circular for receiving the cylindrical pin tube 4250 (FIG. 45). As shown in FIG. 54, for example, the alignment arm may define a longitudinal axis Z, pin tube through-hole 4216 may define an axis X1. Each of the pin tube through-holes 4222 may define axes X2, X3, and X4.

With reference to FIGS. 54 and 55, the second portion 4214 of the alignment arm 4200 may include a first base portion 4230 having an opening such as a slot 4232 opening onto the first side 4213 for receiving an auxiliary alignment instrument such as a tab 4370 (FIG. 52) of the angelwing alignment member 4300 (FIG. 52), or a laser alignment device (not shown), or other suitable alignment device. The second portion 4214 of the alignment arm 4200 may include a spaced apart second base portion 4240 having an opening such as a slot 4242 on the first side 4213 for receiving an auxiliary alignment instrument such as the laser alignment device 5000 (FIG. 62) as described below. Slots 4232 and 4242 may extend through body 4210 of alignment arm 4200 and be configured to open onto the first side 4213 and second side 4215. The openings 4232 and 4242 may be configured to allow for orienting the alignment angelwing member and/or the laser. As shown in FIG. 54, for example, each of the slots 4232 and 4242 may define axes X5 and X6, respectively. Pin tube through-hole axis X1-X4 and slot axis X5 and X6 may be parallel to each other, and disposed at 90 degrees from axis Z of the alignment arm.

A distal end of the first base portion 4230 may further include an outwardly-extending tab 4260 having a through-hole 4266 extending therethrough. A pair of pin holes 4261 and 4263 may extend through the outwardly extending tab 4260 for use with pins 4265 (FIG. 52) to attach the alignment foot 4100 (FIG. 45) to alignment arm 4200 as described below.

With reference again to FIG. 45, the pin tube guide members 4250 and 4251 may be essentially the same as pin tube guide members 250 (FIG. 1) described above. The angelwing alignment member 4300 may essentially the same as the angelwing alignment member 260 (FIG. 1) described above.

The angelwing alignment member 4300 allows a surgeon to assess the tibial slope. For example, the alignment rod 4400 may be movably coupled to the wing member 4300, such as within an elongated opening 4364 of the angelwing alignment member 4300, which elongated opening may extend anteriorly-posteriorly. The rod 4400 may be oriented perpendicularly (in at least one direction) or normal to the angelwing alignment member 4300, and thereby perpendicular (in at least one direction) or normal to the joint line referenced by the slot 4232 (FIG. 54) in the first base portion 4230 (FIG. 54), the slot 4242 (FIG. 54) in the second base portion 4240 (FIG. 54), and the angelwing alignment wing member 4300. The rod 4400 may thereby allow a surgeon to determine/evaluate the alignment (e.g., sagittal alignment) and/or orientation (e.g., sagittal slope and/or coronal slope) of the joint line of the anatomical configuration/structures of the patient (e.g., an ankle joint) and/or of a particular implant replacing such configuration/structures (e.g., a total ankle replacement implant) implanted on/in a resected bone that is resected (at least partially).

With reference again to FIGS. 52 and 53, the alignment foot 4100 may include the handle 4150 and the flat shim 4170 operably attachable to the alignment arm 4200. For example, the handle 4150 may be fixedly attachable to the alignment arm 4200 with a connector portion 4151 of the handle 4150 receivable in the through-hole 4266 (best shown in FIG. 54) via a fastener pin 4152 (FIG. 53), or screw, or other suitable fastening member. The shim 4170 is fixedly attachable to the alignment arm 4200 with a connector portion 4171 of the shim 4170 receivable in the through-hole 4266 (best shown in FIG. 55) via a fastener pin 4172 (FIG. 53), or screw, or other suitable fastening member. The fixed connection of the handle 4150, the shim 4170, and the alignment arm 4200 allows a surgeon using the handle 4150 to adjust the position and orientation of the joint-line referencing system 4100 (FIG. 45) relative to, for example, a joint between adjacent bones. The handle 4150 may be planar to easily allow a surgeon to grasp and reposition the handle, and thus position and orient the joint-line referencing system 4100 (FIG. 45).

Figure 59:
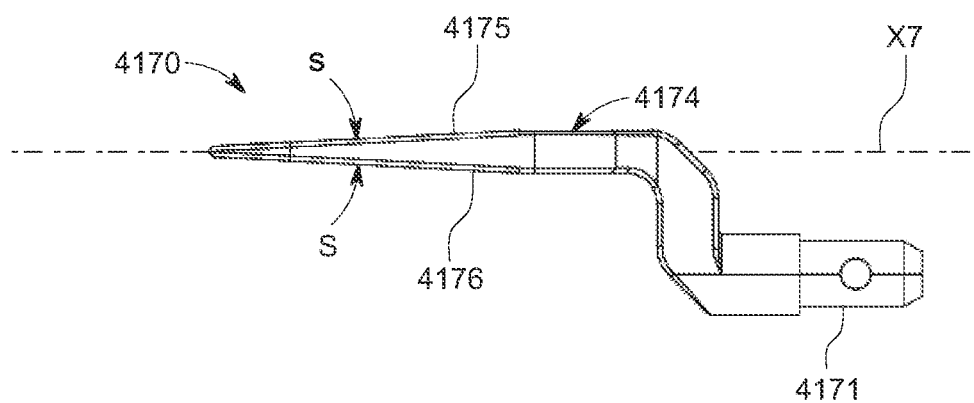
FIG. 59 is a side view of the shim of FIG. 58, according to an embodiment of the present disclosure.

With reference to FIGS. 56-59, the shim 4170 may include the connector 4171 and a generally planar portion 4174 having a first flat surface 4175 and a second flat surface 4176. In some embodiments, the shim 4170 may be a generally square planar member with rounded corners and with the first flat surface 4175 and the second flat surface 4176 tapering towards a distal end of the shim. For example, as shown in FIG. 59, the first flat surface 4175 and the second flat surface may be disposed at an angle S of about 0 degrees to about 10 degrees, about 2 degrees to about 8 degrees, about 4 degrees to about 6 degrees, about 0 degrees, 2 degrees, about 4 degrees, about 5 degrees, about 6 degrees, about 7 degrees, about 8 degrees, or disposed at any suitable angle. The shim 4170 is designed to fit in the joint between adjacent bones such as between the talus and tibia of an ankle joint in anterior-posterior and medial-lateral directions. The generally planar portion 4174 of the shim 4170 may define a longitudinal axis X7 parallel with the axes of the pin though-holes and slots in the alignment arm 4200 (FIG. 54).

Figure 49:
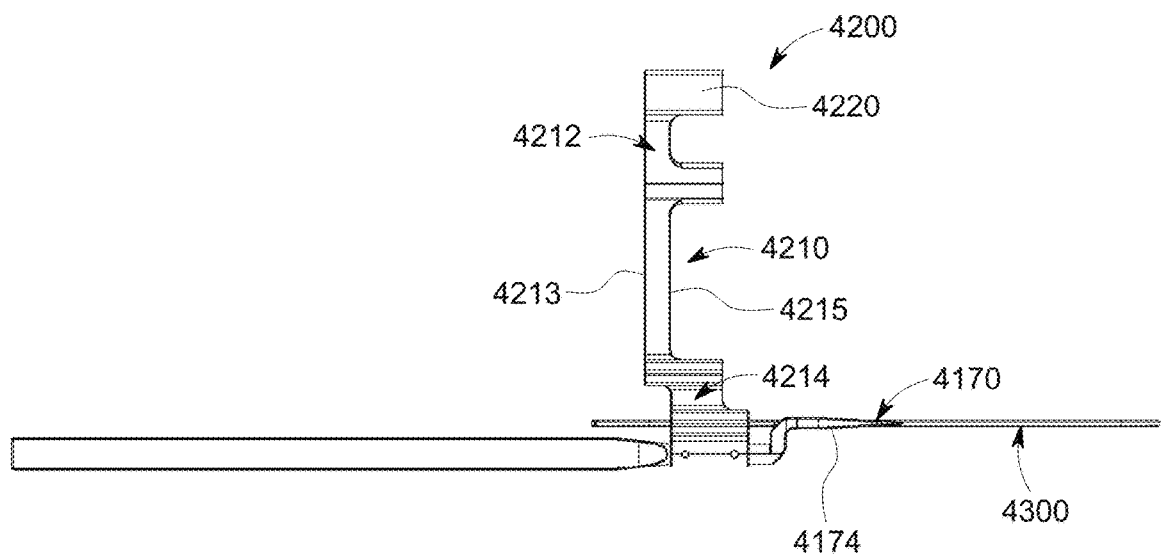
FIG. 49 is a second side elevational view of the alignment arm, angelwing alignment member, and alignment foot of the joint-line referencing system of FIG. 45, according to an embodiment of the present disclosure.
Figure 50:
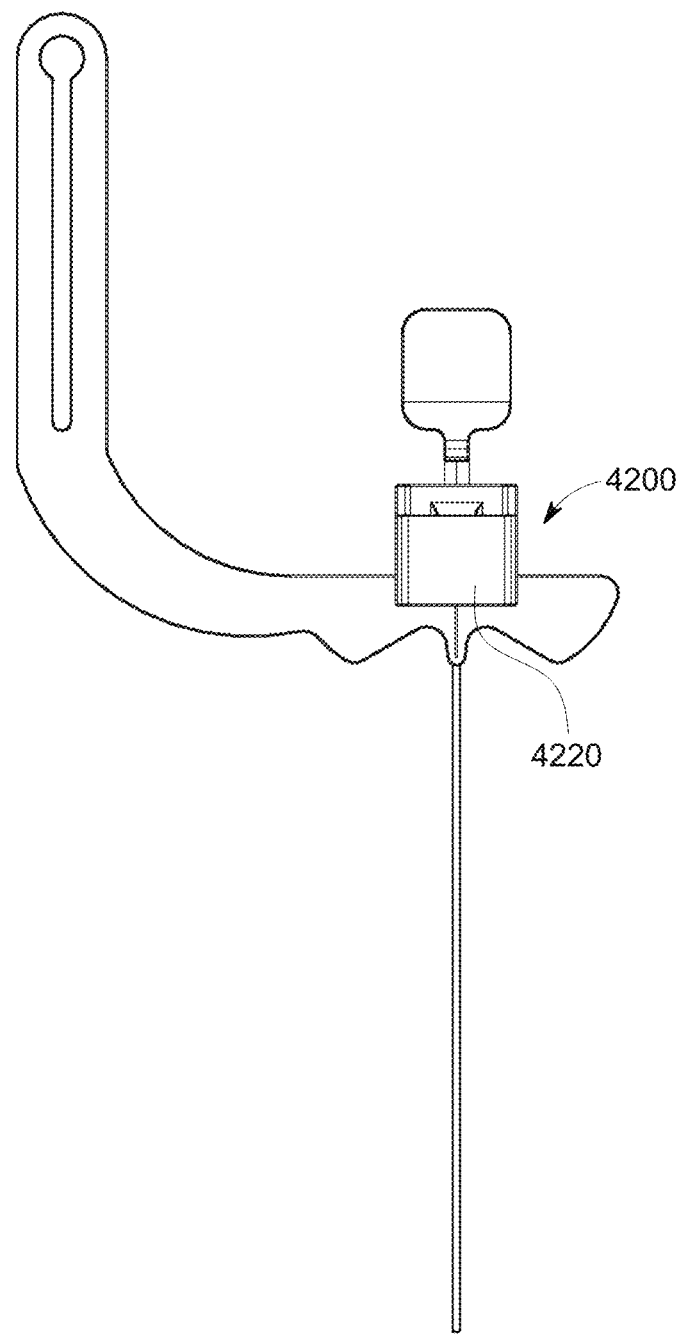
FIG. 50 is a top view of the alignment arm, angelwing alignment member, and alignment foot of the joint-line referencing system of FIG. 45, according to an embodiment of the present disclosure.
Figure 51:
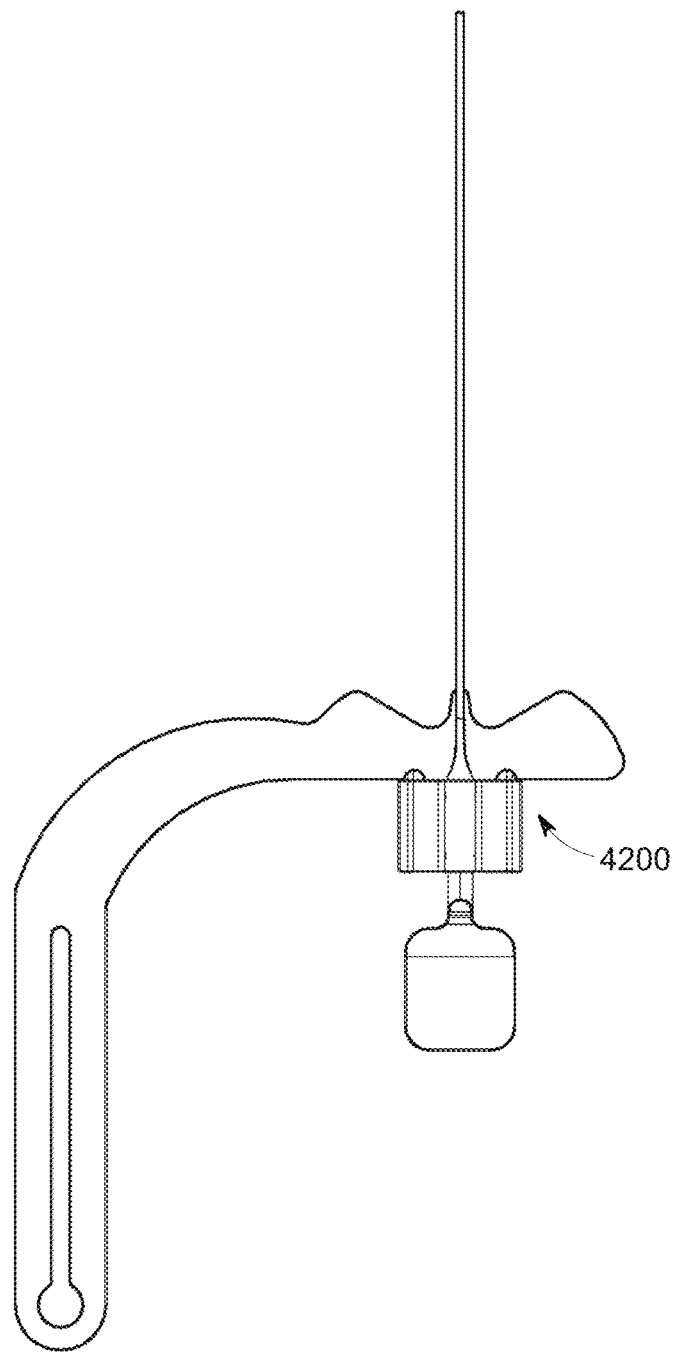
FIG. 51 is a bottom view of the alignment arm, angelwing alignment member, and alignment foot of the joint-line system of FIG. 45, according to an embodiment of the present disclosure.
Figure 52:
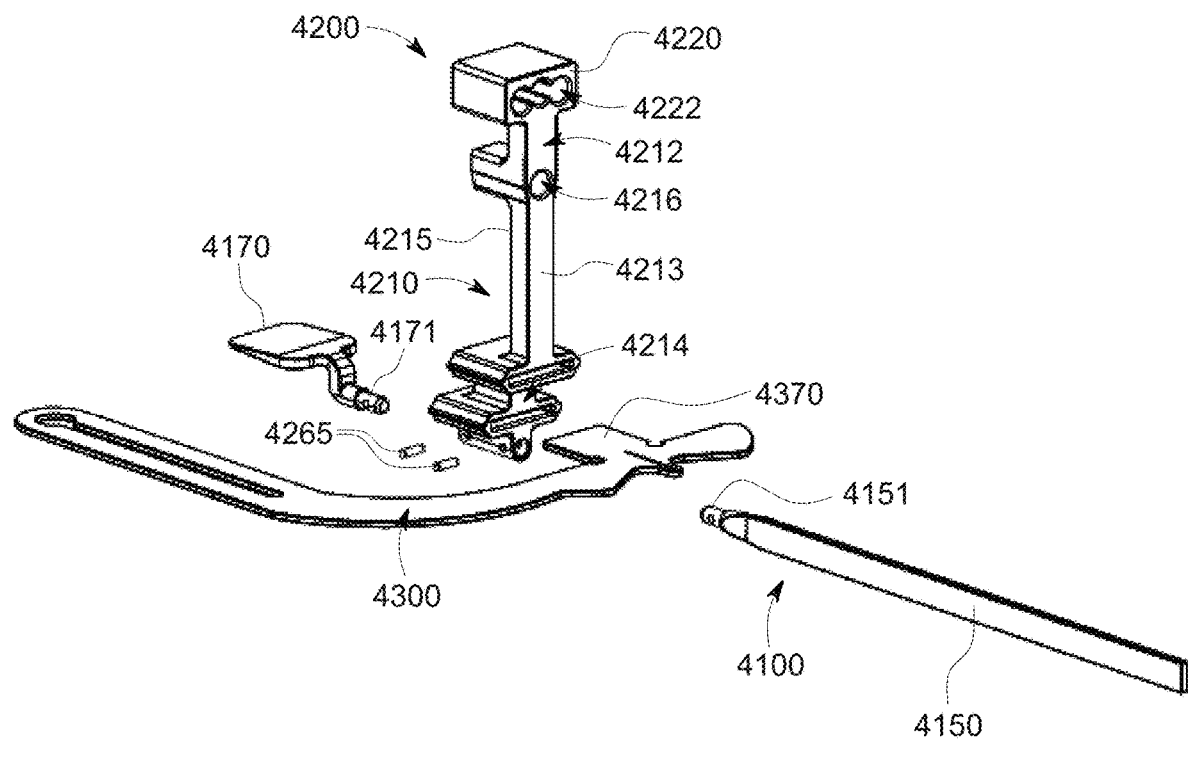
FIG. 52 is an exploded, top perspective view of the alignment arm, angelwing alignment member, and alignment foot of the joint-line referencing system of FIG. 45, according to an embodiment of the present disclosure.
Figure 53:
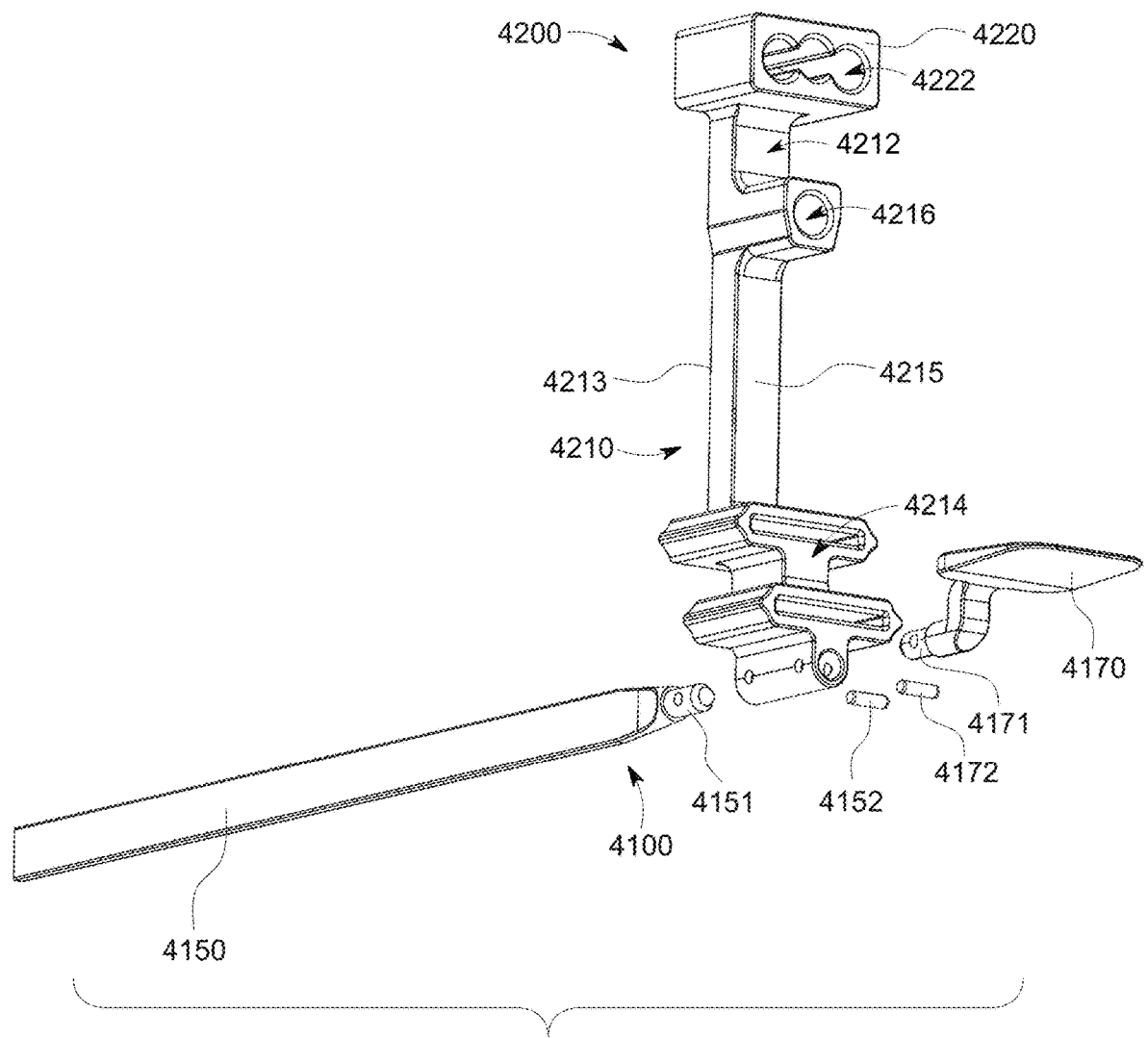
FIG. 53 is an exploded, bottom perspective view of the alignment arm and alignment foot of the joint-line referencing system of FIG. 45, according to an embodiment of the present disclosure.

With reference again to FIGS. 56-59, the connector 4171 of the shim 4170 is offset relative to the generally planar portion 4174. This allows, as shown in FIG. 49, for the generally planar portion 4174 of the shim 4170 to be disposed parallel and in line with angelwing alignment member 4300 in the assembled joint line referencing system 4000 (FIG. 45).

Figure 60:
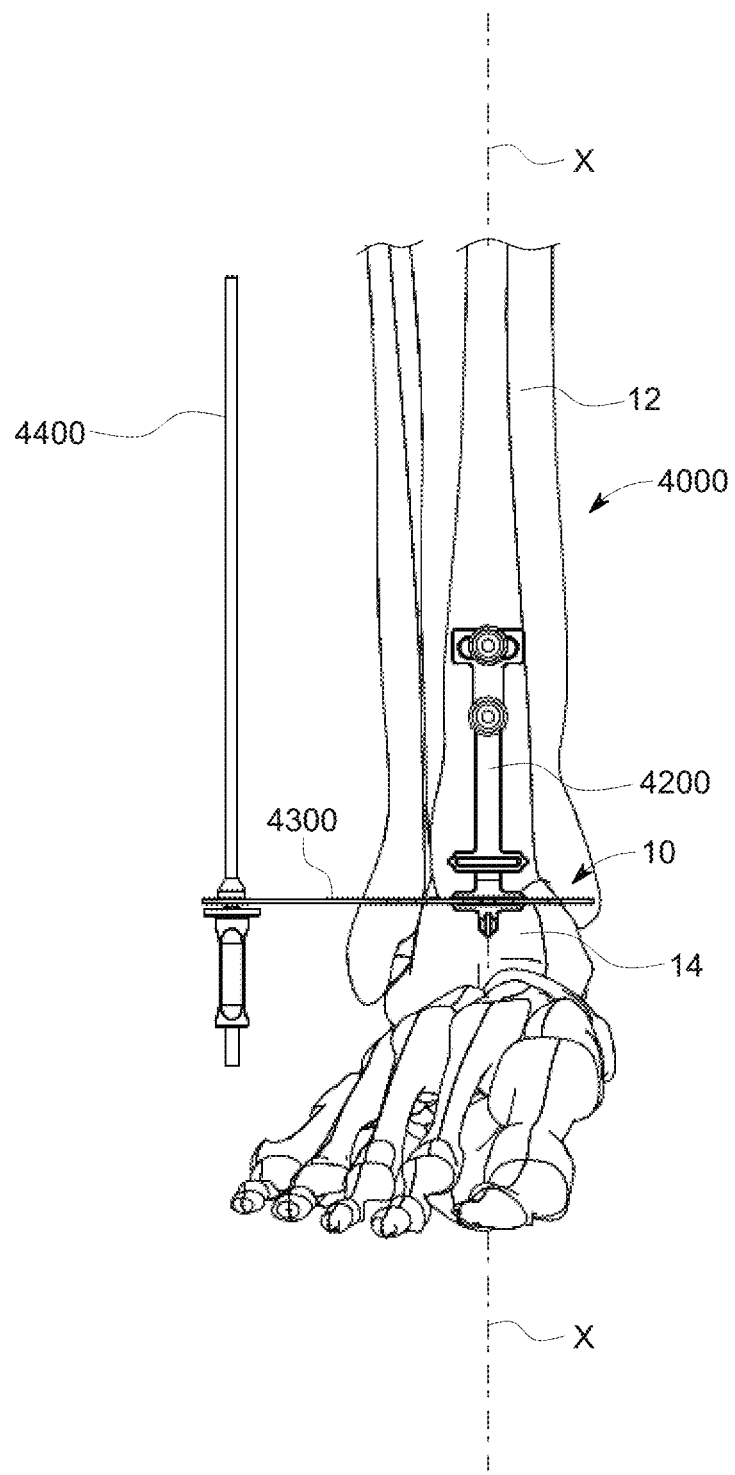
FIG. 60 is a front view of the joint-line referencing system of FIG. 45 positioned relative to a patient's lower extremity, according to an embodiment of the present disclosure.
Figure 61:
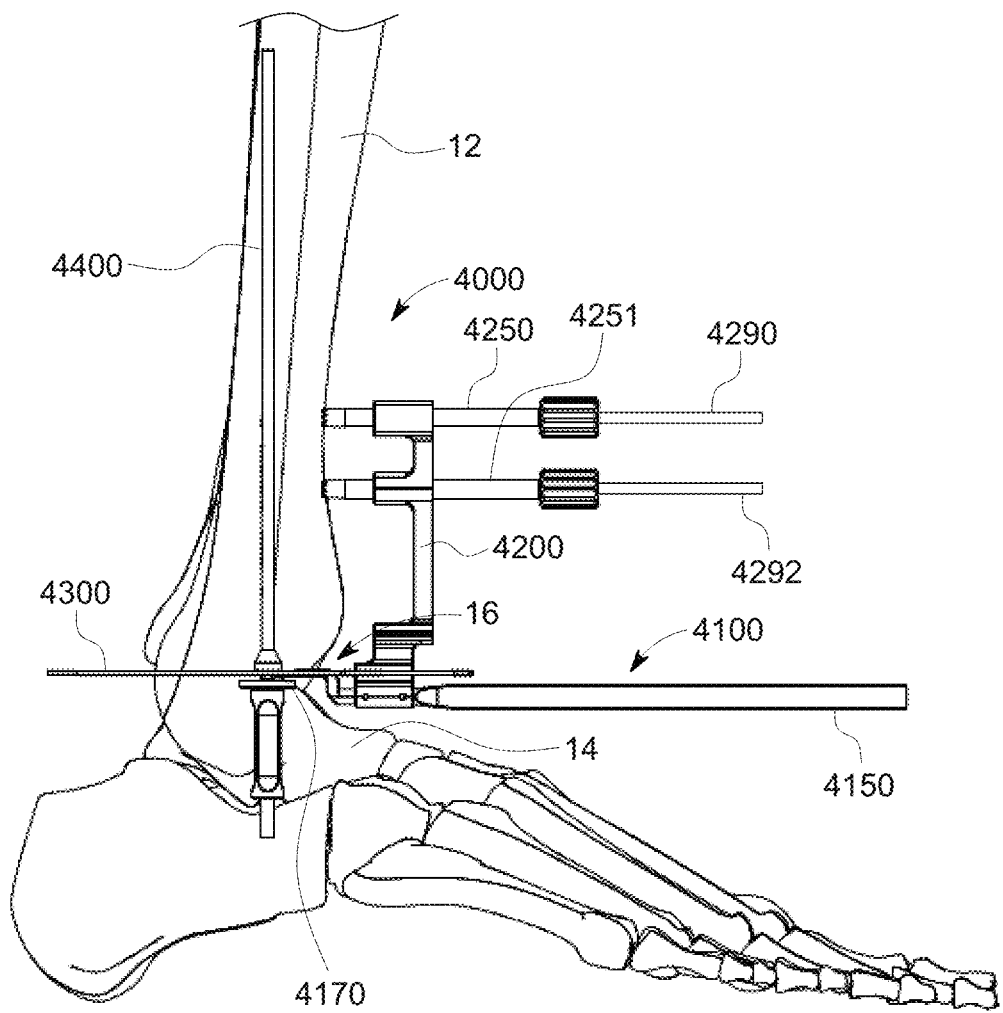
FIG. 61 is a side view of the joint-line referencing system of FIG. 60 and pins attached to the patient's lower extremity, according to an embodiment of the present disclosure.

FIGS. 60 and 61 illustrate the initial steps of an alignment procedure, which may subsequently include the joint-line referencing system 4000 for use in the TAG technique in a TAR surgery, according to an embodiment of the present disclosure.

For example, for use in the TAG technique in a TAR surgery, the initial steps of an alignment procedure may include placing the shim 4170 (FIG. 61) of the alignment foot 4100 (FIG. 61) into the joint 10 between, e.g., the tibia 12 and the talus 14 of the patient. Specifically, the shim 4170 (FIG. 61) is placed between the tibia plafond and the superior talar dome. The handle 4150 (FIG. 61) may be used, for example, to position and/or orient the alignment foot 4100, and thus, the coupled alignment arm 4200, in the transverse plane (i.e., internal-external rotation).

Next, the angelwing alignment member 4300 inserted into the slot 4232 (FIG. 54) of the base portion 4230 (FIG. 54) may be used by a surgeon to assess the tibial slope. The rod 4400 may be used to determine/evaluate the alignment (e.g., sagittal alignment) and/or orientation (e.g., sagittal slope and/or coronal slope) of the joint line of the anatomical configuration/structures of the patient (e.g., an ankle joint). As shown in FIG. 60, the joint-line referencing system 4000 may be utilized and positioned and/or orientated with respect to any axis X-X of the anatomical structure of interest. With reference again to FIG. 61, after the desired position and/or orientation of the joint-line referencing system 4000 is achieved, a first pin 4290 is inserted in pin hole 4256 (FIG. 45) of first guide member 4250 and drilled into the tibia 12. The inserted pin 4290 secures the selected tibial slope and internal-external rotation.

In some embodiments, the joint line referencing system 4000 may be removed, whereby the first pin 4290 remains inserted into the tibia 12. For example, the pin tube guide member 4250 may be removed, and simultaneously the alignment arm 4200 may be removed from the pin 4290 and the shim 4170 removed from the joint. The first pin 4290 serves as the starting point for the next portion of the surgical procedure, i.e., the TAG technique. The inserted pin 4290 may be employed with a tibia alignment guide (TAG) technique for use in a TAR surgery, for example, as illustrated in FIGS. 16-19 and described above.

In other embodiments and with reference again to FIGS. 60 and 61, the initial steps of an alignment procedure may subsequently include the joint-line referencing system 4000 for use in the fast-track alignment technique in a TAR surgery.

For example, for use in the fast-track alignment technique in a TAR surgery, the initial steps of an alignment procedure may include placing the shim 4170 (FIG. 61) of the alignment foot 4100 (FIG. 61) into the joint 10 between, e.g., the tibia 12 and the talus 14 of the patient. Specifically, the shim 4170 (FIG. 61) is placed between the tibia plafond and the superior talar dome. The handle 4150 (FIG. 61) may be used, for example, to position and/or orient the alignment foot 4100, and thus, the coupled alignment arm 4200, in the transverse plane (i.e., internal-external rotation).

Next, the angelwing alignment member 4300 is inserted into the slot 4232 (FIG. 54) of the base portion 4230 (FIG. 54) may be used by a surgeon to assess the tibial slope. The rod 4400 may be used to determine/evaluate the alignment (e.g., sagittal alignment) and/or orientation (e.g., sagittal slope and/or coronal slope) of the joint line of the anatomical configuration/structures of the patient (e.g., an ankle joint). As shown in FIG. 60, the joint-line referencing system 4000 may be utilized and positioned and/or orientated with respect to any axis X-X of the anatomical structure of interest. After the desired position and/or orientation of the joint-line referencing system 4000 is achieved, a first pin 4290 is inserted in pin hole 4256 (FIG. 45) of first guide member 4250 (FIG. 61) and drilled into the tibia 12, and then a second pin 4292 (FIG. 61) is inserted in the pin hole of the second pin tube guide member 4251 (FIG. 61) and drilled into the tibia 12. The inserted pins 4290 (FIG. 61) and 4292 (FIG. 61) secure the selected tibial slope and internal-external rotation. The method of using the joint-line referencing system for this technique is similar to the joint-line referencing system to the TAG technique, except that the additional second pin 4292 is drilled into the distal tibia of the patient. As will be appreciated, the second pin 4292 takes the place of the proximal pin used in the TAG technique.

The joint line referencing system 4000 may be removed, whereby the first pin 4290 and the second pin 4292 remain inserted into the tibia 12. For example, the pin tube guide members 4250 (FIG. 61) and 4251 (FIG. 61) may be removed, and simultaneously the alignment arm 4200 may be removed from the pins 4290, 4292 and the shim 4170 (FIG. 61) removed from the joint. These two pins are the starting point for the supporting, for example, the fast-track alignment system 600 (FIG. 27). For example, the pins 4290 and 4292 serve as the starting point for the next portion of the surgical procedure, i.e., the fast-track technique. The inserted pins 4290 and 4292 may be employed with the fast-track alignment system 600 (FIG. 27) for use in a TAR surgery, for example, as illustrated in FIGS. 27-30 and described above.

With reference to FIG. 62, therein illustrated is the joint-line referencing system 4000 with a laser alignment system 5000, according to an embodiment of the present disclosure. For example, in some embodiments, the joint-line referencing system 4000 with the laser alignment system 5000 may be operable with the TAG tower 300 (FIG. 16) or with the fast-track alignment system 600 (FIG. 27) for use in a TAR surgery. As described in greater detail below, the laser alignment system 5000 may be operably connected to the joint-line referencing system 4000 via the slot 4242 (FIG. 54) of base member 4240 (FIG. 54) of alignment arm 4200.

Figure 63:
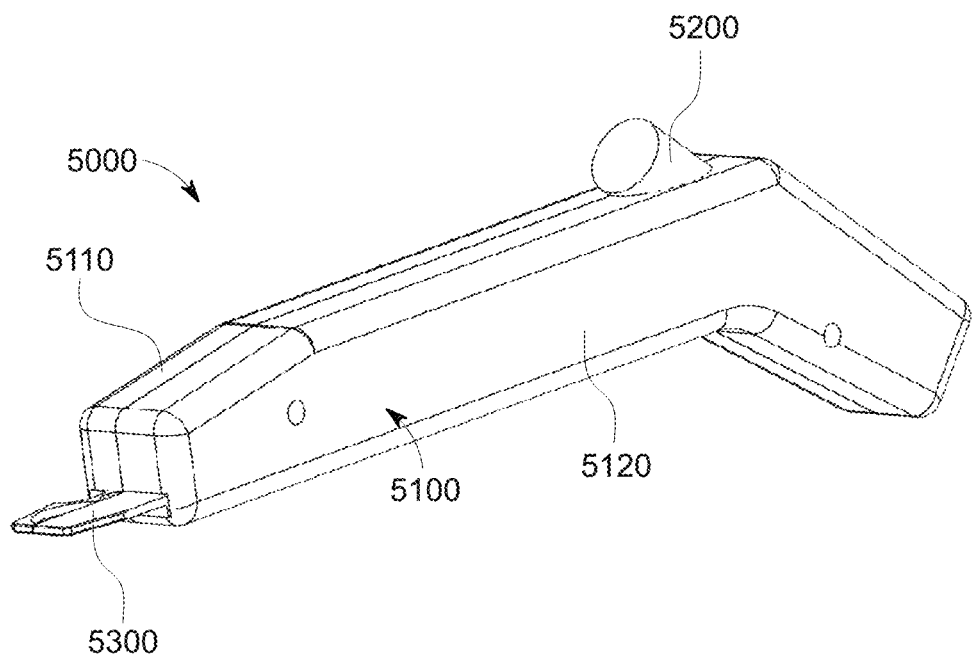
FIG. 63 is a perspective view of the laser alignment system of FIG. 62, according to an embodiment of the present disclosure.
Figure 64:
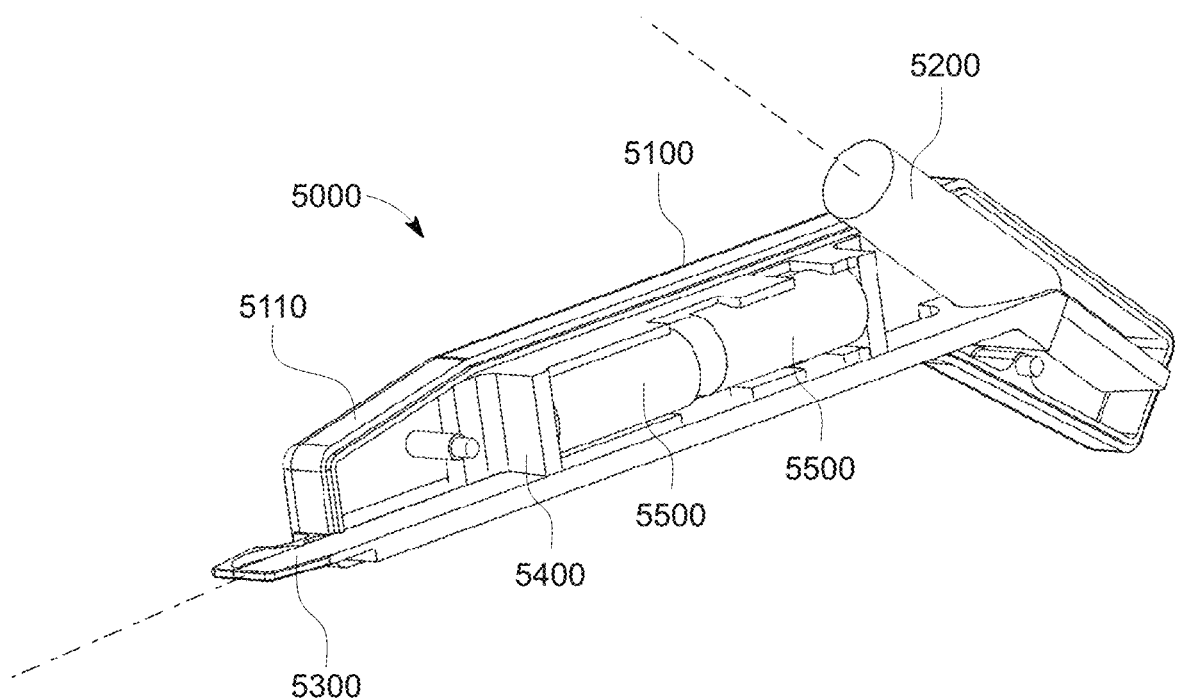
FIG. 64 is a perspective view, partially cut away, of the laser alignment system of FIG. 62, according to an embodiment of the present disclosure.
Figure 65:
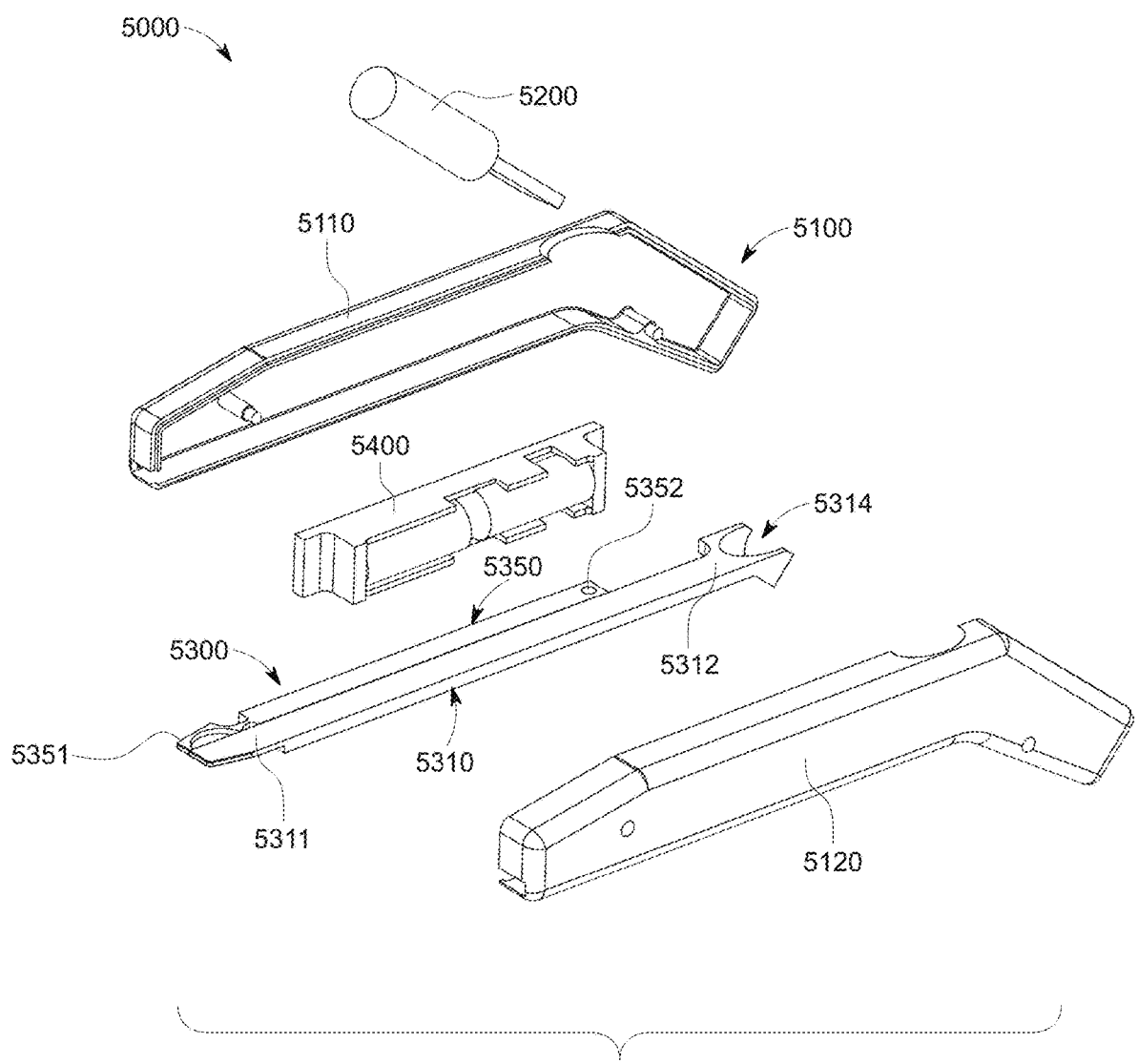
FIG. 65 is an exploded perspective view of the laser alignment system of FIG. 62, according to an embodiment of the present disclosure.

As shown in FIGS. 63-65, the laser alignment system 5000 may generally include a housing 5100, a laser device 5200, an insert shim 5300, a power source holder or battery holder 5400 (FIG. 64), and one or more power sources such as a plurality of batteries 5600 (FIG. 64). A distal end of the insert shim 5300 extends from the housing 5100. The distal end of the insert shim 5300 is receivable in the slot 4242 (FIG. 54) of base member 4240 (FIG. 62) of the alignment arm 4200 (FIG. 63). The housing 5100 may include a first half 5110 and a second half 5120. The laser device 5200 may be disposed at an angle relative to the insert shim 5300.

With reference to FIG. 65, the insert shim 5300 may include a first portion 5310 and a second portion 5350. The first portion 5310 of the insert shim 5300 may have a distal end 5311 and a proximal end 5312 having a cutout 5314 configured and angled for receiving and positioning the laser device 5200. The second portion 5350 of the insert shim 5300 may have a distal end 5351 and a proximal end 5352. The distal end 5351 may act as an electrical switch for turning on the laser device 5200 when the distal end of the insert shim is inserted in slot 4242 (FIG. 54) of alignment arm 42 (FIG. 54).

Figure 66:
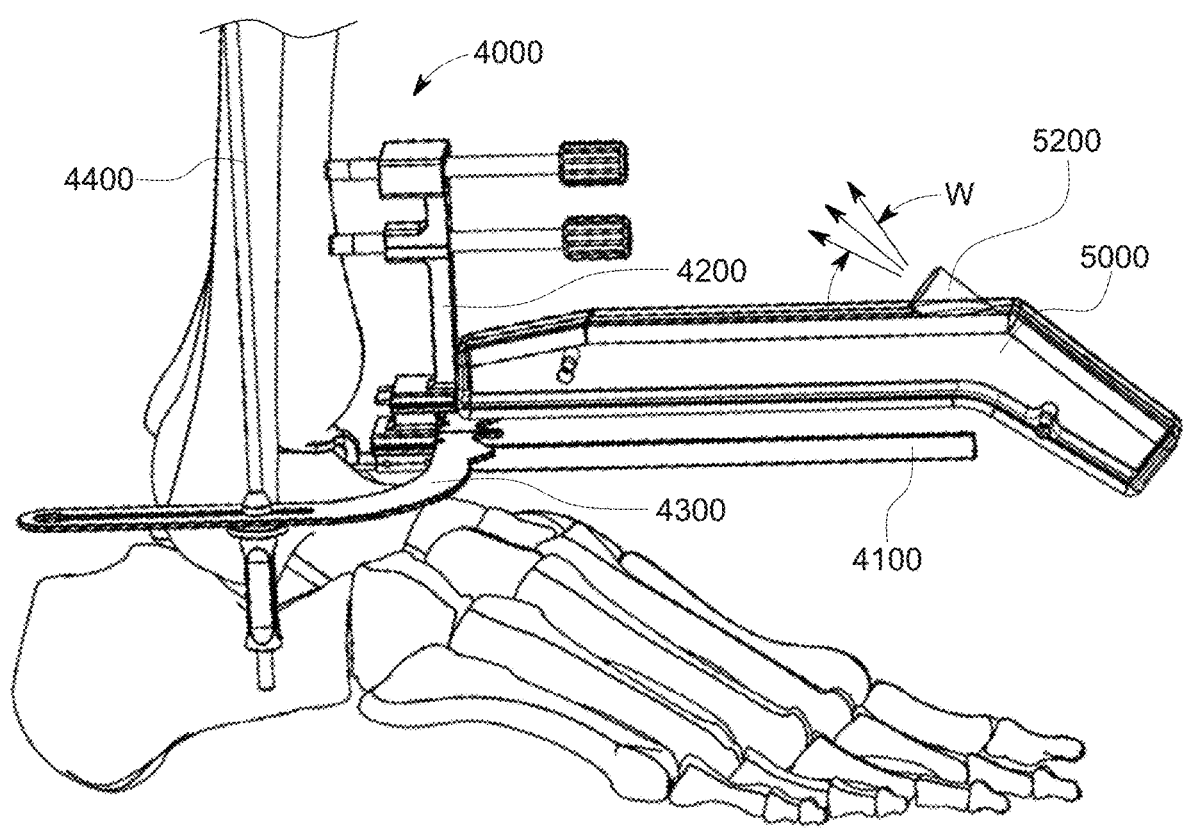
FIG. 66 is a side perspective view of the joint-line referencing system and laser alignment system of FIG. 62 aligned with a patient's lower extremity, according to an embodiment of the present disclosure.
Figure 67:
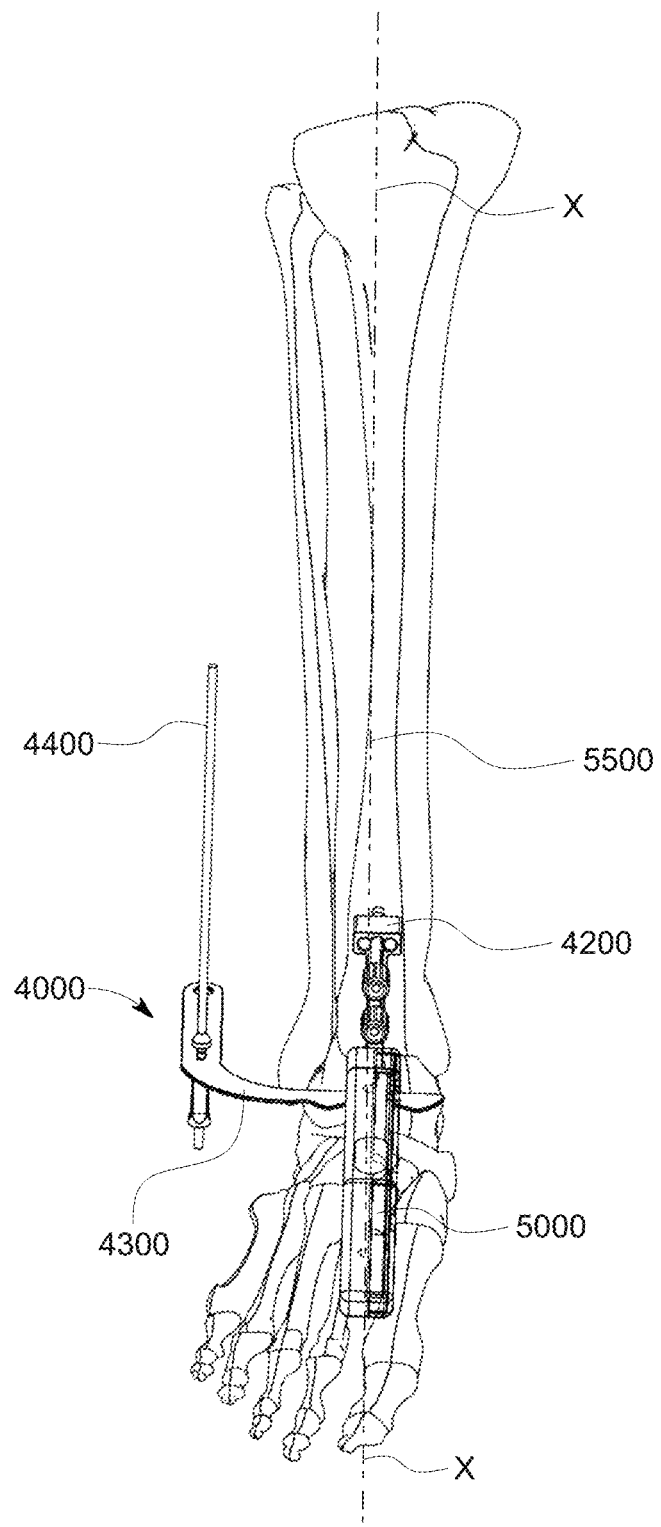
FIG. 67 is a front perspective view of the joint-line referencing system and the laser alignment system of FIG. 66 aligned with a patient's lower extremity, according to an embodiment of the present disclosure.

FIGS. 66 and 67 illustrate the joint-line referencing system 4000 with the laser alignment system 5000 aligned relative to a patient's lower extremity, according to an embodiment of the present disclosure. The combination of the alignment foot 4100 (FIG. 66), alignment arm 4200, the angelwing alignment member 4300, the alignment rod 4400, and the laser alignment system 5000 may be used by a surgeon to orient and position joint-line referencing system 4000 relative to a patient's lower extremity. In this illustrated embodiment, the laser alignment system 5000 may emit laser light therefrom orientated at a fixed angle relative to alignment arm 4200. The emitted and projected laser light may be in a plane over an angle W resulting in an illuminated laser line 5500 (illustrated in dashed lines in FIG. 67) on the patient's lower extremity (e.g., on the outer skin surface of the patient's lower extremity) when the distal end 5351 (FIG. 65) acting as a switch activates the laser device 5000 (FIG. 66). As shown in FIG. 67, the laser light line 5500 can be aligned to the alignment axis (e.g., an anatomical or mechanical axis) of the anatomical configuration/structures of the patient via the surgeon positioning and orientating the joint-line referencing system 4000.

In some embodiments, the laser device 5200 may be configured to emit a fan shaped laser light plane with a fan angle within the range of about 1 degree to about 75 degrees (e.g., 1, 5, 10, 20, 30, 45, 60, or 75 degrees). In some embodiments, the laser device 5200 may be configured to emit a fan shaped laser light plane with a fan angle of about 60 degrees. In some embodiments, the laser device 5200 may be configured to emit a laser light plane with a beam angle of less than 3 rad. In alternative embodiments, the laser light may emanate in configurations other than a laser line (i.e., the incident light may form a point or dot).

In some embodiments, in addition to emitting a linear laser line 5500 (via a fan shaped laser light plane), the laser device 5200 may be configured to emit at least one secondary linear laser line (not shown) (e.g., via a fan shaped laser light plane), which may be orientated perpendicular to the linear laser line 5500. The secondary linear laser line may further assist the surgeon in properly positioning and orienting the joint-line referencing system 4000 with respect to the anatomical configuration/structures of the patient (e.g., to the alignment axis (e.g., an anatomical or mechanical axis) of the anatomical configuration/structures of interest).

FIG. 68 illustrates a surgical method 6000, according to an embodiment of the present disclosure. For example, the method 6000 may include at 6100 placing a shim into a joint between a first bone and a second bone of a patient, at 6200 moving a handle operably attached to the shim to position and/or orient an alignment arm relative to the first bone, at 6300 inserting a first pin through a hole of the alignment arm and into the first bone, at 6400 removing the shim from the joint and the alignment arm from the first pin, at 6500 installing an alignment guide on the installed first pin, and at 6600 using a cutting guide operably attached to the alignment guide to resect a portion of the first bone and/or the second bone.

FIG. 69 illustrates a surgical method 7000, according to an embodiment of the present disclosure. For example, the method 7000 may include at 7100, placing a shim into a joint between a first bone and a second bone of a patient, at 7200 moving a handle operably attached to the shim to position and/or orient an alignment arm relative to the first bone, at 7300 inserting a first pin through a first hole of the alignment arm and into the first bone, at 7400 inserting a second pin through a second hole of the alignment arm and into the first bone, at 7500 removing the shim from the joint and the alignment arm from the first and the second pins, at 7600 installing an alignment guide on the installed pins, at 7700 using a cutting guide operably attached to the alignment guide to resect a portion of the first bone and/or the second bone.

In the various embodiments of the joint line systems and methods of the present disclosure may be configured to provide alignment (e.g., manipulation to achieve alignment) in three planes (e.g., along or in the sagittal, coronal and transverse planes), covering six degrees of freedom.

The above disclosure describes a portion of a total ankle replacement (TAR) procedure and the devices used in that procedure. Additional understanding of the TAR procedure may be found in U.S. Provisional Application No. 62/779,436 filed Dec. 13, 2018, and entitled Joint Replacement Systems and Methods of Use and Assembly, International Application No. PCT/US2019/029009 filed Apr. 24, 2019, and entitled Implants and Methods of Use and Assembly, U.S. Provisional Application No. 62/779,092 filed Dec. 13, 2018, and entitled Instruments, Guides and Related Methods for Total Ankle Replacement, International Application No. PCT/US2019/066404 filed Dec. 13, 2019, and entitled Instruments, Guides and Related Methods for Total Ankle Replacement, U.S. Provisional Application No. 62/890,611 filed Aug. 22, 2019, and entitled Patient Specific Instruments and Methods of Use, International Application No. PCT/US2019/066336 filed Dec. 13, 2019, and entitled Patient Specific Instruments and Methods of Use, U.S. Provisional Application No. 62/899,703 filed Sep. 12, 2019, and entitled Joint Replacement Alignment Guides, Systems and Methods of Use and Assembly, International Application No. PCT/US2019/066408 filed Dec. 13, 2019, and entitled Joint Replacement Alignment Guides, Systems and Methods of Use and Assembly, U.S. Provisional Patent Application No. 62/899,655, filed Sep. 12, 2019, and entitled Alignment Instruments And Methods For Use In Total Ankle Replacement, International Application No. PCT/US2019/066149, filed on Dec. 13, 2019, and entitled Alignment Instruments And Methods For Use In Total Ankle Replacement, U.S. Provisional Application No. 62/899,740 filed Sep. 12, 2019, and entitled Joint Replacement Alignment Guides, Systems and Methods of Use and Assembly, International Application No. PCT/US2019/066393 filed Dec. 13, 2019, and entitled Joint Replacement Alignment Guides, Systems and Methods of Use and Assembly, U.S. Provisional Application No. 62/898,615 filed Sep. 11, 2019, and entitled Resection Guides, Sweeping Reamers, and Methods for Use in Total Ankle Replacement, International Application No. PCT/US2019/064948 filed Dec. 6, 2019, and entitled Resection Guides, Sweeping Reamers, and Methods for Use in Total Ankle Replacement, U.S. Provisional Application No. 62/898,854 filed Sep. 11, 2019, and entitled Distractors Having Attachable Paddles, Impaction Devices, and Methods for Use in Total Ankle Replacement, International Application No. PCT/US2019/066398 filed Dec. 13, 2019, and entitled Distractors Having Attachable Paddles, Impaction Devices, and Methods for Use in Total Ankle Replacement, U.S. Provisional Application No. 62/899,646 filed Sep. 12, 2019, and entitled Trial Insert Assembly, International Application No. PCT/US2019/065025 filed Dec. 6, 2019, and entitled Trial Insert Assembly, U.S. Provisional Application No. 62/899,460 filed Sep. 12, 2019, and entitled Total Ankle Replacement Surgical Method, International Application No. PCT/US2019/066409 filed Dec. 13, 2019, and entitled Total Ankle Replacement Surgical Method, which are each hereby incorporated herein in their entireties.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), "contain" (and any form contain, such as "contains" and "containing"), and any other grammatical variant thereof, are open-ended linking verbs. As a result, a method or article that "comprises", "has", "includes" or "contains" one or more steps or elements possesses those one or more steps or elements, but is not limited to possessing only those one or more steps or elements. Likewise, a step of a method or an element of an article that "comprises", "has", "includes" or "contains" one or more features possesses those one or more features, but is not limited to possessing only those one or more features. Any examples of parameters are not exclusive of other parameters of the disclosed embodiments.

As used herein, the terms "comprising," "has," "including," "containing," and other grammatical variants thereof encompass the terms "consisting of" and "consisting essentially of." The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed compositions or methods.

All publications cited in this specification are herein incorporated by reference as if each individual publication were specifically and individually indicated to be incorporated by reference herein as though fully set forth.

Where one or more ranges are referred to throughout this specification, each range is intended to be a shorthand format for presenting information, where the range is understood to encompass each discrete point within the range as if the same were fully set forth herein.

It is to be understood that the above description is intended to be illustrative, and not restrictive. Numerous changes and modifications may be made herein by one of ordinary skill in the art without departing from the general spirit and scope of the disclosure as defined by the following claims and the equivalents thereof. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Also, the term "operably connected" is used herein to refer to both connections resulting from separate, distinct components being directly or indirectly coupled and components being integrally formed (i.e., monolithic). Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the disclosure may include only some of the described embodiments.

Components, aspects, features, configurations, arrangements, uses and the like described, illustrated or otherwise disclosed herein with respect to any particular embodiment may be similarly applied to any other embodiment disclosed herein. Accordingly, the inventions are not to be seen as limited by the foregoing description, but is only limited by the scope of the appended claims.

This written description uses examples to disclose the inventions, including the best mode, and also to enable any person skilled in the art to practice the inventions, including making and using any devices or systems and performing any incorporated methods. The patentable scope of the inventions are defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A joint-line referencing system comprising:
an alignment arm comprising a body having a first portion and a second portion, said first portion and said second portion defining a first side and a second side, said first portion having at least one first pin tube through-hole extending from said first side to said second side, the second portion having a first opening on said first side;
a first pin tube guide member receivable in said at least one first pin tube through-hole, said first pin tube guide member having a passageway therethrough;
an angelwing alignment member having a portion receivable in said first opening of said alignment arm;
an alignment foot secured to said second portion, said alignment foot having a handle extending away from said first side and a shim extending away from said second side; and
wherein said shim is positionable in a joint between a first bone and a second bone, said alignment arm is alignable relative to a first bone, and said first pin tube guide member is operable for securing a pin into the first bone.

2. The joint-line referencing system of claim 1, wherein said alignment arm comprises a second pin tube-hole disposed between said at least one first pin tube through-hole and said first opening, and further comprising a second pin tube guide member receivable in said second pin tube through-hole, said second pin tube guide member having a passageway therethrough.

3. The joint-line referencing system of claim 1, wherein said shim comprises a first flat surface and a second flat surface.

4. The joint-line referencing system of claim 3, wherein said first flat surface of said shim is angled relative to said second flat surface.

5. The joint-line referencing system of claim 1, wherein said shim comprises a longitudinal axis disposed parallel to an axis of said at least one first pin tube through-hole.

6. The joint-line referencing system of claim 1, wherein said shim is disposed in alignment with said first opening so that said shim is disposed in alignment with said angelwing alignment member.

7. The joint-line referencing system of claim 1, wherein said shim comprises a connector offset from said first surface and said second surface, and said connector is connectable to said second portion of said body of said alignment arm spaced from said first opening.

8. The joint-line referencing system of claim 7, wherein said handle is connectable to said second portion of said body of said alignment arm spaced from said first opening, and said handle is aligned with said connector of said shim.

9. The joint-line referencing system of claim 1, wherein said shim and said handle of said alignment foot are fixedly connected to said second portion of said alignment arm.

10. The joint-line referencing system of claim 1, wherein said portion of said angelwing alignment member comprises a tab, and said first opening of said alignment arm comprises a slot for receiving said tab of said angelwing alignment member.

11. The joint-line referencing system of claim 1, wherein said second portion comprises a second opening on said first side for receiving a second alignment device, said second opening disposed between said first opening and said at least one first pin tube through-hole.

12. The joint-line referencing system of claim 11, further comprising said second alignment device comprising a laser alignment system.

13. The joint-line referencing system of claim 12, wherein said laser alignment system is operable to project a laser line alignable with the first bone.

14. The joint-line referencing system of claim 11, wherein said first opening comprises a first slot, and said second opening comprises a second slot parallel to said first slot.

15. The joint-line referencing system of claim 1, wherein said shim comprise a curved shim.

16. The joint-line referencing system of claim 15, wherein said alignment foot is pivotably attachable to said second portion of said alignment arm.

17. The joint-line referencing system of any of claim 1, wherein said at least one first pin tube through-hole comprises separate individual side-by-side openings or a plurality of overlapping pin tube openings.

18. The joint-line referencing system of claim 17, wherein said pin tube holes are oblong or elongated.

19. The joint-line referencing system of claim 1, wherein said angelwing alignment member comprises a planar L-shaped angelwing alignment member.

20. The joint-line referencing system of claim 1, wherein a first leg of said L-shaped angelwing alignment member comprises a tab receivable in said first opening, and a second leg of said L-shaped angelwing alignment member comprises an elongated opening, and further comprising an alignment rod extendable through said elongated opening and attachable to said angelwing alignment member.

21. The joint-line referencing system of claim 1, wherein said first portion of said alignment arm is angled relative to said second portion of said alignment arm.

* * * * *